(12) United States Patent
Inoue

(10) Patent No.: US 7,763,044 B2
(45) Date of Patent: Jul. 27, 2010

(54) ALIENATED THROMBUS CAPTURE DEVICE

(76) Inventor: Kanji Inoue, 98-13, Miyazaki-cho Shimogamo, Sakyo-ku, Kyoto-shi, Kyoto 606-0802 (JP)

( * ) Notice: Subject to any disclaimer, the term of this patent is extended or adjusted under 35 U.S.C. 154(b) by 1203 days.

(21) Appl. No.: 10/490,644

(22) PCT Filed: Sep. 28, 2001

(86) PCT No.: PCT/JP01/08604

§ 371 (c)(1), (2), (4) Date: Mar. 25, 2004

(87) PCT Pub. No.: WO03/030740

PCT Pub. Date: Apr. 17, 2003

(65) Prior Publication Data

US 2004/0243173 A1    Dec. 2, 2004

(51) Int. Cl.
*A61M 29/00* (2006.01)
(52) U.S. Cl. ..................... 606/200
(58) Field of Classification Search ........... 606/200, 606/113, 151
See application file for complete search history.

(56) References Cited

U.S. PATENT DOCUMENTS

| | | | |
|---|---|---|---|
| 5,954,745 A * | 9/1999 | Gertler et al. ............ | 606/200 |
| 6,142,987 A | 11/2000 | Tsugita | |
| 6,277,138 B1 | 8/2001 | Levinson et al. | |
| 6,361,545 B1 * | 3/2002 | Macoviak et al. .......... | 606/200 |
| 6,371,971 B1 * | 4/2002 | Tsugita et al. ............ | 606/200 |

FOREIGN PATENT DOCUMENTS

| | | |
|---|---|---|
| JP | 1-221155 | 9/1989 |
| JP | 10-504738 | 5/1998 |
| JP | 11-501227 | 2/1999 |
| JP | 2001-522639 | 11/2001 |
| WO | WO 96/12448 | 5/1996 |
| WO | WO 98/02203 | 1/1998 |
| WO | WO 99/44542 | 9/1999 |
| WO | WO 01/49215 A2 | 7/2001 |
| WO | WO 02/22046 A2 | 3/2002 |

OTHER PUBLICATIONS

Supplementary European Search Report dated Jan. 4, 2007, issued in corresponding European Application No. 01972621.5.

* cited by examiner

*Primary Examiner*—(Jackie) Tan-Uyen T. Ho
*Assistant Examiner*—Gregory A Anderson
(74) *Attorney, Agent, or Firm*—Westerman, Hattori, Daniels & Adrian, LLP

(57) ABSTRACT

An alienated thrombus capture device 1 has a ring portion 12 made of a wire member having foldable elasticity, an flexibly transformable linear stiffener portion 11 that penetrates the ring portion 12, a porous bursiform portion 13 whose opening edge portion 13a is mounted on the ring portion 12 and whose closed edge portion 13b is mounted on a part of a distal end side of the stiffener portion 11, and flexibly transformable support linear member portion 14 that is supported between the stiffener portion 11 and the ring portion 12 in a strained state. The support linear member portion 14 supports the ring portion 12 in a spread state with a distance between a support portion 14a on the stiffener portion 11 and a circumference of the ring portion 12 kept generally constant at least in a state that the ring portion 12 is spread.

29 Claims, 45 Drawing Sheets

ALIENATED THROMBUS CAPTURE DEVICE

FIELD OF THE ART

This invention belongs to the medical equipment field, and more specifically relates to an alienated thrombus capture device that is preferably used for transcutaneous treatment in a blood vessel.

BACKGROUND ART

Recently circulatory diseases such as arterial sclerosis and aortic aneurysms have especially been increasing. In order to treat aortic aneurysms, surgical thoracolaparotomy has been applied. Recently, however, low-invasive transcutaneous treatments have been adopted in which various types of devices such as an artificial blood vessel, a stent, a stent graft or a balloon are inserted into and detained in an affected area through a catheter introduced into a body from a dissected arterial blood vessel.

When transcutaneous treatment is provided to an aortic aneurysm with the above-mentioned technique, there might be a case where a thrombus that has pooled in an affected area becomes alienated and flows into a blood vessel through an inner wall of a blood vessel that has become fragile. In this case, when the alienated thrombus travels by blood flow into a narrow peripheral blood vessel, there is a risk that tissue ahead of the thrombus will become necrotized.

Especially, a thrombus blocking an arteria carotis communis in the head is immediately life-threatening.

In order to avoid the above-mentioned risk, an alienated thrombus capture device, referred to as a filter device, has been developed that is arranged at a peripheral side of an affected area where a device such as an artificial blood vessel is detained, and to capture and receive a thrombus that becomes alienated in the blood vessel. This kind of device has the following arrangement: either an opening edge portion or a closed distal end portion of a bursiform portion made of a mesh material is fixed to distal end portion of a flexible transport wire that is inserted into a catheter, the bursiform portion is enclosed in the catheter in a shape along the transport wire in a narrowed state, such that when the bursiform portion is released from a distal end of the catheter together with a distal end portion of the transport wire at an appropriate position located at a peripheral side of the affected area, an opening edge portion of the bursiform portion is spread open. In addition, the transport wire is arranged to pass through a lumen of an artificial blood vessel, which is released from a sheath into which the catheter is inserted, to the affected area after or at the same time the bursiform portion is released. Further, after the artificial blood vessel is detained at the affected area, the opening edge portion of the bursiform portion is narrowed by pulling the transport wire into the catheter. With this condition kept, the alienated thrombus capture device in which the thrombus is enclosed in the bursiform portion is pulled out of the body, so as to be retrieved by pulling it into the sheath.

In the above-mentioned conventional alienated thrombus capture device, a flexible wire is bent into a loop, both ends are bound and fixed to the transport wire and an opening edge portion of a bursiform portion is mounted on the loop of the wire. In another arrangement of the conventional alienated thrombus capture device, multiple flexible wires are shaped as a spindle, both ends of the multiple flexible wires being fixed to two points separated in a longitudinal direction on the transport wire, an opening edge portion of a bursiform portion is mounted on an intermediate portion in a longitudinal direction of each wire, and a closed distal end portion of the bursiform portion is mounted on a distal end portion of the wire.

However, for the first mentioned conventional arrangement, wherein the looped wire is used, since the looped wire is supported at a single point by the transport wire, it is difficult to coincide a direction of a center axis of the bursiform portion with a direction of blood flow, and the alienated thrombus capture device might incline and fail to capture a thrombus. In addition, after an artificial blood vessel is detained at an affected area, an opening width of the loop is narrowed when the wire is pulled into the catheter; however, a width of an opening edge portion of the bursiform portion that is still open tends to be wide, and a thrombus that has been enclosed inside the bursiform portion might get out from the opening edge. In this kind of alienated thrombus capture device, a part of the looped wire is made thin or cut so that the looped wire can be folded smaller when retrieved; however, this makes no difference in the problem that the device itself inclines.

For the later mentioned conventional arrangement, the multiple wires in a shape of a spindle are used, since the arrangement is complicated and the wires are bulky, it becomes hard to enclose multiple wires in the catheter. In addition, it is difficult for the opening edge portion of the bursiform portion to take its form along the inner wall of the blood vessel, due to the existence of wires. Thus, a thrombus might pass through a gap between the opening edge portion and the inner wall of the blood vessel. In order to solve the above-mentioned problem, the shape of the opening edge portion should be close to a perfect circle, which requires more wires, thereby making the arrangement more complicated and more bulky.

Further, as a problem common to the conventional alienated thrombus capture devices, since the transport wire is passed inside the artificial blood vessel, the arrangement as a whole becomes complicated and the transport wire might be a hindrance by entwining with other wires used to transport or to detain the artificial blood vessel.

SUMMARY OF THE INVENTION

The presently claimed invention intends to provide an alienated thrombus capture device with a simple arrangement that can capture an alienated thrombus during transcutaneous treatment without failure, such that there is no fear of spilling the thrombus out of the alienated thrombus capture device.

The alienated thrombus capture device in accordance with the presently claimed invention comprises a ring portion made of a wire member having foldable elasticity, a flexibly transformable linear stiffener portion that penetrates the ring portion, a porous bursiform portion whose opening edge portion is mounted on the ring portion and whose closed edge portion is mounted on a part of a distal end side of the stiffener portion, and an flexibly transformable support linear member portion that is supported between a part of the stiffener portion located at a proximal end side of the closed edge portion and the ring portion in a strained state, and is characterized in that the support linear member portion supports the ring portion in a spread state with a distance between a support portion for supporting the support linear member portion on the stiffener portion and an arbitrary portion on a circumference of the ring portion kept generally constant.

In accordance with this arrangement, since it is easy to generally coincide the direction of a center axis with the direction of blood flow because the spread ring portion is supported by the support linear member portion, an alienated thrombus can be captured and enclosed in the bursiform portion stably and surely without fail. Further, the alienated thrombus can be captured without fail when the ring portion makes abutting contact with the inner wall of the blood vessel because the ring portion follows contraction of a blood vessel and transforms moderately due to elasticity of the ring portion. Especially, since the bursiform portion is porous, the alienated thrombus capture device does not interfere with blood flow. In addition, when external force is applied directly to the ring portion or the support linear member portions are drawn close to the stiffener portion by external force with a strained state kept, the ring portion is folded to be small with its opening portion narrowed. As a result, it is possible to send the alienated thrombus capture device, which is inserted into a catheter with the ring portion folded, to a predetermined portion in a blood vessel. It is also possible to retrieve the alienated thrombus capture device without spilling out the captured thrombus from the bursiform portion, since the opening edge portion is narrowed with the ring portion folded. The support portion for supporting the support linear member portion on the stiffener portion is preferably arranged at a proximal end portion side of the closed edge portion of the bursiform portion, more preferably at a position where the ring portion is arranged or at a proximal end portion side of the position. Further, the stiffener portion may be separated from the transport device to transport the alienated thrombus capture device or may be integrated into the transport device. In either case it is preferable that at least two support linear member portions are provided.

When the ring portion is spread in a blood vessel, in order to coincide the direction of its center axis with the direction of blood flow more stably and to stabilize the alienated thrombus capture device, it is effective that multiple support linear member portions are arranged and support portions for supporting one end of each support linear member portion are set at equally divided points, each of which generally equally divides the circumference of the ring portion. In this case, in order to downsize the ring portion when the ring portion is folded with a more simple arrangement, it is preferable that the equally divided points are set to be points that generally bisect, trisect or quadrisect the circumference of the ring portion.

As a concrete example of an especially preferable support linear member portion, a thread made of a fiber material or a wire made of resin or metal that supports the posture of the ring portion by tensile force acting between the stiffener portion and the ring portion may be used.

In order to fold the ring portion into compact size with ease, it is preferable that points that generally equally divide the circumference of the ring portion into an even number of four and over are provided and the support portions for supporting the support linear member portions are formed at either each of middle points between adjacent dividing points, at each of the dividing points or at every other dividing point. Thus, the ring portion can be folded so that the every other dividing point forms a peak of a chevron facing the distal end side of the stiffener portion, and every other dividing point adjacent to the dividing point forming a peak forms a bottom of a valley facing the proximal end side of the stiffener portion.

As a concrete arrangement that can both stabilize the posture of the ring portion and downsize the folded ring portion, four dividing points are provided on the ring portion and the support portions for supporting the support linear member portions are formed at middle points between adjacent dividing points. Middle points are not necessarily a center between adjacent dividing points, but may deviate a little towards either one of the adjacent dividing points.

In order to stabilize the posture of the ring portion and to fold the ring portion into a compact size with a simple arrangement, one end portion of the support linear member portion may be fixed to the support portion on the stiffener portion and the other end portion of the support linear member portion may be fixed to the support portion on the ring portion. As a simple arrangement to attain the above-mentioned object, for example, each support linear member portion may be of a single linear member and both ends of the linear member may be mounted on the support linear member portion and the ring portion.

In addition, as a simple arrangement to stabilize the posture of the ring portion and to fold the ring portion into a compact size, a pair of adjacent support linear member portions may comprise a single flexibly transformable support linear member, both ends of the support linear member may be fixed to the support portion on the stiffener portion and an intermediate portion may be supported in a slidably movable manner by a pair of adjacent support portions on the ring portion. Further, one end portion of the support linear member portion may be fixed to the support portion on the stiffener portion, the other end portion may be fixed to one of the support portions on the ring portion and an intermediate portion may be supported in a slidably movable manner by the support portion at the adjacent portion of the support portion that fixes the other end portion.

When the alienated thrombus capture device is retrieved, in order to fold the ring portion into a small size with ease by effectively binding multiple support linear member portions, it is especially preferable that a tubular slider portion into which the stiffener portion is inserted, and which is slidably movable along the stiffener portion, is arranged on the stiffener portion. With this arrangement, the support linear member portions to be enclosed inside the slider portion can be gathered along the stiffener portion by moving the slider portion toward a distal end direction of the stiffener portion. In this case, for example, when the slider portion is pushed by the distal end of the catheter so as to make a sliding movement, in order not to emerge into the catheter, it is preferable that a big diameter portion whose diameter is bigger than that of a distal end portion of the slider portion is formed at a proximal end portion of an outer circumferential wall of the slider portion. Further, in order to restrain an unnecessary movement of the slider portion so that the slider portion makes a sliding movement within the minimum range, it is preferable that a stopper portion that restrains the slider portion from moving to the proximal end side is formed at a position located at a proximal end side to the support portion, for supporting the support linear member portion on the stiffener portion and also located at a proximal end side to the proximal end portion of the slider portion.

As an especially preferable arrangement of an alienated thrombus capture device that is separated from a transport device to transport the alienated thrombus capture device, the alienated thrombus capture device is so arranged to be detachably mounted on a transport device to transport the alienated thrombus capture device, and the proximal end side of the stiffener portion is directly or indirectly pushed or pulled by the transport device so as to be transported. With this arrangement, prior to transporting a device such as an artificial blood vessel to an affected area, the alienated thrombus capture device can be arranged at a predetermined portion in a blood vessel at a peripheral side to the affected area and retrieved after the device is detained, then the alienated thrombus capture device does not disturb a transporting/detaining process of the device. In addition, the alienated thrombus capture device can be retrieved with ease during a process of detaining the device.

In order to make it easy to transport the alienated thrombus capture device separated from the transport device in using/retrieving the alienated thrombus capture device, it is preferable that a held portion to be held by the transport device is formed at the proximal end portion of the stiffener portion. More concretely, when the transport device comprises a holding member having an engaging portion having loop shape that is selectively expandable and shrinkable at its distal end portion, it is preferable that the held portion is formed by partially curving or bending the proximal end portion of the stiffener portion and that the held portion is held by the shrunken engaging portion after the held portion is hooked to the engaging portion by passing the expanded engaging portion of the hold member. In order to make an engaged state of the transport device having the held portion be in a good state where the stiffener portion is securely held by the transport device, it is especially preferable that a slip stopper portion is formed that prevents separation from the engaging portion by making an engagement with a part of the shrunken engaging portion of the holding member on the held portion.

In addition, in order to make it easy to retrieve the alienated thrombus capture device by pulling the engaging portion having the held portion which is hooked to the holding member in a state that the held portion does not contact an inner wall of a blood vessel, it is preferable that a maximum distance between a center axis of the ring portion and the proximal end portion of the stiffener portion is set within a radius size of the ring portion. In order to embody this arrangement easily and concretely, it is preferable that a spiral portion whose axial center generally coincides with a center axis of the ring portion by transforming the stiffener portion partially is formed at a distal end side of the held portion on the proximal end portion of the stiffener portion.

When the stiffener portion is integrally formed with or mounted on a part of a transport device for transporting the alienated thrombus capture device, the alienated thrombus capture device can be easily retrieved without using a transport device separated from the alienated thrombus capture device if necessary during detaining a device such as an artificial blood vessel, and the alienated thrombus capture device can be transported together with the device easily. Especially in this case, a posture of the ring portion may be maintained in a good state by the use of multiple support linear member portions. Since the stiffener portion is integrally formed with the transport device, a posture of the ring portion may also be maintained with its center axis coinciding with a direction of blood flow by the use of a single support linear member portion. In addition, another embodiment of the alienated thrombus capture device integrally formed with the transport device represented is that the alienated thrombus capture device can be moved by directly operating the proximal end side of the stiffener portion by a user.

Irrespective of the alienated thrombus capture device integrally formed with the transport device or separated from the transport device, in order to guide the alienated thrombus capture device by the alienated thrombus capture device itself and to stabilize a posture of the ring portion in a blood vessel while transporting the alienated thrombus capture device to an appropriate position in a peripheral narrow blood vessel, it is preferable that a guide portion is formed by elongating the distal end portion of the stiffener portion toward a distal end side from the closed edge portion of the bursiform portion and partially curving or bending the elongated distal end portion.

In order to fold the ring portion into a preferable shape easily, it is preferable that support portions are formed on either one of middle positions between the adjacent dividing points, on dividing points or on every other dividing point out of the dividing points set on the ring portion, and a folded habit to fold the ring portion in a wavy shape by approaching the ring portion to the stiffener portion, so that every other dividing point forms peaks of chevrons facing the distal end side of the stiffener portion and the dividing points adjacent to the dividing points that form the peaks of the chevrons form bottoms of valleys facing the proximal end side of the stiffener portion, is given to the ring portion beforehand. Further, it is also preferable that the ring portion is in a wavy shape corresponding to the folded habit also in a spread state. In addition, in order to make a shape of the folded ring portion more compact, it is preferable that a projecting portion further projecting to the proximal end side of the stiffener portion is formed at a position to be a bottom of a valley when the ring portion is folded.

DETAILED DESCRIPTION OF THE INVENTION

The invention will be described in detail with reference to the embodiments thereof shown in the accompanying drawings.

Figure 1:
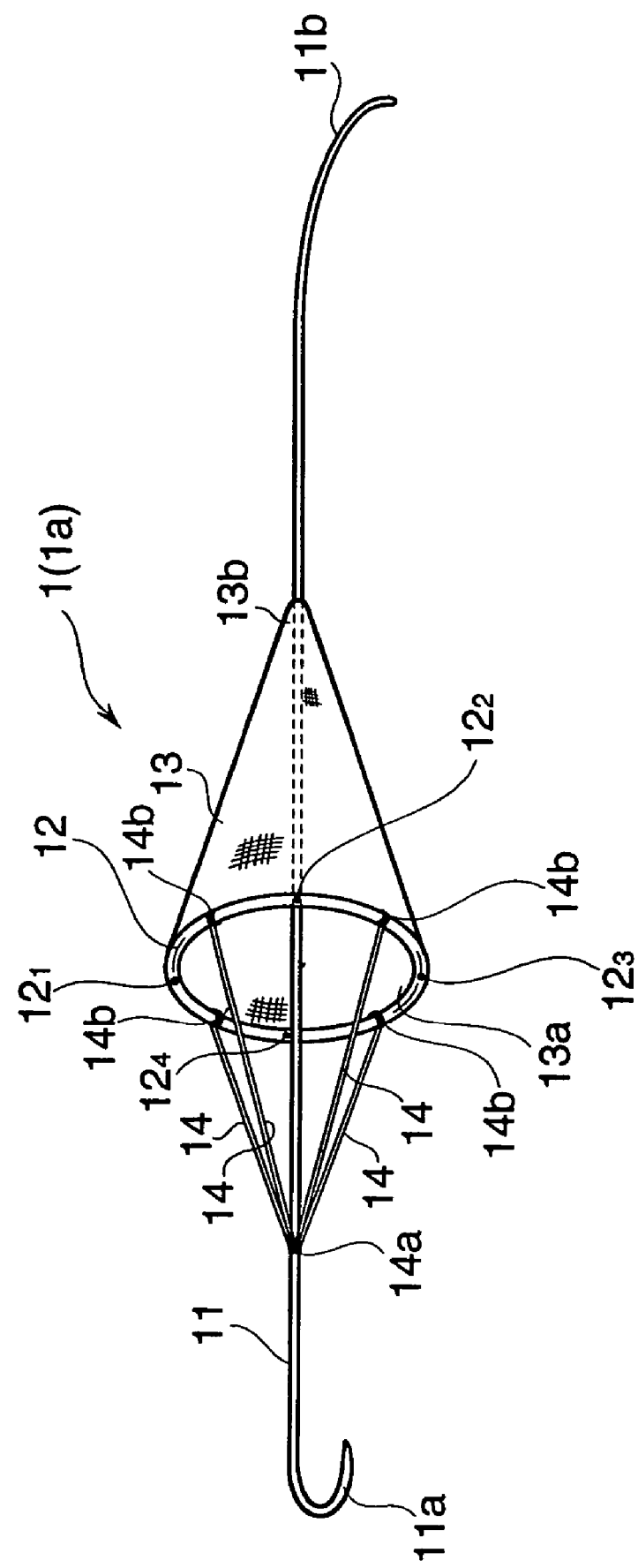
FIG. 1 is a perspective view showing a spread state of an alienated thrombus capture device in accordance with a first embodiment of the presently claimed invention.

An alienated thrombus capture device 1 in the first embodiment is the name of a filter device that is used, for example, in order to catch a thrombus alienated from an affected area when conducting a transcutaneous treatment such as inserting a sheath or a catheter into a blood vessel so as to detain various types of devices such as an artificial blood vessel at an affected area such as arterial sclerosis or aortic aneurysm. The alienated thrombus capture device mainly comprises, as shown in FIG. 1, a stiffener portion 11, a ring portion 12, a bursiform portion 13 and a support linear member portion 14.

The stiffener portion 11 comprises a thin ductile wire made of nickel titanium alloy that is superior in resilient restoration. In this embodiment, a wire whose length is, for example, about 10 centimeters is used, wherein one end at a proximal end side thereof is curved into the shape of a J character so as to form a hook portion 11a as a portion to be held, and the other end at a distal end side thereof is curved in a shape of a moderate partial arc so as to form a guide portion 11b. The stiffener portion 11 is preferably made of a single wire, however, it may be made of multiple wires integrated into a single entity.

Figure 2:
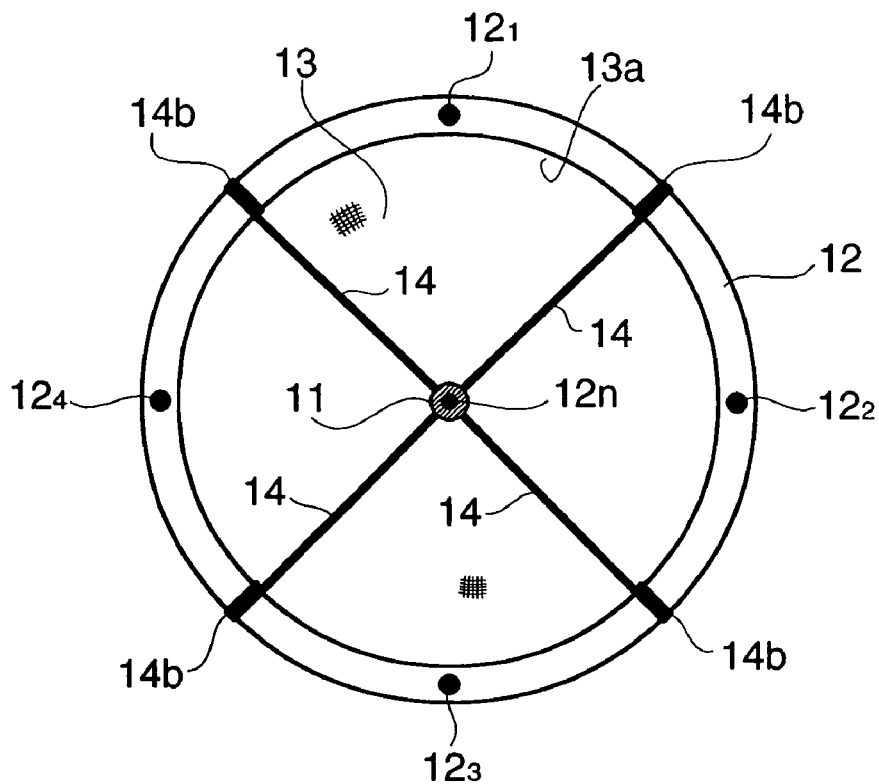
FIG. 2 is a partial magnified longitudinal cross-sectional view cut at a proximal end portion side of a stiffener portion of the alienated thrombus capture device of the first embodiment.

The ring portion 12 is made of a wire having a similar material to that of the stiffener portion 11, is formed into a circular form with a diameter of, for example, about 8 to 10 mm, and is arranged in a posture such that a center axis $12n$ (refer to FIG. 2) is generally aligned with the stiffener portion 11 at a position separated from the proximal end side of the stiffener portion 11 by about one third of the longitudinal length of the stiffener portion 11. In this embodiment, the ring portion 12 is made of a wire bent into a circle with its both ends connected; however, the ring portion 12 may be strengthened with a wire or wires wound in a circle in multiple times. The ring portion 12 has, as shown in FIG. 2, dividing points $12_1$, $12_2$, $12_3$, $12_4$ each of which generally quadrisects a circumference of the circle. The ring portion 12 is given a folded shape beforehand so that a pair of facing dividing points $12_1$, $12_3$ form bottoms of valleys when folded to face the proximal end side of the stiffener portion 11 by an external force and the pair of dividing points $12_2$, $12_4$ form peaks of chevrons when folded to face the distal end side of the stiffener portion 11 by the external force. Thus, the ring portion 12 forms a wavy shape as a whole after it is folded.

Figure 3:
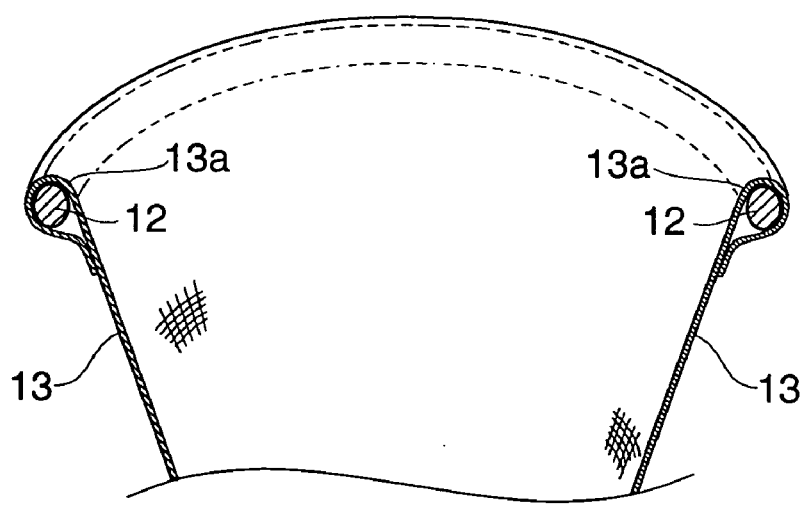
FIG. 3 is a partial magnified transversal cross-sectional view showing a state of a bursiform portion mounted on a ring portion of the alienated thrombus capture device.

The bursiform portion 13 is made from a flexible tensile porous triangle sheet formed into a circular conic bursiform shape with its opening edge portion $13a$ mounted on the ring portion 12 and with its closed edge portion $13b$ mounted on the stiffener portion 11 at a position separated from the distal end side of the stiffener portion 11 by about one-third or one-half of the longitudinal length of the stiffener portion 11. The sheet is made of a biomaterial, for example, polyester, polyethylene, polypropylene, polyurethane, nylon or the like with a plurality of porosities or in a porous shape woven into a mesh or a net, so as to be blood permeable and to be able to catch an alienated thrombus. In this embodiment, the bursiform portion 13 is made of polyester in a sheet having 80 to 200 μm in texture. In mounting the bursiform portion 13 on the ring portion 12, as shown in FIG. 3, the opening edge portion $13a$ of the bursiform portion 13 is wound around the ring portion 12 into a cylinder from an inner periphery to an outer periphery thereof and then sutured with a thread or bonded. The closed edge portion $13b$ of the bursiform portion 13 is fixedly mounted on the stiffener portion 11 by means of a suture or adhesive to prevent it from opening.

The support linear member portions 14 are made of, as shown in FIG. 1, flexible and transformable linear members each of whose first end is fixed to a portion located at the proximal end side of the stiffener portion 11 and each of whose of second end is fixed to a support portion $14a$ or $14b$ set on the circumference of the ring portion 12 in a tie-on manner and is arranged in a state having a tension when the ring portion 12 is spread. The support portion $14a$ is set at a position separated from the proximal end side of the stiffener portion 11, for example, by one-fifth of the longitudinal length of the stiffener portion 11 and the proximal end portion of the support linear member portion 14 is tied to the support portion $14a$ and is then fixed to the stiffener portion 11 by means of an adhesive or the like. The support portion $14b$ is, as shown in FIG. 2, set at each general midpoint between adjacent dividing points $12_1$ and $12_2$, $12_2$ and $12_3$, $12_3$ and $12_4$, $12_4$ and $12_1$, on the circumference of the ring portion 12, in other words, at four points each generally quadrisecting the circumference of the ring portion 12. As a wire member functioning as the above support linear member portion 14, a thread made of a high-strength polyarylate fiber is used in this embodiment; however, a wire member made of an appropriate material that has enough strength and elasticity and to which tension can be applied by the action of an external force, such as a thread made of another fiber material, a metal wire made of the same material as that of the stiffener portion 11 or other material, a resin thread or a resin wire or the like may be used.

Figure 4:
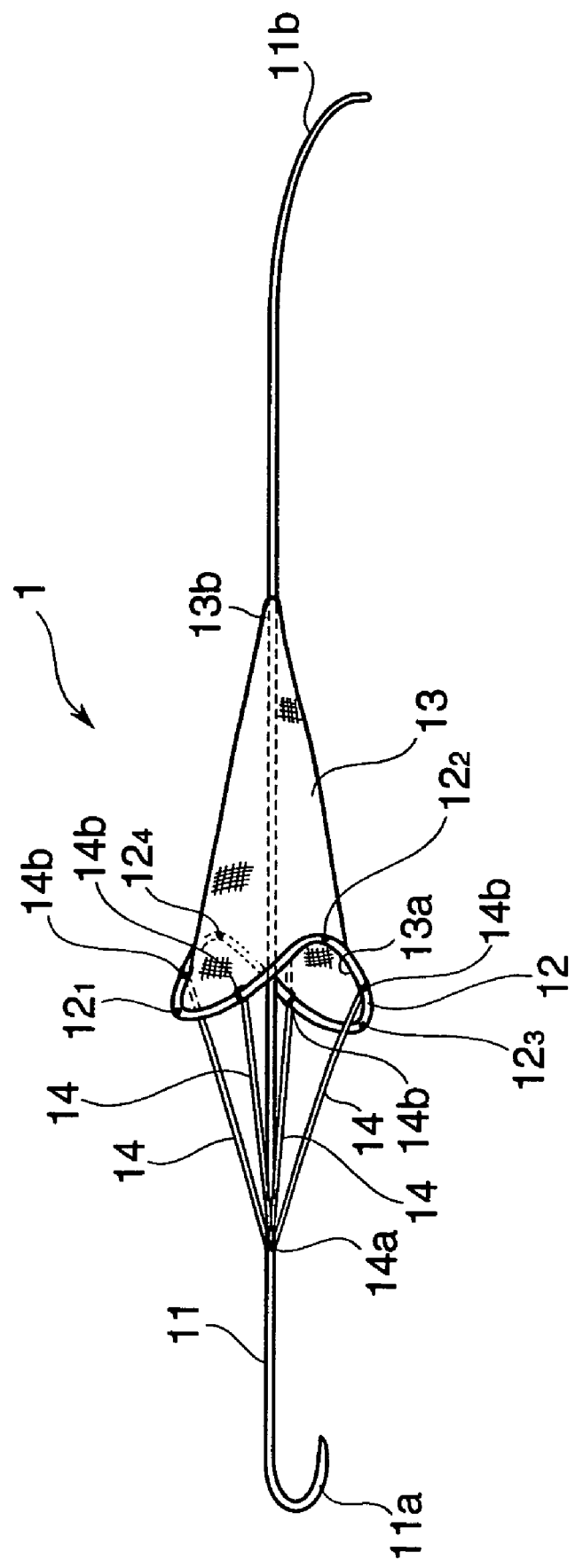
FIG. 4 is a perspective view showing a process of folding the alienated thrombus capture device.
Figure 5:
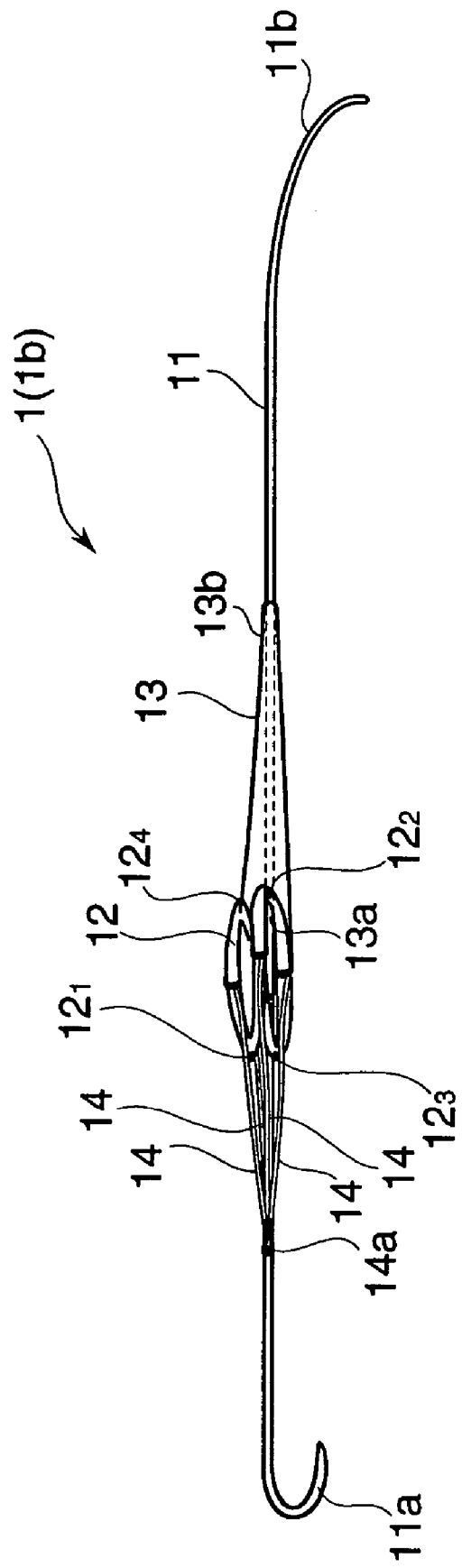
FIG. 5 is a perspective showing a folded state of the alienated thrombus capture device.

The alienated thrombus capture device 1 having the above arrangement changes its state from an extended state $1a$ shown in FIG. 1 to a bent state $1b$ wherein the ring portion 12 is gradually folded by an external force so of dividing points $12_1$ and $12_3$ face the distal side of the stiffener portion, and dividing points $12_2$ and $12_4$ face the proximal side thereof and the bursiform portion 13 is folded as shown in FIG. 4. The ring portion 12 is further folded until the pairs of dividing points $12_1$ and $12_3$, and $12_2$ and $12_4$ make an abutting contact each other as shown in FIG. 5. In this folded state $1b$, the opening edge portion $13a$ of the bursiform portion 13 is almost completely closed.

Figure 7:
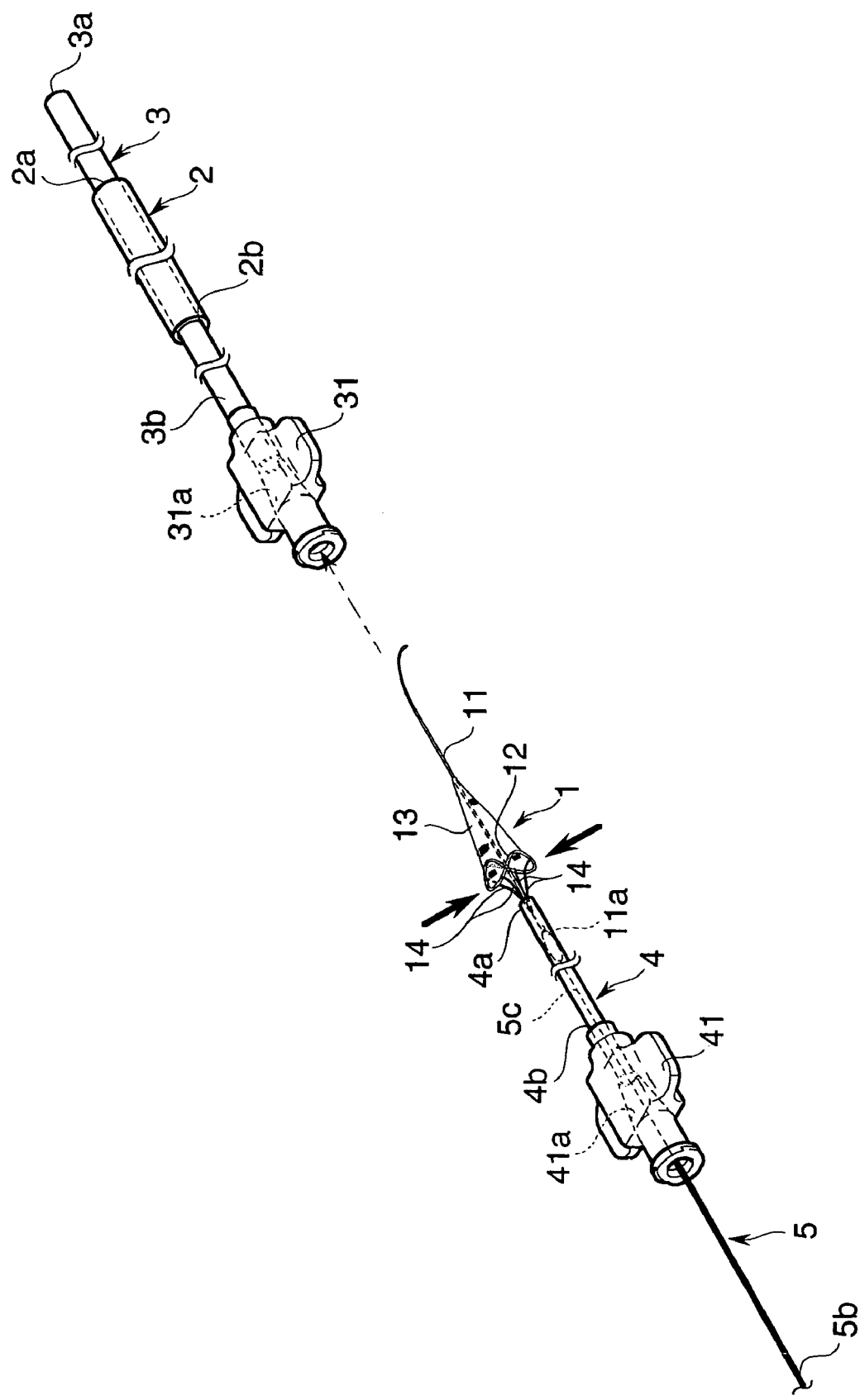
FIG. 7 is a perspective view showing the transport device used in this embodiment.

The alienated thrombus capture device 1 that can be folded by the above process is transported by a transport device A to be explained next. The transport device A comprises, as shown in FIG. 7, a sheath 2, a first catheter 3 that is to be inserted into the sheath 2 through an adaptor, not shown in the drawings, a second catheter 4 that is to be inserted into the first catheter 3 through a connector 31 to be mounted on a proximal end portion $3b$ of the first catheter 3 and a wire 5 as a holding member that is inserted into the second catheter 4 through a connector 41 mounted on a proximal end portion $4b$ of the second catheter 4 and that also serves as a tow member. When inserting the alienated thrombus capture device 1 into a blood vessel as a practical matter, a cartridge with a check valve or other auxiliary device is mounted on an appropriate portion in order to prevent bleeding. Since each device constituting the transport device A is commonly used, a brief explanation will be given next.

The sheath 2 is arranged so that its distal end portion $2a$ is directly inserted into an artery of a human body and has an enough girth and flexibility. The first catheter 3 is a long catheter whose outer diameter is about 7 fr. (2.1 mm) and its distal end portion $3a$ side is inserted into the sheath 2 and projected from the distal end portion $2a$ of the sheath 2 so as to reach near an affected area in a blood vessel. The connector 31 mounted on the proximal end portion $3b$ of the first catheter 3 has a through hole $31a$ in a shape of a funnel gradually narrowed from a proximal end portion side to a distal end portion side. The second catheter 4 has an outer diameter of about 5 fr. (1.5 mm) so as to be inserted into a lumen of the first catheter 3 and is a longer catheter than the first catheter 3. The connector 41 mounted on the proximal end portion $4b$ of the second catheter 4 is similar to the connector 31 and has a through hole $41a$ whose diameter is a little smaller than that of the connector 31. The wire 5 is made of a flexible metal having a diameter allowing it to be inserted into a lumen of the second catheter 4 and having a sufficient length that a proximal end portion $5b$ that is inserted into the second catheter 4 and that projects from a proximal end of the connector 41 can be operated by hand and a distal end portion $5a$ can project over the distal end portion $3a$ of the first catheter 3. A loop shaped engaging portion $5c$ is formed at the distal end portion $5a$, and a distal end portion of the engaging portion $5c$ is partially bent to form a projecting portion $5c1$ projecting in the shape of a mountain.

Next, a method to transport the alienated thrombus capture device 1 by using the above transport device A will be described.

Figure 6:
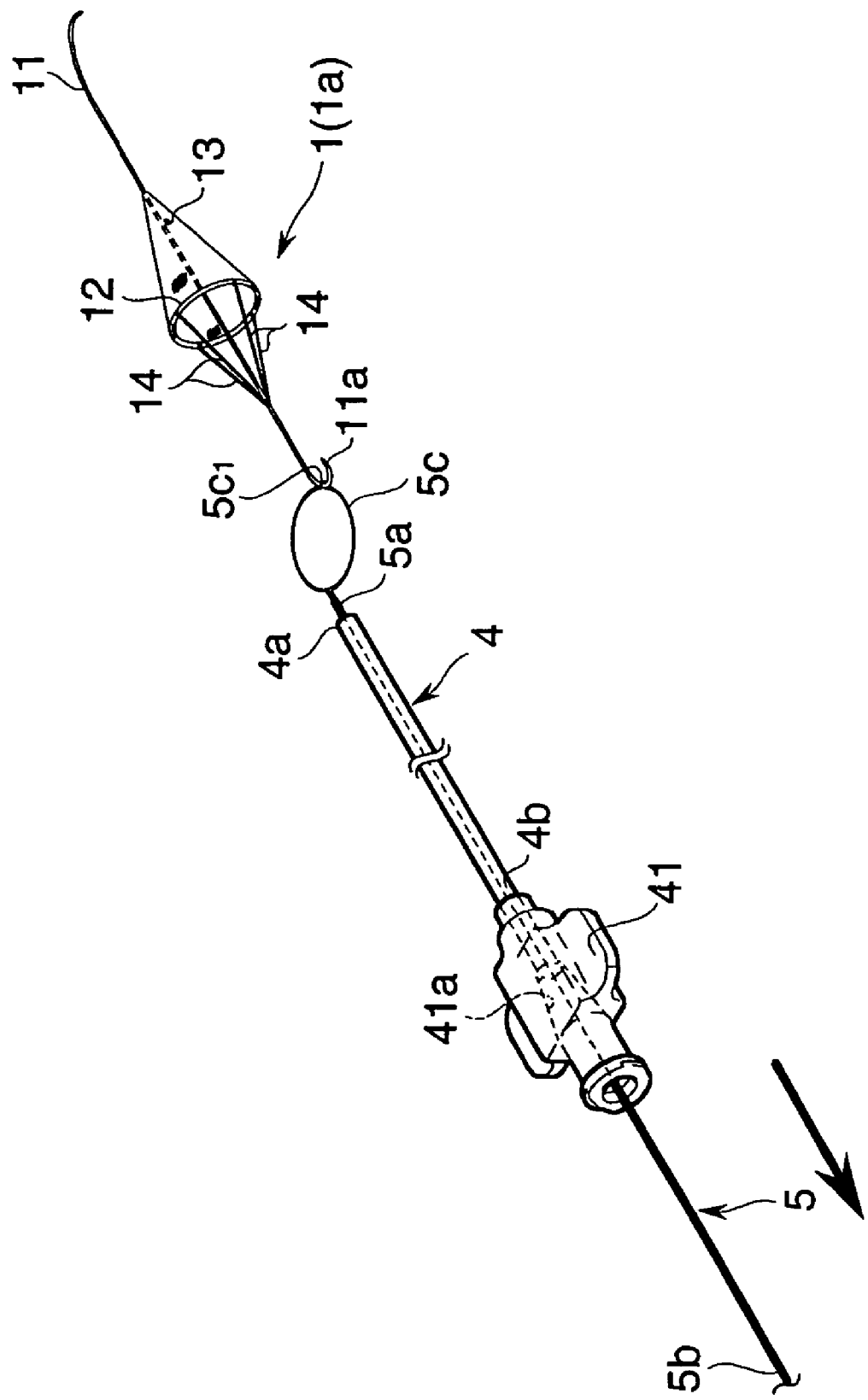
FIG. 6 is a magnified perspective view showing a state of the alienated thrombus capture device held by a part of a transport device used in this embodiment.

First, prior to a transcutaneous treatment, as shown in FIG. 6, outside a body, the connector 41 is mounted on the second catheter 4 and the wire 5 is inserted into the connector 41 and the second catheter 4 until the engaging portion $5c$ of the wire 5 projects out of the distal end of the second catheter 4. The alienated thrombus capture device 1 is pulled such that the hook portion 11a is engaged with the engaging portion 5c by pulling the proximal end portion 5b of the wire 5 projecting from the proximal end side of the connector 41. At this time, if the hook portion 11a is fittingly inserted into the projecting portion 5c1, an engaging state of the engaging portion 5c and the hook portion 11a can be made stable. From this state, the proximal end portion 5b of the wire 5 is pulled toward a proximal end side of an extending direction (a direction of the arrow in FIG. 6), then the proximal end side of the stiffener portion 11 is pulled into the distal end portion 4a of the second catheter 4 while keeping the engaging state of the engage portion 5c and the hook portion 11a as shown in FIG. 7. The wire 5 is further pulled to a position where the support portion 14a on the stiffener portion 11 is pulled into the second catheter 4, then the support linear member portion 14 is pulled into the second catheter 4 while keeping a tensed state between an opening edge of a lumen at the distal end of the second catheter 4 and the ring portion 12. Due to the force by which the support linear member portion 14 is constricted between the second catheter 4 and the ring portion 12, the ring portion 12 is folded into a wavy shape with the dividing points $12_1$ and $12_3$ forming bottoms of valleys and the dividing points $12_2$ and $12_4$ forming peaks of chevrons in accordance with a folded habit that has been given beforehand. The wire 5 is then fixed to the second catheter 4 by the use of an appropriate device.

Figure 8:
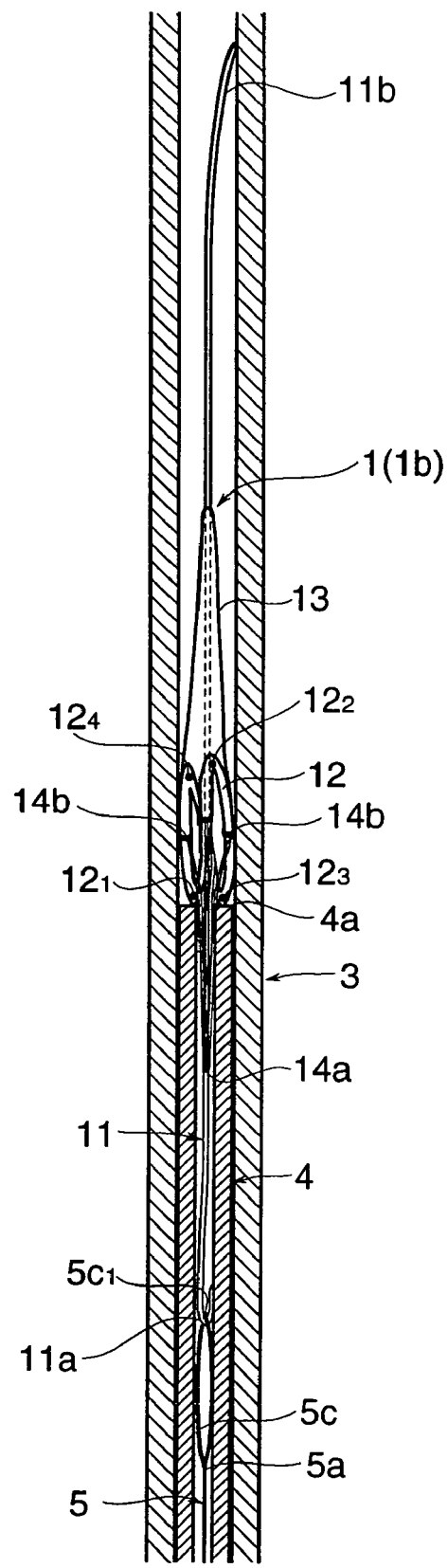
FIG. 8 is a perspective view showing a state inside the transport device of this embodiment.

Next, as shown in FIG. 7, the ring portion 12 is folded so as to make it compact by pinching it with fingers in the direction shown by the arrows in FIG. 7 and the alienated thrombus capture device 1 is inserted such that it is held by the second catheter 4 and the wire 5. A relative positional relationship between the second catheter 4, the wire 5 and the alienated thrombus capture device 1 is kept generally constant into the first catheter 3 through the connector 31. Further, as shown in FIG. 8, the alienated thrombus capture device 1 that is held by the second catheter 4 and the wire 5 is transported toward a direction of the distal end portion 3a of the first catheter 3 with the distal end of the second catheter 4 pushing against the dividing points $12_1$, $12_3$ as the bottoms of the valleys of the ring portion 12 by an operation of paying out the second catheter 4 into the first catheter 3. In this state, the alienated thrombus capture device 1 is in a completely folded state. The distal end portion 2a of the sheath 2 and the distal end portion 3a of the first catheter 3 are preferably inserted into a blood vessel in a body, for example, an aorta in a crural area. Especially, it is preferable that the distal end portion 3a of the first catheter 3 reaches a position where the alienated thrombus capture device 1 is arranged near a diseased portion.

Next, a method to transport the alienated thrombus capture device 1 to a predetermined portion in a blood vessel and to release it will be explained with reference to FIG. 9 through FIG. 13. Here, for example, the alienated thrombus capture device 1 is transitionally detained in a left arteria carotis communis 71 located downstream of a blood flow B.F when conducting a transcutaneous practice such as detaining an artificial blood vessel 8 (refer to FIG. 14) in an aortic aneurysm (hereinafter referred to as a diseased portion 7x) generated between the left arteria carotis communis 71 and a brachiocephalic trunk 72 in an aortic arch 7 of a chest. A similar method can be applied to other blood vessels (for example, the brachiocephalic trunk 72, a right arteria carotis communis, not shown in drawings, that bifurcates downstream, a thyrocervical trunk 73 or an abdominal artery) depending on a position of the diseased portion 7x.

Figure 9:
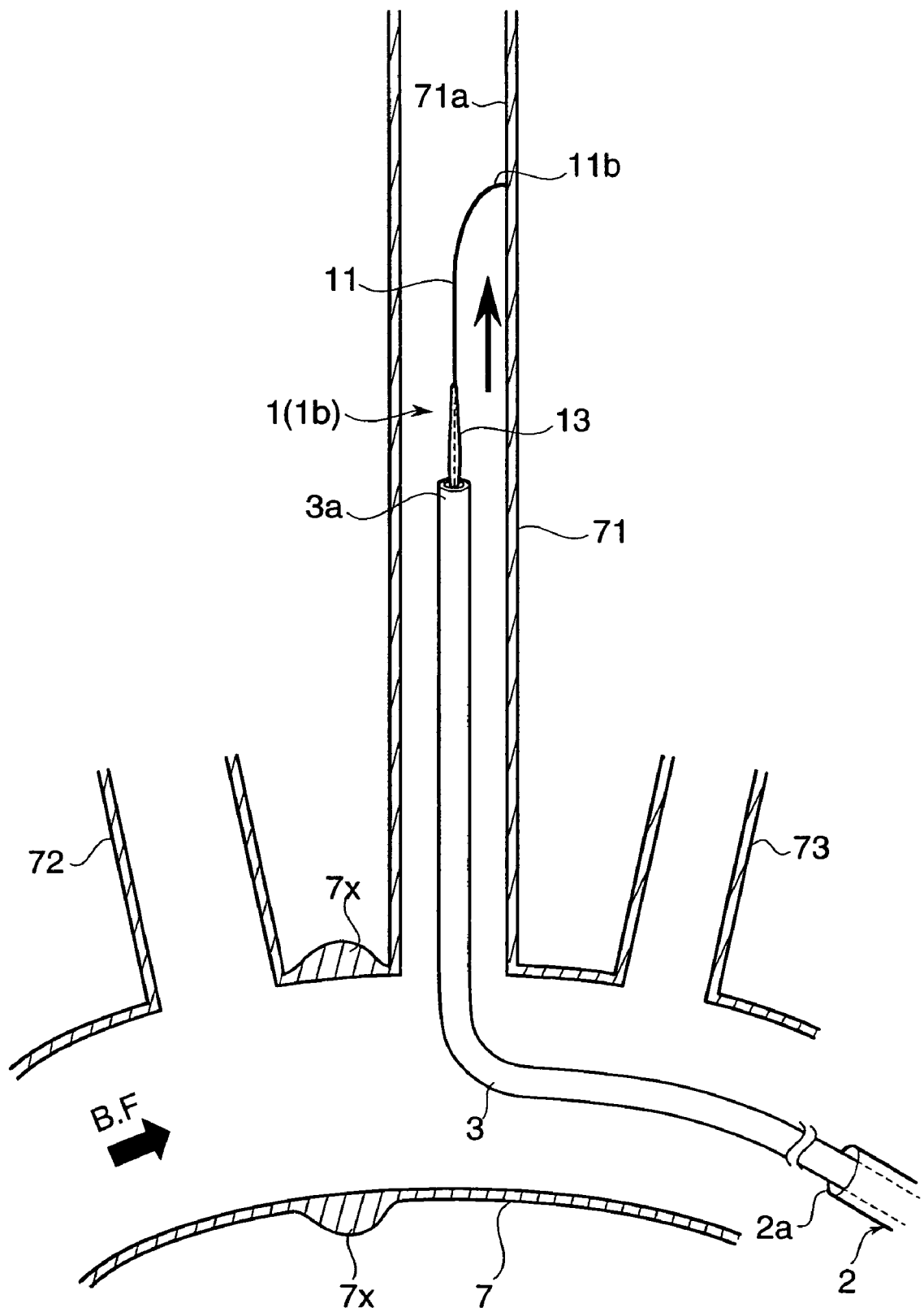
FIG. 9 is an explanatory view showing a transport process to arrange the alienated thrombus capture device at a predetermined portion of blood vessel.
Figure 10:
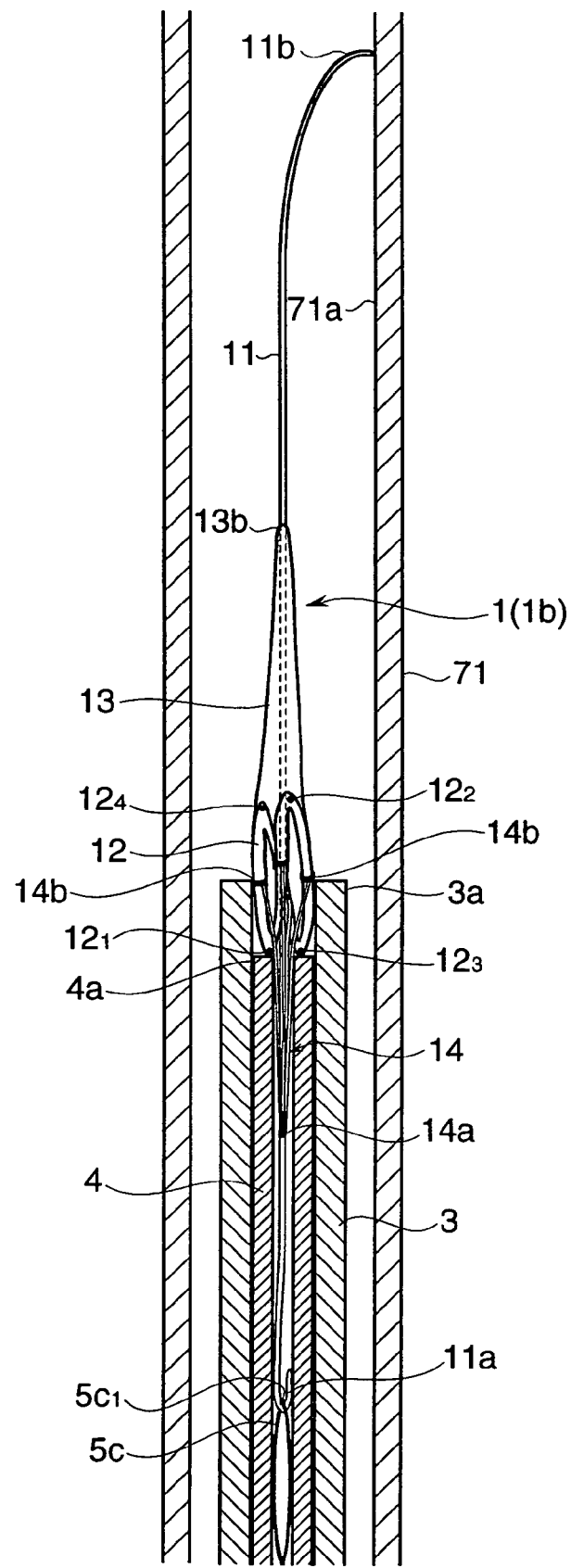
FIG. 10 is a partial magnified longitudinal cross-sectional view of FIG. 9.

The following operation is conducted while taking an X-ray. First, as shown in FIG. 9, the first catheter 3 is sent to the left arteria carotis communis 71 (hereinafter sometimes referred to as "blood vessel" for short) through the aortic arch 7 from the distal end portion 2a of the sheath 2 inserted into the aorta through a femoral region. Then the first catheter 3 is paid out together with the wire relatively fixed to the second catheter 4, as shown in FIG. 8, so as to expose the distal end side of the alienated thrombus capture device 1 at a predetermined position in the blood vessel 71 through the distal end portion 3a of the first catheter 3. At this position, the guide portion 11b formed on the stiffener portion 11 makes abutting contact with an inner wall 71b of the blood vessel 71 slightly. The state of the distal end portion 3a of the first catheter 3 is shown in FIG. 10 in a magnified general cross-sectional view. More specifically explaining based on FIG. 10, the second catheter 4 reaches near the distal end of the first catheter 3 inside the first catheter 3, and the engaging portion 5c of the wire 5, the proximal end portion side of the stiffener portion 11 and the proximal end side of the support linear member portion 14 are enclosed in the second catheter 4. The ring portion 12 is kept in a wavy folded state by being pressed by the inner walls of the first catheter 3 from both sides. With this state, the distal end of the second catheter 4 makes abutting contact with the dividing points $12_1$, $12_3$ that form the bottoms of the valleys. In other words, in this state, the alienated thrombus capture device 1 is in a generally completely folded state 1b.

Figure 11:
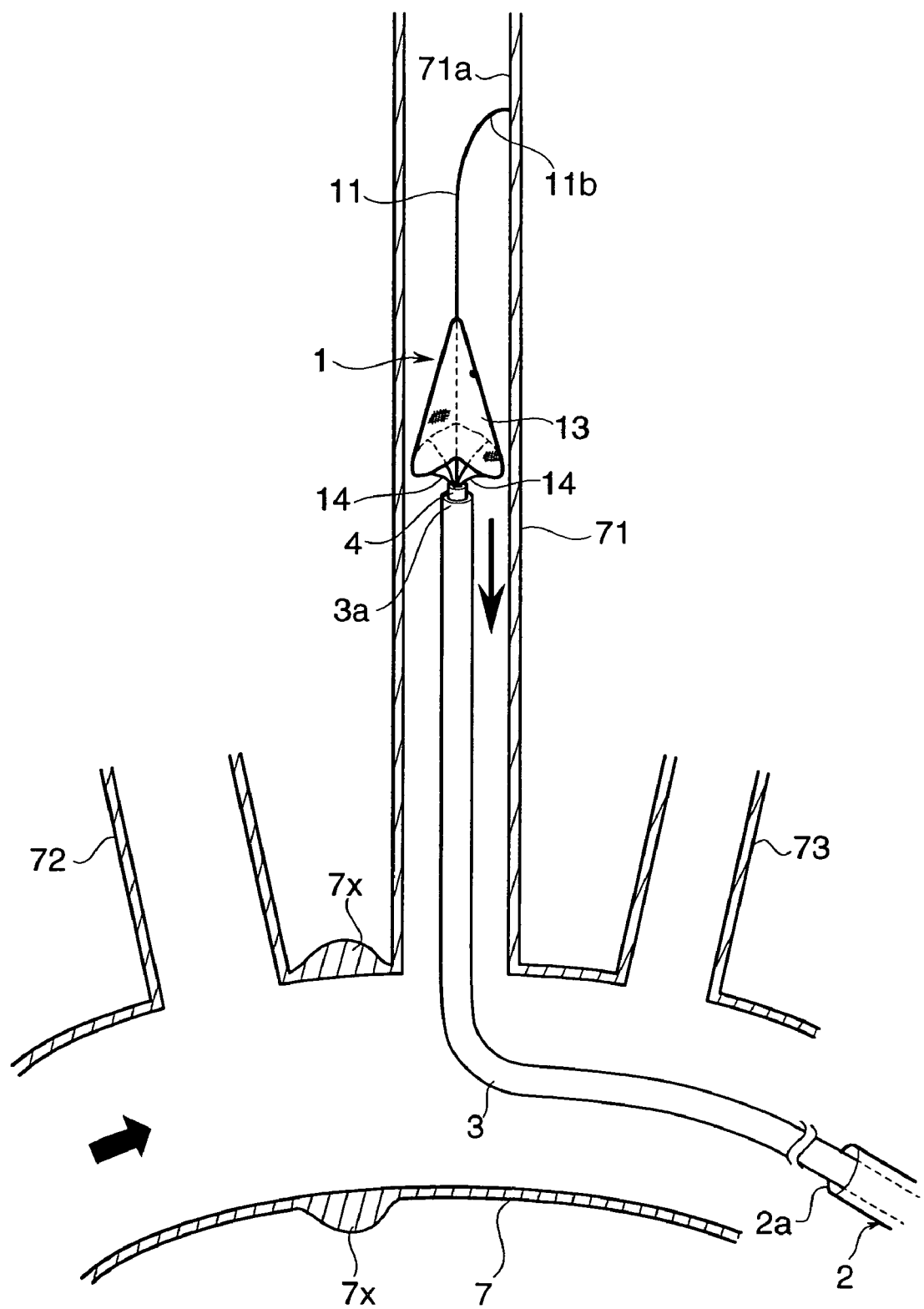
FIG. 11 is an explanatory view showing a transport process to arrange the alienated thrombus capture device at the predetermined portion of blood vessel.
Figure 12:
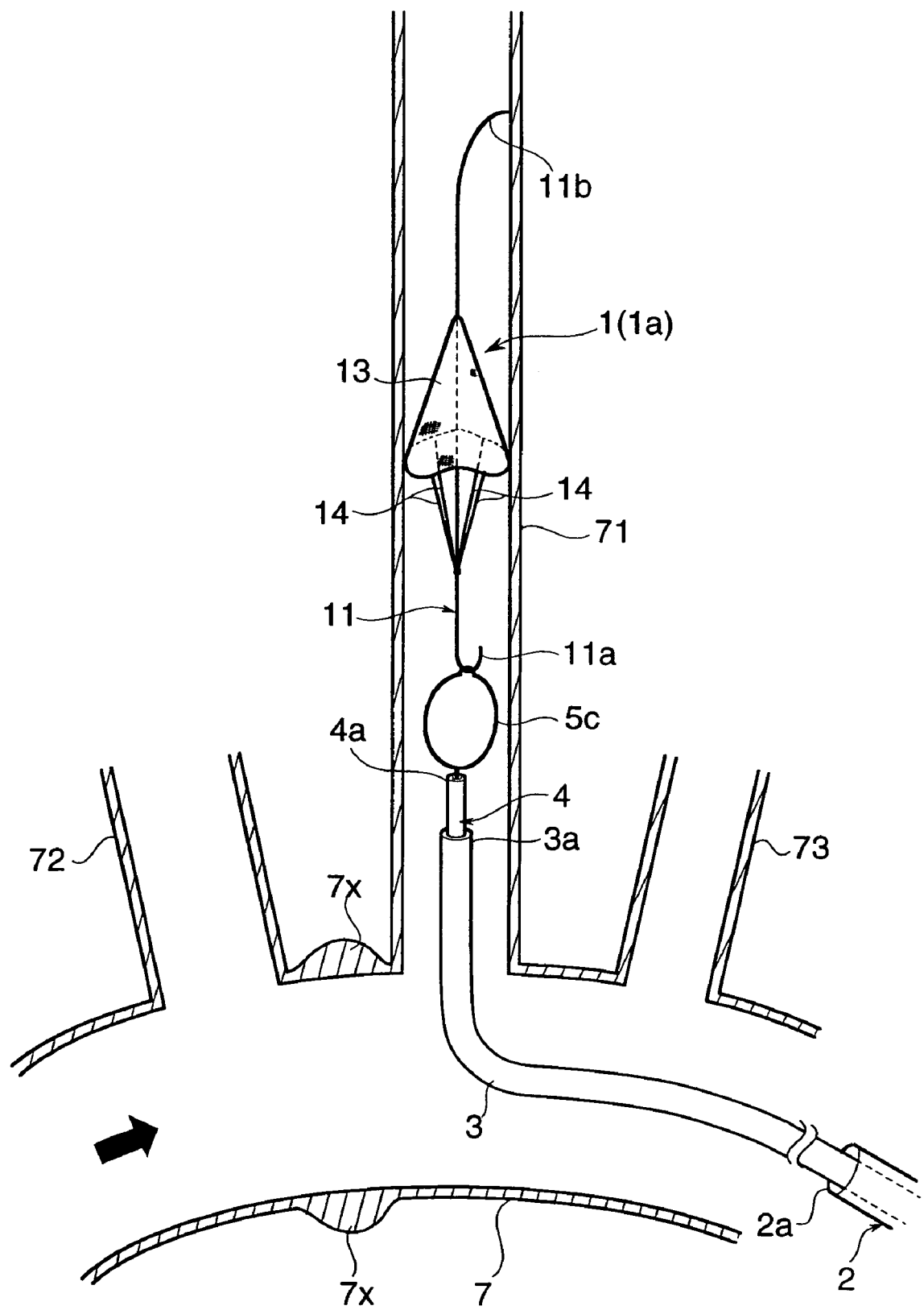
FIG. 12 is an explanatory view showing a transport process to arrange the alienated thrombus capture device at the predetermined portion of blood vessel.
Figure 13:
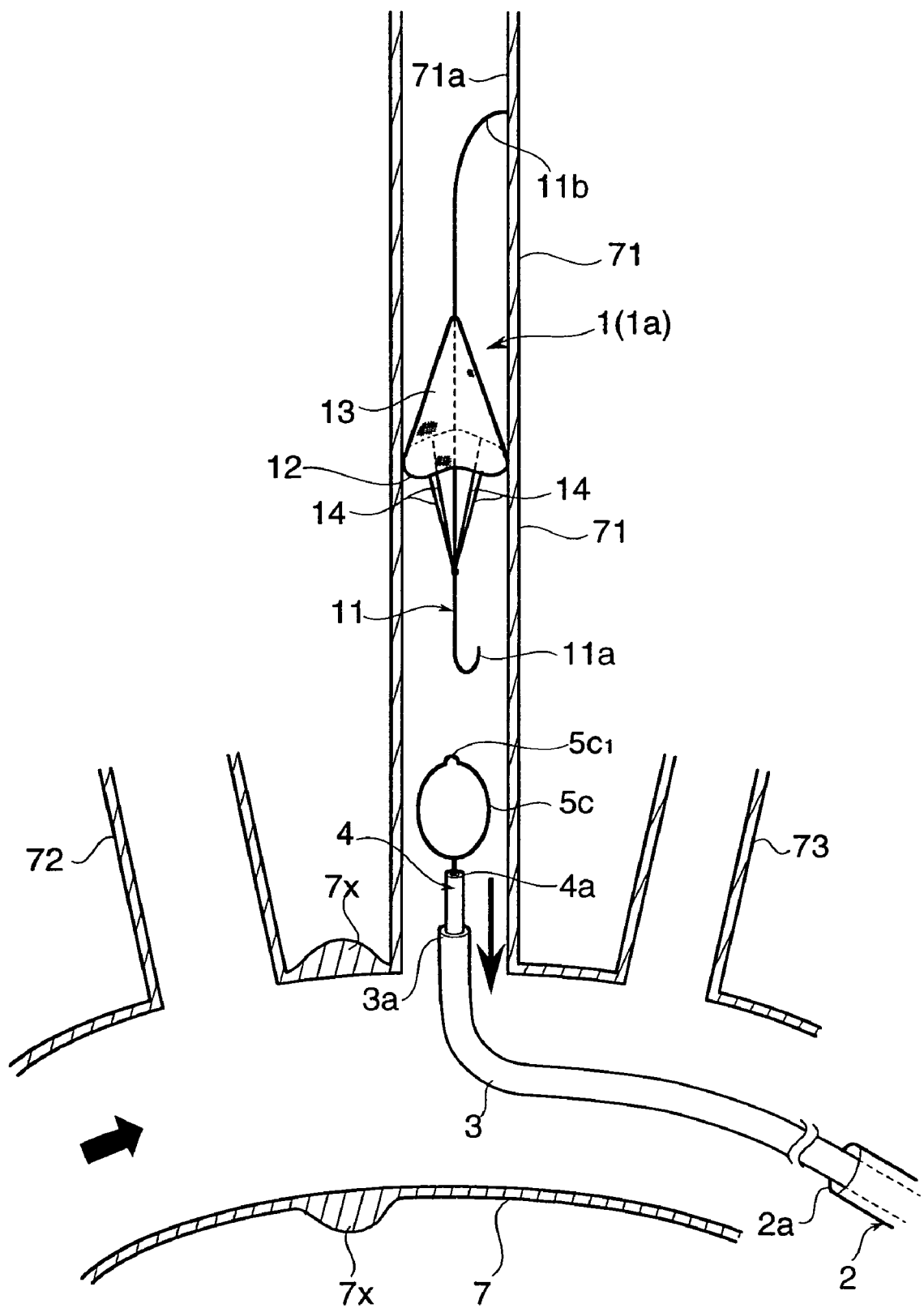
FIG. 13 is an explanatory view showing a state that the alienated thrombus capture device is arranged at the predetermined portion of blood vessel.

From the above-mentioned state shown in FIG. 9 and FIG. 10, the first catheter 3 alone is pulled back into the sheath 2 as shown in FIG. 11 until the distal end portion 3a reaches the distal end of the second catheter 4 or the distal end portion 3a passes a little over the distal end of the second catheter 4, and then the whole of the ring portion 12 is exposed in the blood vessel 71, and the ring portion 12 starts to spread due to resilient restoration force from the folded state 1b. In this state, since the proximal end portion side of the support linear member portions 14 are still in the second catheter 4, the ring portion 12 is not spread completely. Then, the wire 5 is loosened and the first catheter 3 is further pulled into the sheath 2, exposing the engaging portion 5c of the wire 5 and the whole of the alienated thrombus capture device 1 into the blood vessel 71 from the second catheter 4 as shown in FIG. 12. Then, the ring portion 12 is in a completely spread state 1a and is supported by the support linear member portions 14 having tensile force between the ring portion 12 and the stiffener portion 11. In case that a subtle adjustment of positioning is necessary for the alienated thrombus capture device 1, the wire 5 may be operated. Further, as shown in FIG. 13, the proximal end portion 5b of the wire 5 is operated so as to release engagement of the engaging portion 5c and the hook portion 11a, leaving the alienated thrombus capture device 1 at a position where the ring portion 12 spreads. The first catheter 3, the second catheter 4 and the wire 5 are enclosed into the sheath 2 and are further withdrawn out of the body in order not to disturb the operation of detaining the artificial blood vessel 8. The first catheter 3, the second catheter 4 and the wire 5 may be left in an appropriate blood vessel or the sheath 2 if they do not disturb the operation of detaining the artificial blood vessel 8.

Since the alienated thrombus capture device 1 left in the blood vessel 71 with the above procedure is arranged so that a diameter of the ring portion 12 is a little bigger than a bore diameter (in this case, about 8 mm) of the blood vessel 71, the ring portion 12 and the opening edge portion 13a of the bursiform portion 13 tightly attach to the inner wall 71a of the blood vessel 71 and are supported by the support linear member portions 14 stably while taking a posture in which a direction of the center axis 12n generally coincides with the direction of blood flow B.F. In addition, since the distal end of the guide portion 13 formed at the distal end portion of the stiffener portion 11 makes abutting contact with the inner wall 71a of the blood vessel 71, the alienated thrombus capture device 1 is difficult to incline. Further, since the ring portion 12 spreads in the blood vessel 71 in a slight wavy shape corresponding to the folded habit created beforehand, and is tightly attached to the inner wall 71a of the blood vessel 71, the ring portion 12 shrinks/spreads by following the pulse of the blood vessel 71 while keeping the tightly attached state. In other words, the ring portion 12 can be kept in the tightly attached state with the inner wall 71a of the blood vessel 71 and excessive load applied to the blood vessel 71 can be prevented.

Figure 14:
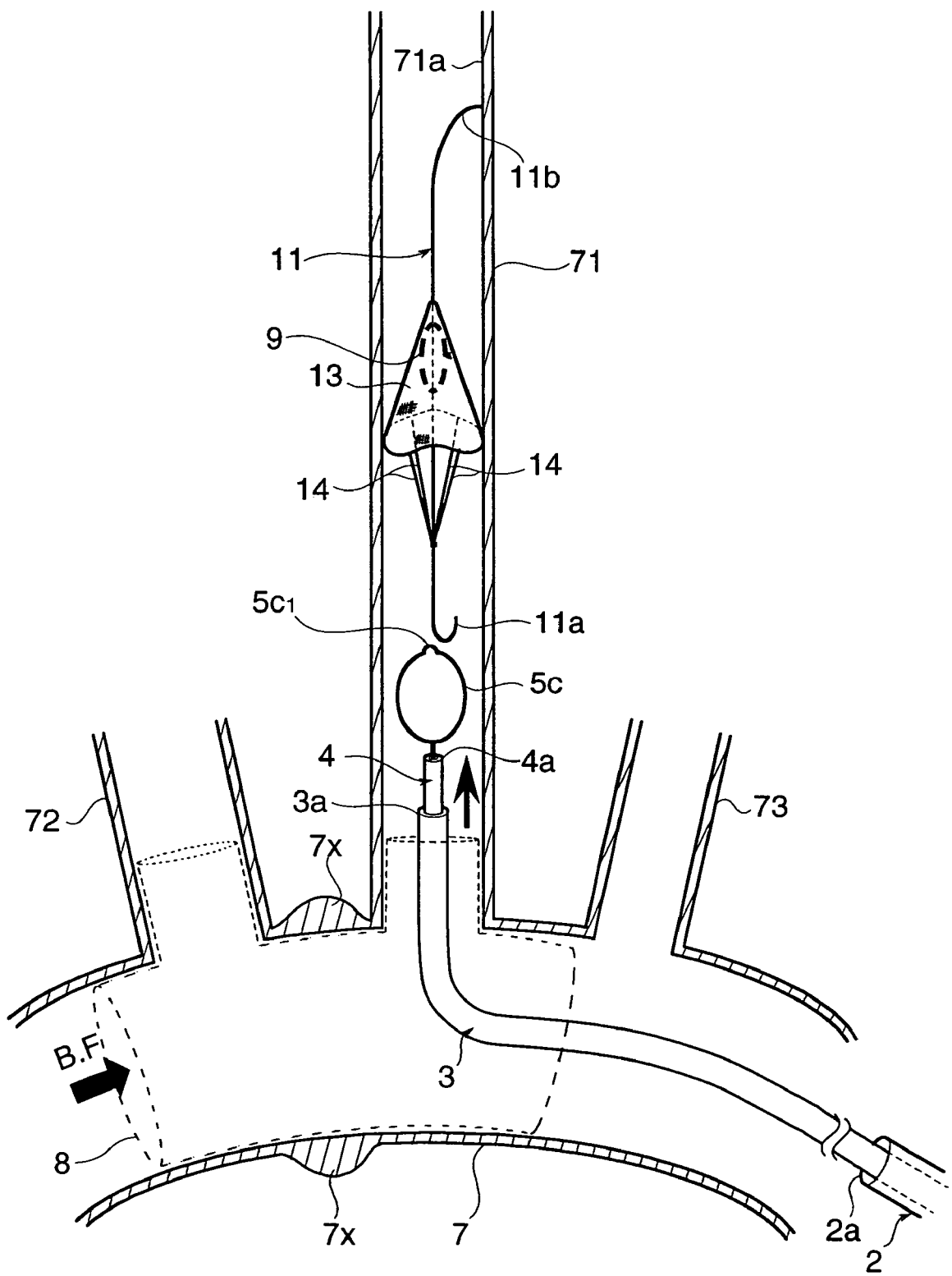
FIG. 14 is an explanatory view showing a transport process to retrieve the alienated thrombus capture device from the blood vessel.

As mentioned above, when the diseased portion 7x is treated with the artificial blood vessel 8 detained as shown in FIG. 14, a thrombus 9 alienated from the diseased portion 7x and flown to the left arteria carotis communis 71 located at a peripheral side is enclosed in the bursiform portion 13 of the alienated thrombus capture device 1. In this case, since the bursiform portion 13 is made of a meshed material, blood passes through the bursiform portion 13 easily and the thrombus 9 alone is filtered and captured. In order to retrieve the alienated thrombus capture device 1 that has caught the thrombus 9 with the above process from the blood vessel 71, the first catheter 3 is sent again to the blood vessel 71 through the sheath 2 until the distal end portion 4a of the second catheter 4 protrudes from the distal end portion 3a of the first catheter 3 and the distal end portion of the wire 5 protrudes from the distal end portion 4a of the second catheter 4 as shown in FIG. 14.

Figure 15:
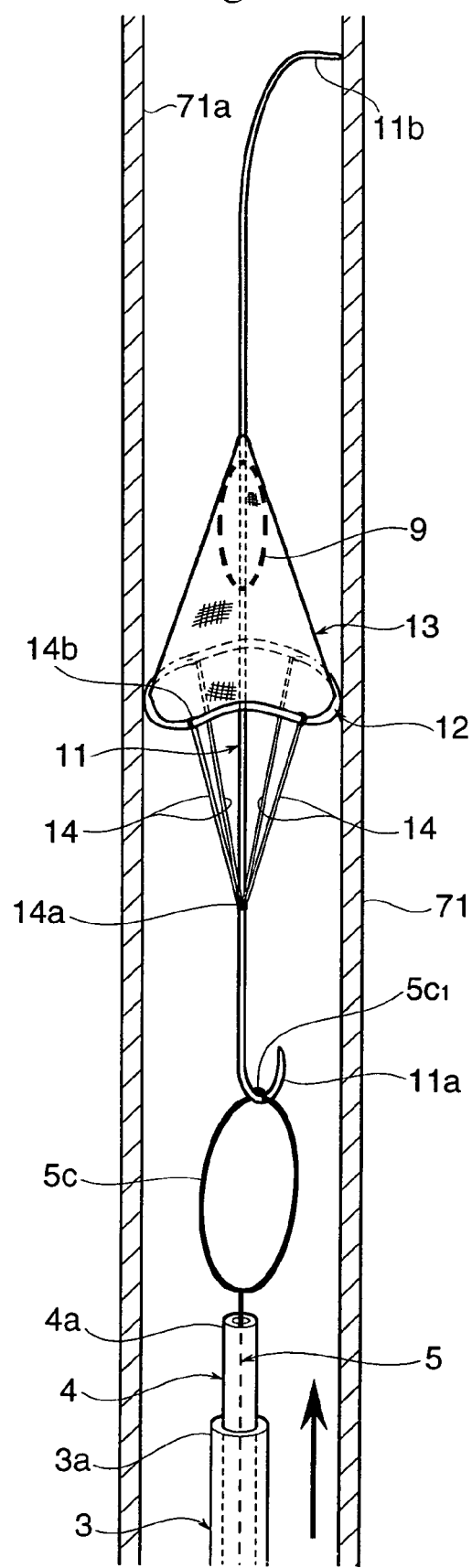
FIG. 15 is a magnified explanatory view of a principal portion in FIG. 14.
Figure 16:
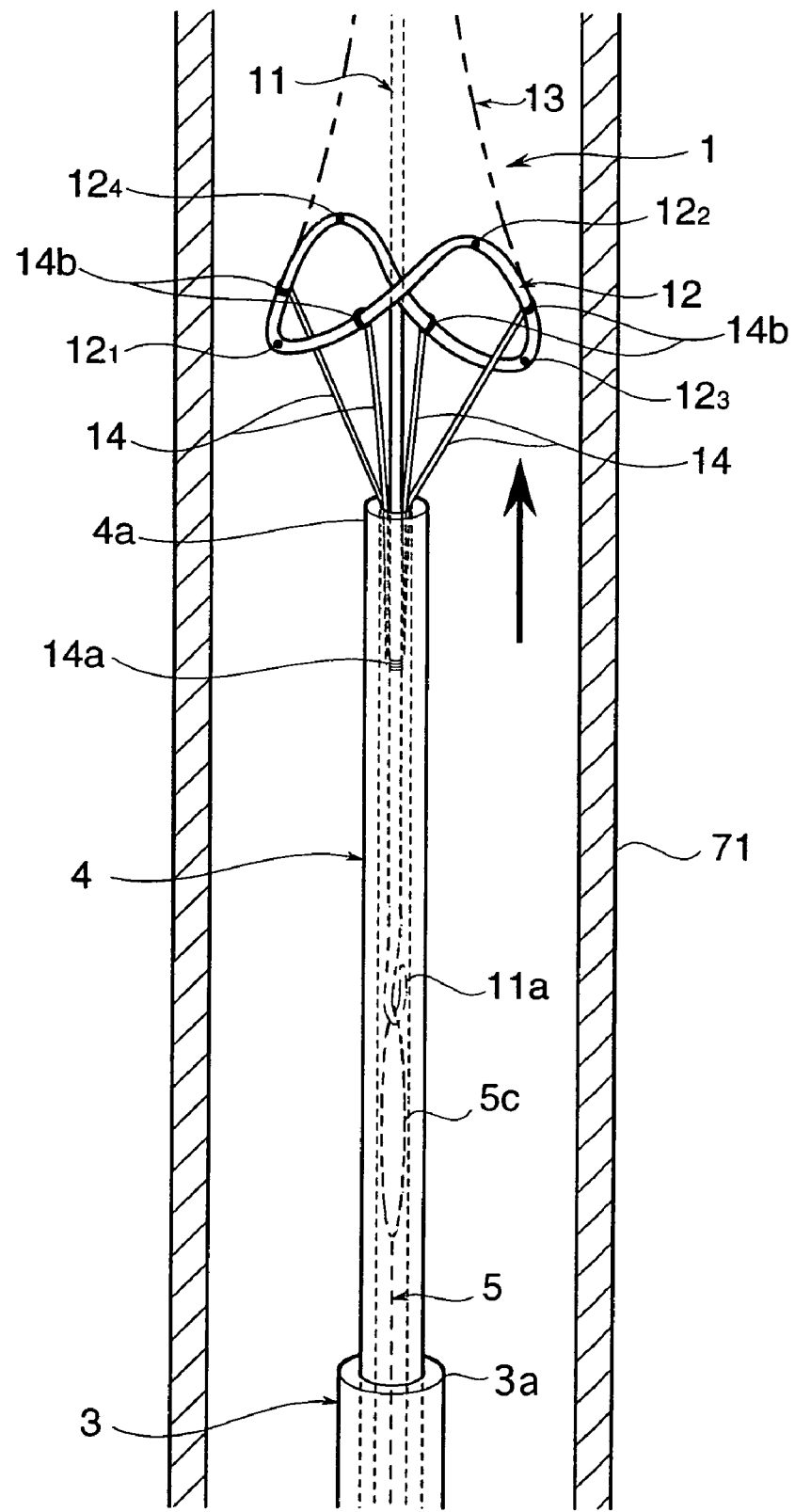
FIG. 16 is a magnified explanatory view showing a transport process to retrieve the alienated thrombus capture device from the blood vessel.
Figure 17:
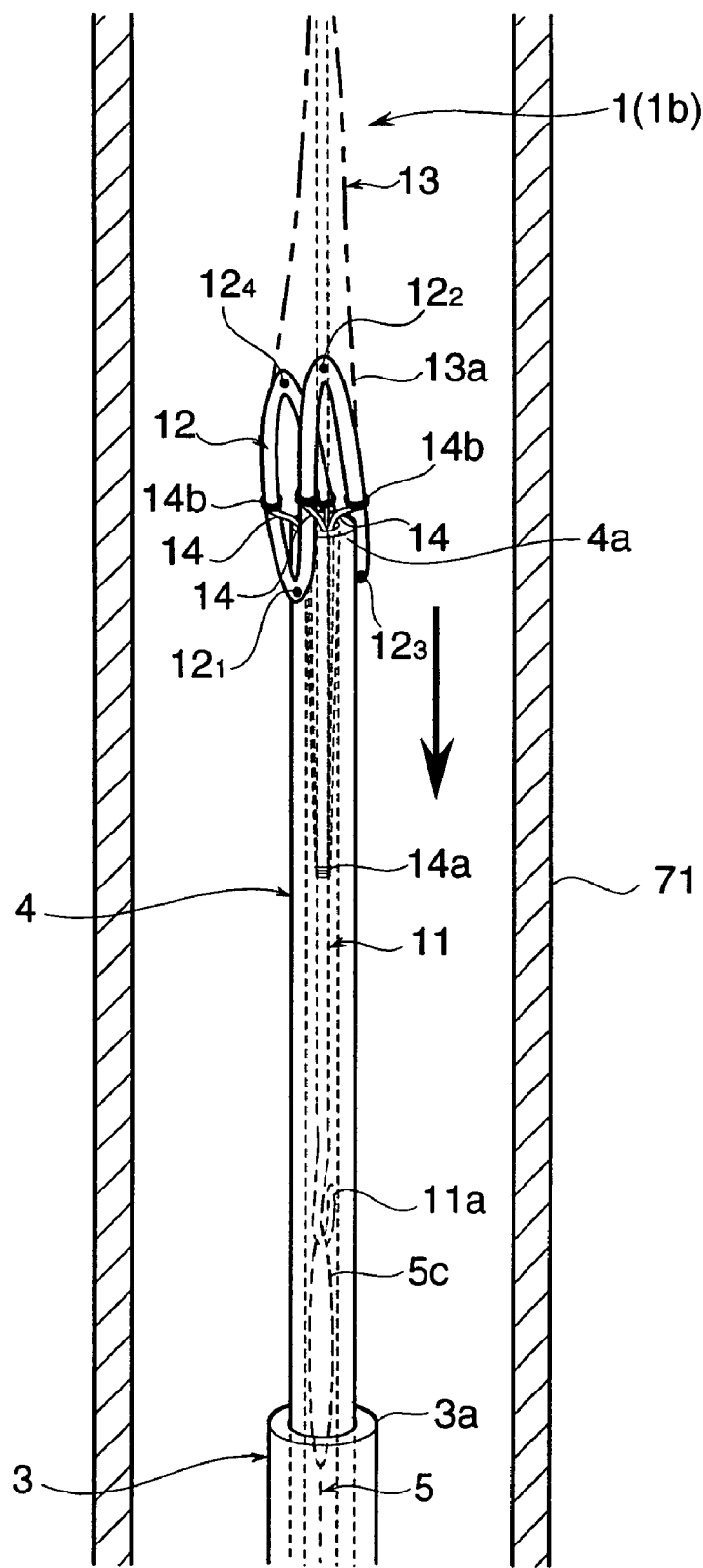
FIG. 17 is a magnified explanatory view showing a transport process to retrieve the alienated thrombus capture device from the blood vessel.

The following is a concrete explanation. First, the wire 5 is made to be in a movable state relative to the second catheter 4 and engages the engaging portion 5c of the wire 5 projecting from the distal end portion 4a of the second catheter 4 with the hook portion 11a of the stiffener portion 11 as shown in FIG. 15. Next, the second catheter 4 is further paid out toward a distal end direction so as to increase a projecting amount of the distal end portion 4a side of the second catheter 4 from the distal end portion 3a of the first catheter 3, as shown in FIG. 16. Then, the wire 5, the proximal end portion side of the stiffener portion 11 and the proximal end portion side of the support linear member portions 14 are enclosed inside the second catheter 4. When the support portion 14a of the support linear member portions 14 are enclosed inside the second catheter 4, each support linear member portion 14 is gradually bundled in a state having tensile force between the support portion 14b of the ring portion 12 and the distal end of the second catheter 4. As a result, the ring portion 12 is pulled toward the stiffener portion 11 side in a wavy shape with the dividing points $12_1$ and $12_3$ forming the bottoms of the valleys and the dividing points $12_2$ and $12_4$ forming the peaks of the chevrons due to tensile force of the support linear member portion 14. Accordingly, the opening edge portion 13a of the stiffener portion 13 is gradually closed. Next, the second catheter 4 is further paid out toward a direction of the distal end. Then, a pair of the dividing points $12_1$ and $12_3$ that form the bottoms of valleys of the ring portion 12 folded into the wavy form hold the distal end portion 4a of the second catheter 4 tightly, as shown in FIG. 17, and the alienated thrombus capture device 1 is in the generally completely folded state 1b. In other words, in this state, the opening edge portion 13a of the bursiform portion 13 is closed. Then the wire 5 is fixed to the second catheter 4 and a relative positional relation between the second catheter 4, the wire 5 and the alienated thrombus capture device 1 is kept generally constant.

Figure 18:
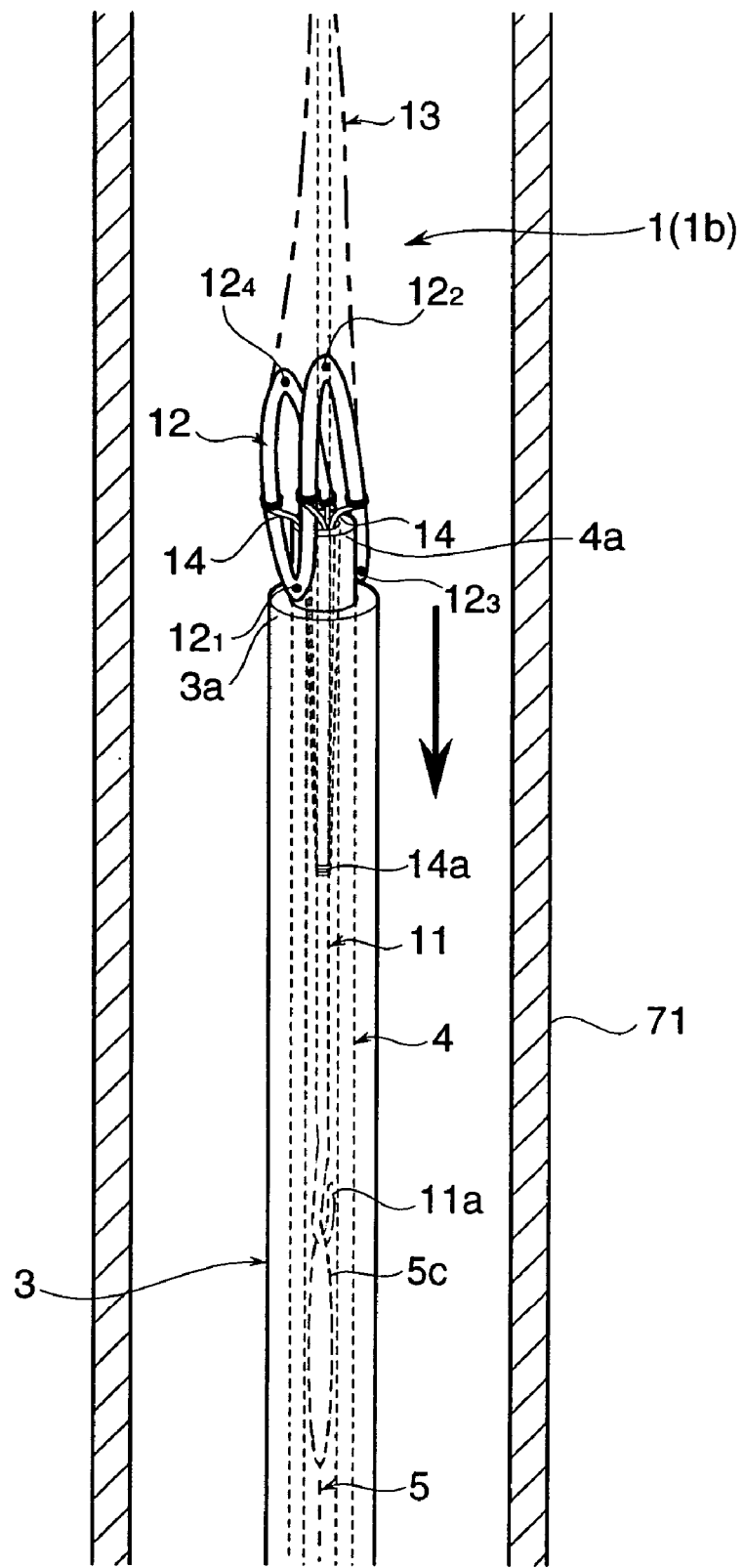
FIG. 18 is a magnified explanatory view showing a transport process to retrieve the alienated thrombus capture device from the blood vessel.

Further, as shown in FIG. 18, the first catheter 3 is paid out toward a distal end side, or the alienated thrombus capture device 1 is alternatively pulled toward the first catheter 3 side together with the wire 5 so as to make a pair of the dividing points $12_1$ and $12_3$ that form the bottoms of the valleys of the ring portion 12 be in abutting contact with the distal end of the first catheter 3. Accordingly, a closed state of the opening edge portion 13a of the bursiform portion 13 can be made more stable. In this case, in order to retrieve the alienated thrombus capture device 1 smoothly, it is preferable not to form a step between the ring portion 12 that tightly holds the second catheter 4 and the first catheter 3 along a direction of the radius of the first catheter 3. Then, the first catheter 3, the second catheter 4, the wire 5 and the alienated thrombus capture device 1 are pulled out of the body through the sheath 2 after the captured thrombus 9 is made not escape the bursiform portion 13. Thus, the alienated thrombus capture device 1 is retrieved together with the captured thrombus 9.

Figure 19:
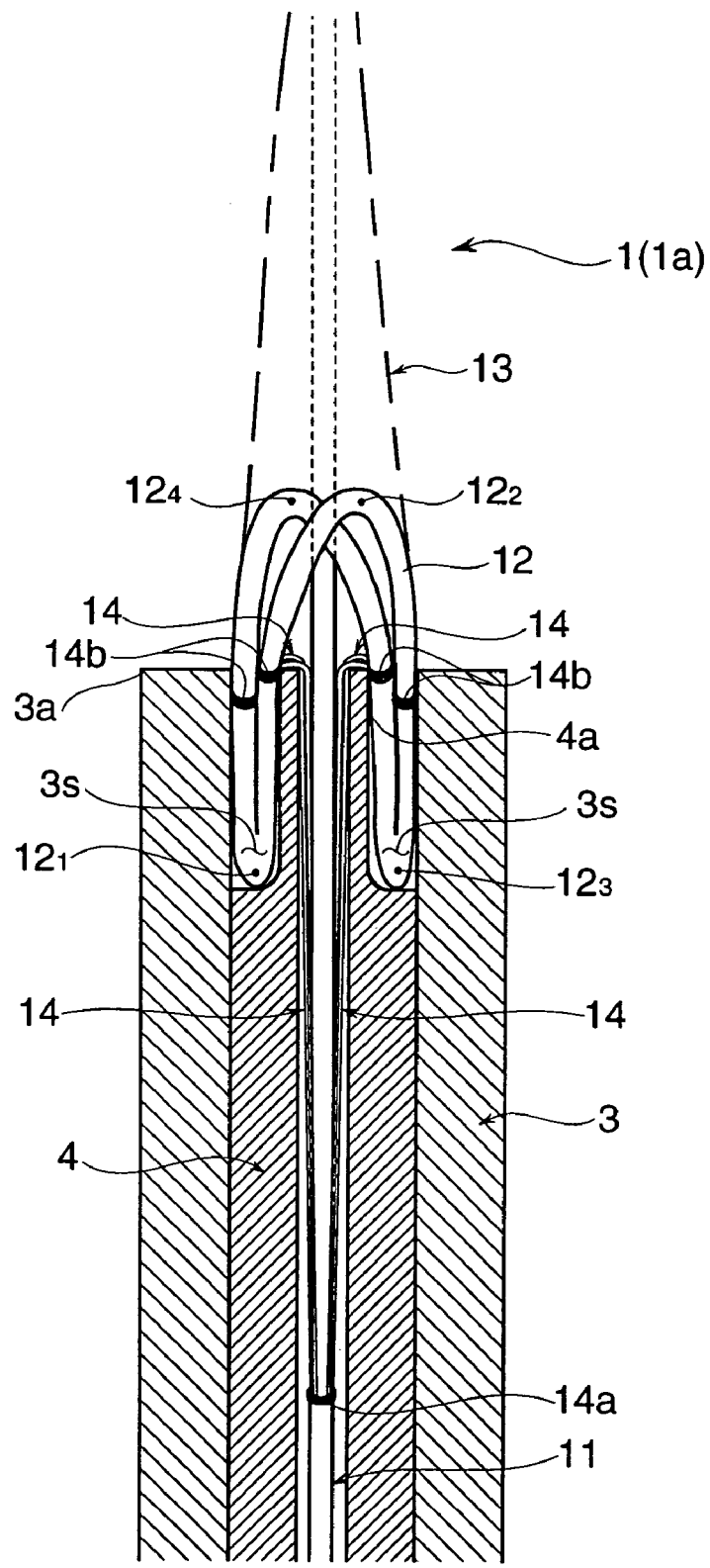
FIG. 19 is a magnified longitudinal cross-sectional view showing a modified form of a transport process to retrieve the alienated thrombus capture device from the blood vessel.
Figure 20:
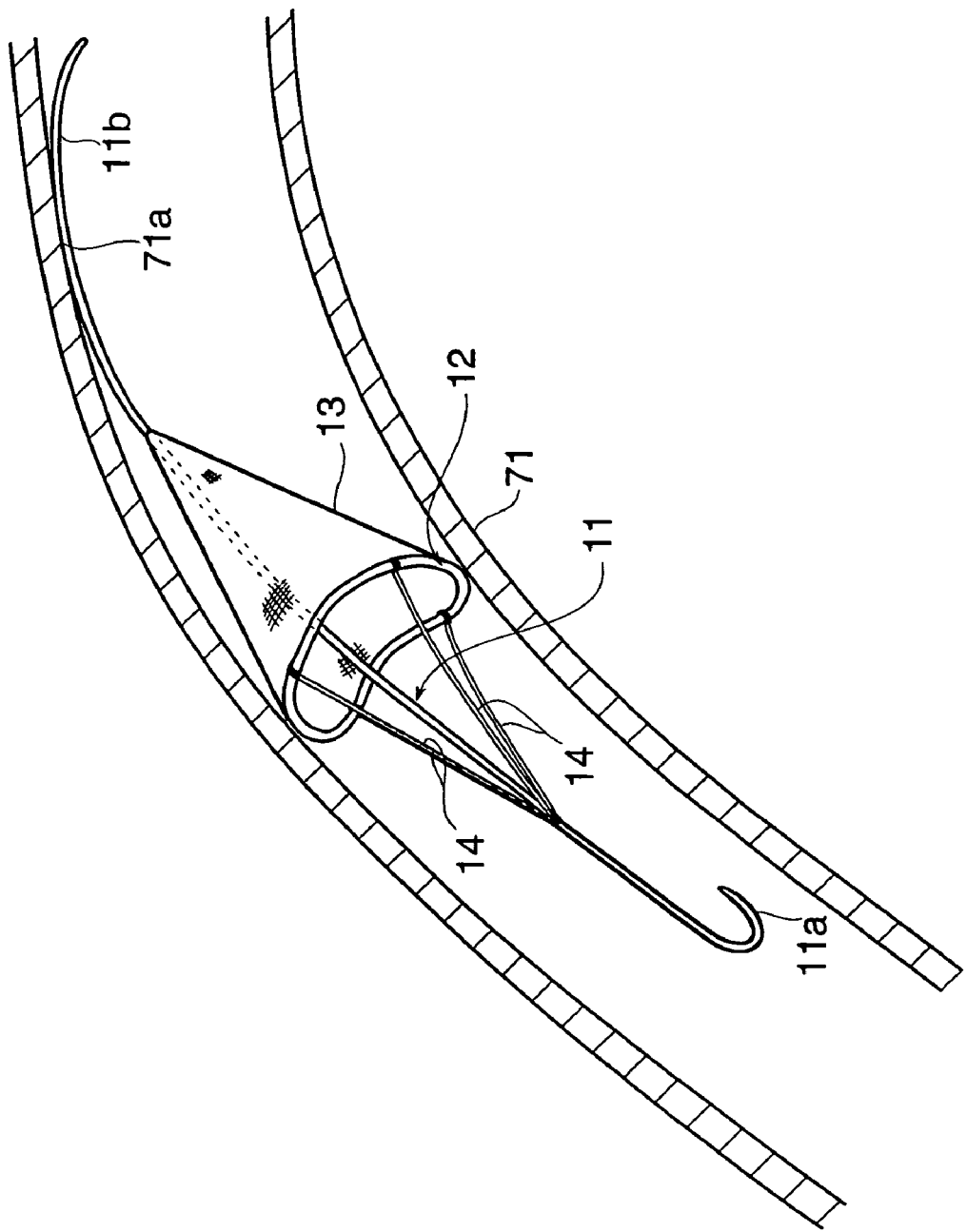
FIG. 20 is an explanatory view showing the alienated thrombus capture device arranged at a bent portion in the blood vessel.

In order to ensure the closed state of the opening edge portion 13a of the bursiform portion 13 of the alienated thrombus capture device 1 that has caught the alienated thrombus 9, it is preferable that, for example as shown in FIG. 19, an outer diameter of the distal end portion 4a of the second catheter 4 is made a little thinner than that of the proximal end portion of the second catheter 4 to form a small gap 3s between the outer diameter of the second catheter 4 and a bore diameter of the first catheter 3, so that a portion including a pair of the dividing points $12_1$ and $12_3$ that form the bottoms of valleys of the folded ring portion 12 can be enclosed in the gap 3s. In addition, alternatively, although not shown in drawings, a diameter of the distal end portion 3a of the first catheter 3 may be made thicker than that of the proximal end portion of the first catheter 3 to form a gap like the above between the first catheter 3 and the outer diameter of the second catheter 4, so that the dividing points $12_1$ and $12_3$ of the ring portion 12 and a portion around the dividing points $12_1$ and $12_3$ can be enclosed in the gap. With this arrangement, since the ring portion 12 is pushed against the bore diameter of the first catheter 3 in a folded state, it is possible to effectively prevent the opening edge portion 13a of the bursiform portion 13 from opening.

In the above explained case, that the alienated thrombus capture device 1 is arranged in a relatively straight portion in the blood vessel 71. However, the alienated thrombus capture device 1 can be preferably arranged in, for example, a curved portion in the blood vessel 71. In this case, the guide portion 11b located at the distal end portion side of the stiffener portion 11 makes abutting contact with the inner wall 71a of the blood vessel 71 in a bowed state along a curved blood vessel 71 and supports other portions. In other words, the support linear member portion 14 mounted on the bowed stiffener portion 11 supports the ring portion 12 in a posture wherein a direction of an axial center of the ring portion 12 generally coincides with a direction of a blood flow with the support linear member portions 14 being located on the outer side of the curved portion in the blood vessel 71 in a tensed state and with the support linear member portions 14 being located on the inner side of the curved portion in an appropriately bowed state. As a result, it is possible to capture the thrombus surely in a curved blood vessel 71 by the use of the alienated thrombus capture device 1.

The alienated thrombus capture device 1 of this embodiment can be transported by the use of a transport device having an arrangement different from the above-mentioned transport device A.

Figure 21:
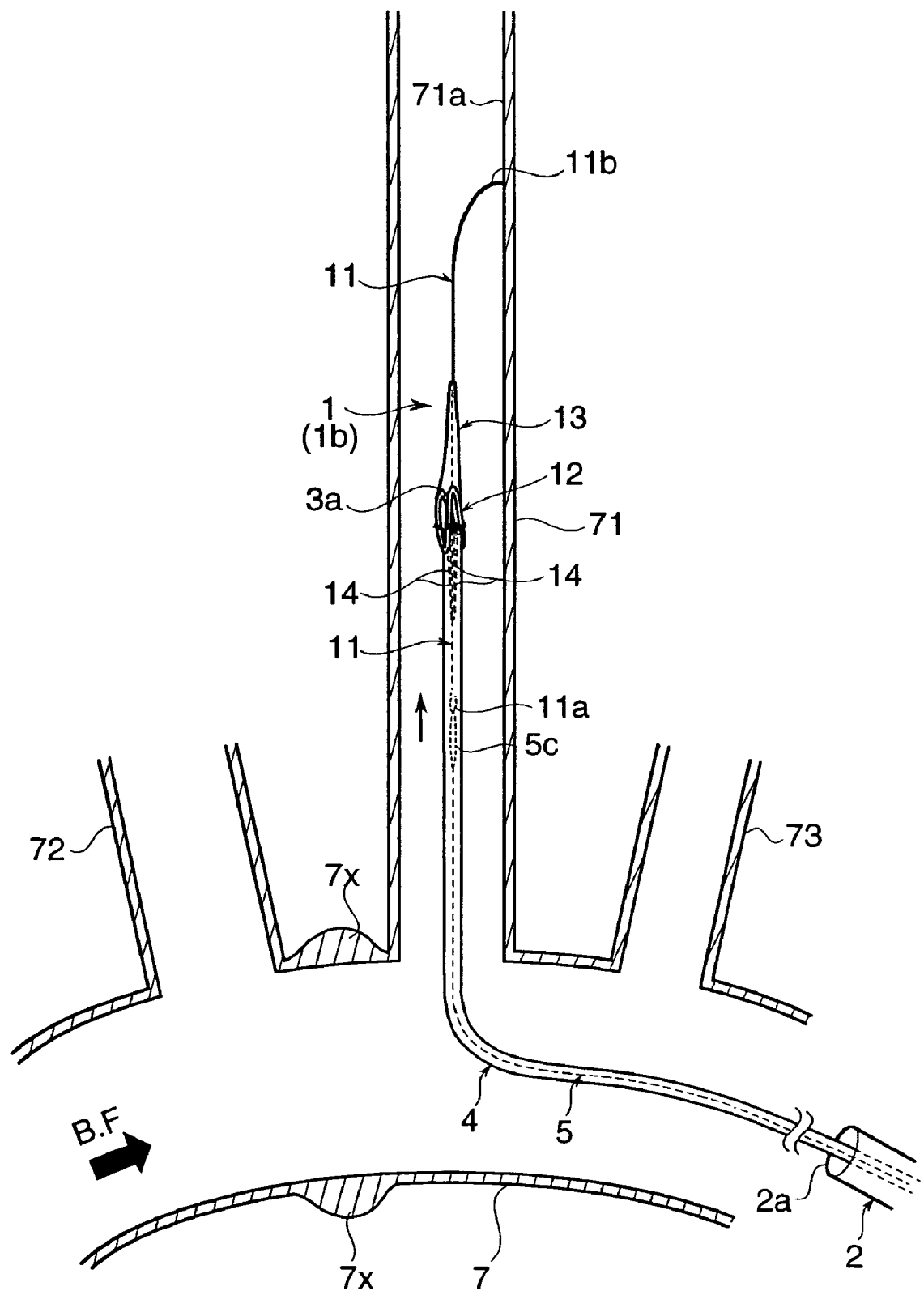
FIG. 21 is an explanatory view showing a transport process to arrange the alienated thrombus capture device at a predetermined portion in a blood vessel by a modified form of the transport device.
Figure 22:
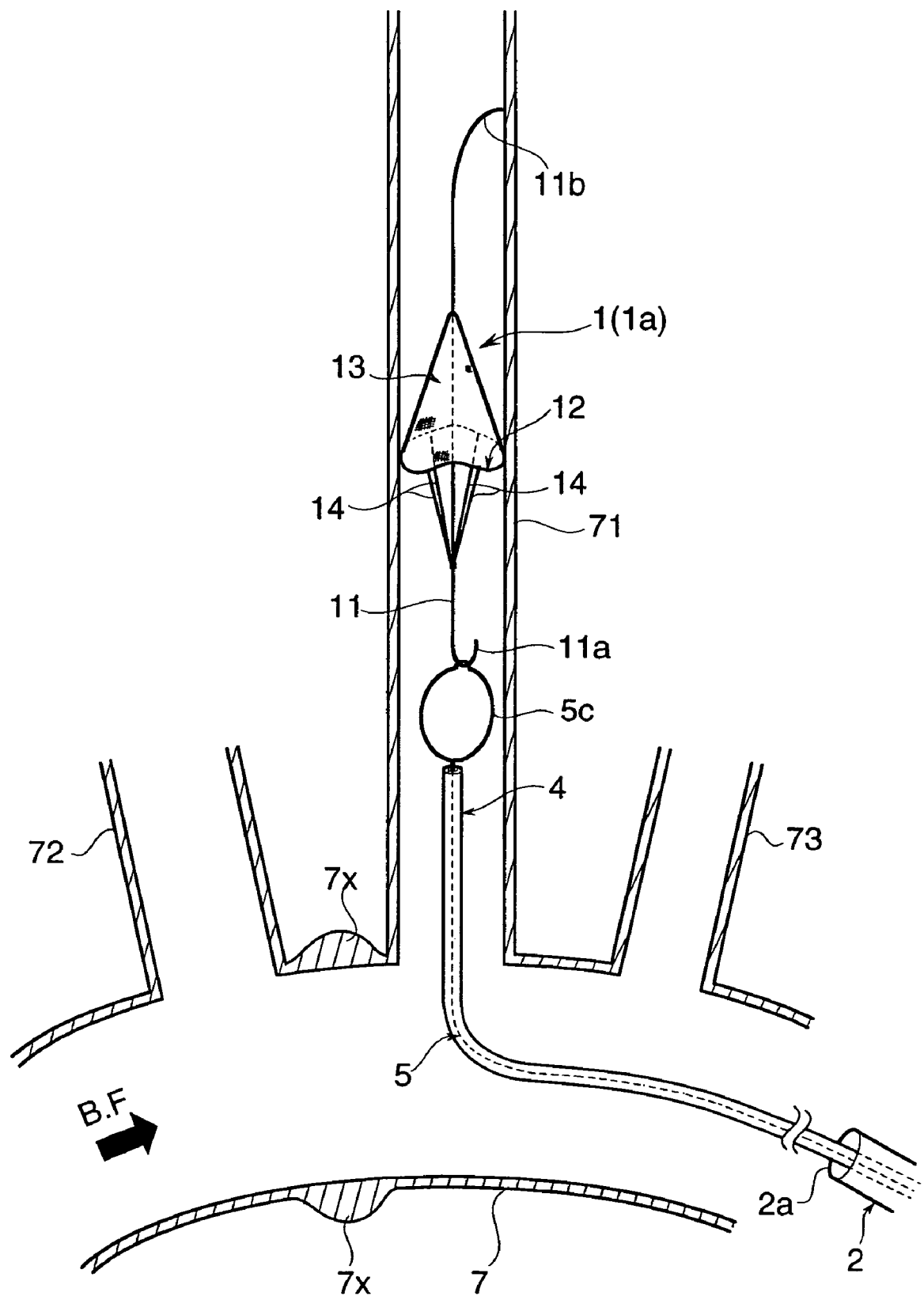
FIG. 22 is an explanatory view showing the alienated thrombus capture device arranged in the blood vessel by the transport device of the modified form.

For example, the transport device shown in FIG. 21 has the same arrangement as that of the transport device A except that the first catheter 3 is not used. More concretely, the alienated thrombus capture device 1 is folded at the distal end portion 4a of the second catheter 4 as shown in FIG. 6 by pulling the wire 5 in the second catheter 4 and with this state kept, the wire 5 is fixed to the second catheter 4. Then, the alienated thrombus capture device 1 is inserted into the sheath 2 with a relative positional relationship between the second catheter 4 and the wire 5 kept generally constant. In this case, if the distal end of the second catheter 4 is arranged to make abutting contact with a portion where four support linear member portions 14 are pulled into the second catheter 4 when gathered and bundled, it is possible to transport the alienated thrombus capture device 1 with ease. Next, as shown in FIG. 21, the second catheter 4 is paid out to directly expose the distal end portion 4a inside the blood vessel 71 through the distal end portion 2a of the sheath 2, so that the alienated thrombus capture device 1 is transported to a predetermined position. At this position, a fixed state of the wire 5 to the second catheter 4 is released, and the second catheter 4 alone is pulled back as shown by the arrow in FIG. 21, so as to expose the engaging portion 5c of the wire 5 inside the blood vessel 71 as shown in FIG. 22. Then, the engaged state of the engaging portion 5c and the hook portion 11a are released by operating the proximal end portion 5b of the wire 5.

Figure 23:
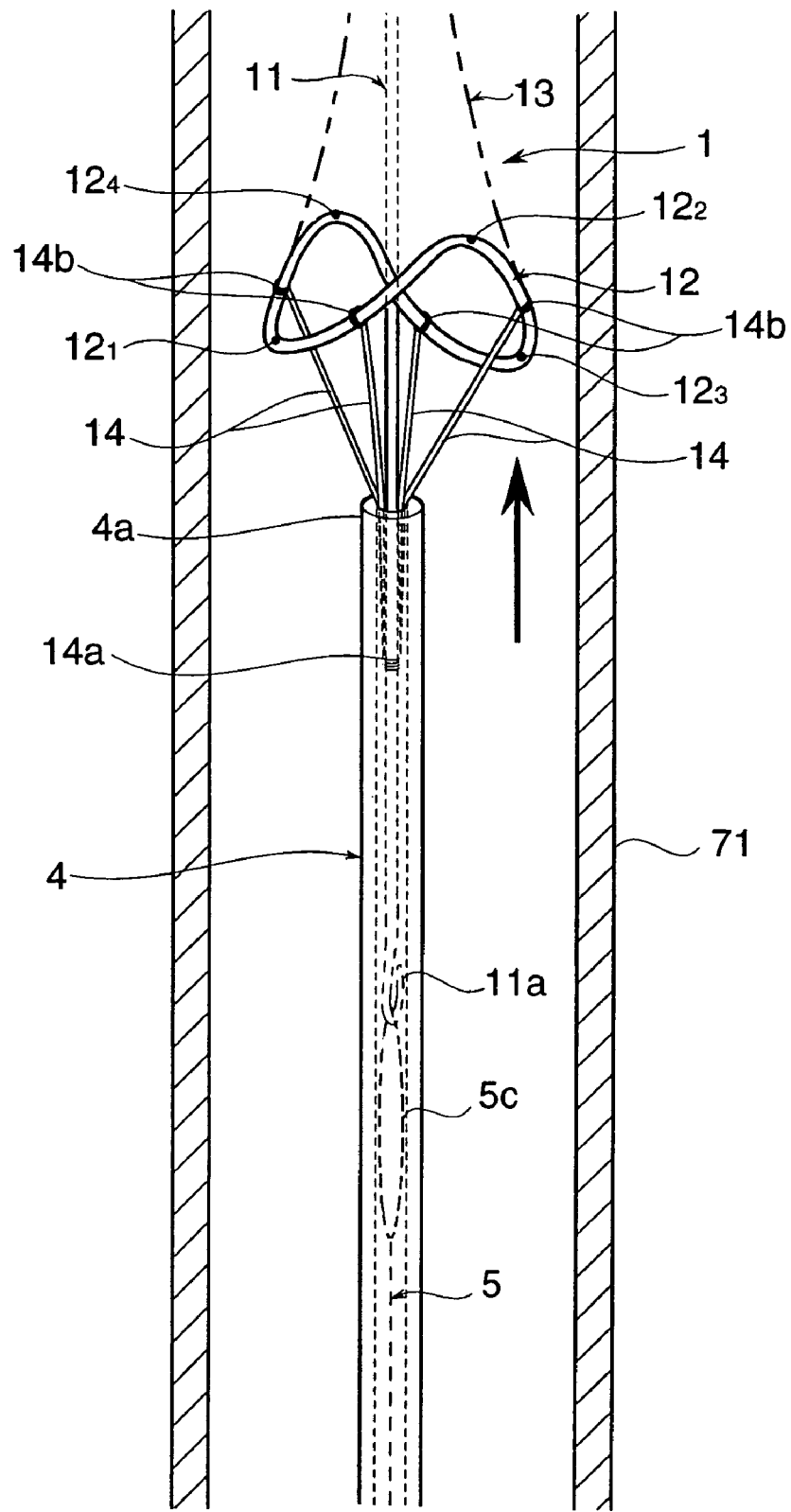
FIG. 23 is a magnified explanatory view of a principal portion of the alienated thrombus capture device showing a transport process to retrieve the alienated thrombus capture device by the user of the transport device in accordance with the modified form.
Figure 24:
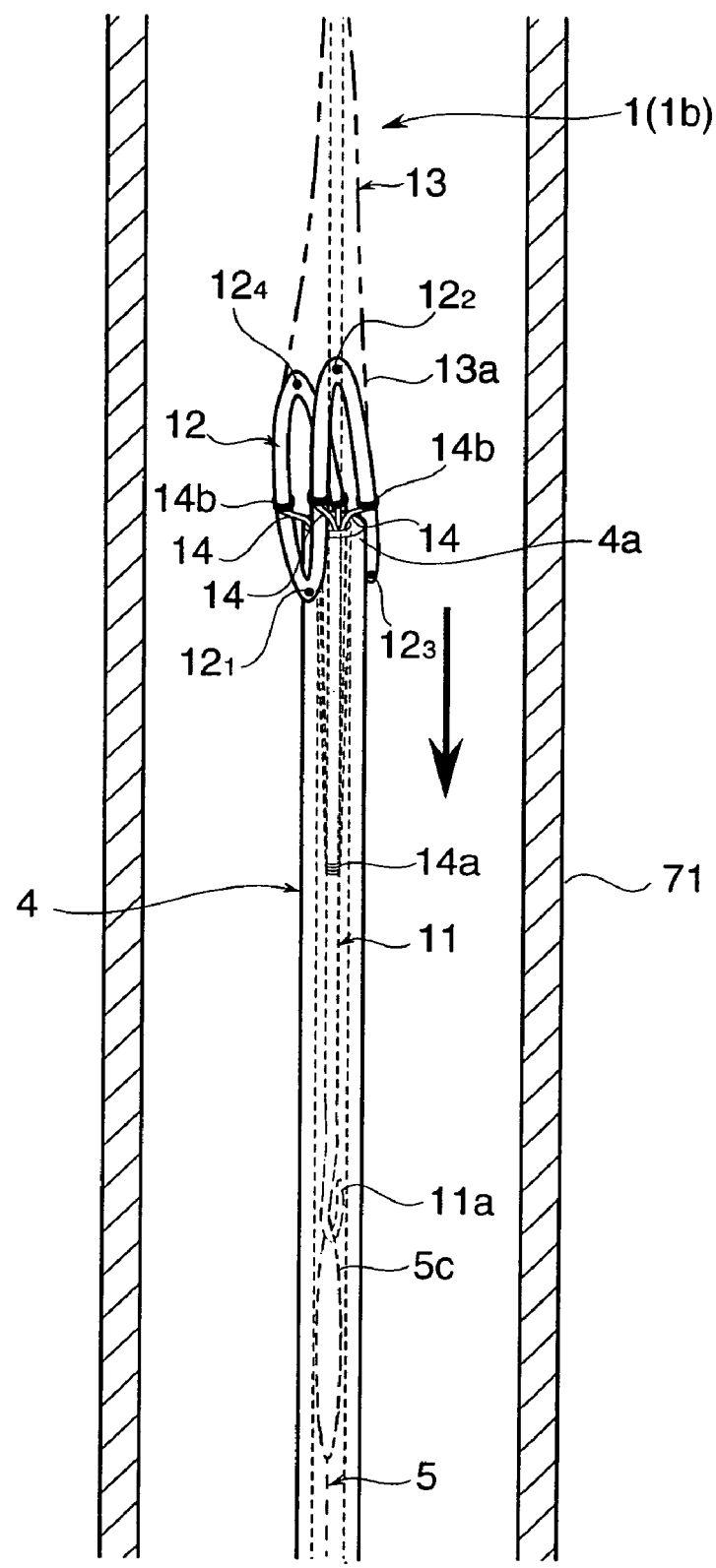
FIG. 24 is a magnified explanatory view showing the retrieval process.

In addition, like the above, the alienated thrombus capture device 1 arranged in the blood vessel 71 can be retrieved without using the first catheter 3. In other words, like the case shown in FIG. 15, the engaging portion 5c of the wire 5 extending from the distal end portion 4a of the second catheter 4 is hooked to the hook portion 11a of the alienated thrombus capture device 1, and the proximal end portion 5b of the wire 5 is pulled so as to draw the engaging portion 5c, the proximal end portion side of the stiffener portion 11 and the proximal end portion side of the support linear member portion 14 into the second catheter 4 as shown in FIG. 23. As a result, the ring portion 12 is folded into a wavy shape by tensile force of the support linear member portion 14. The wire 5 is further pulled, so that the dividing points $12_1$ and $12_3$ that form the bottoms of the valleys of the ring portion 12 tightly hold the distal end portion 4a of the second catheter 4 as shown in FIG. 24. With this state, the opening edge portion 13a of the bursiform portion 13 is closed. Next, the wire 5 is fixed to the second catheter 4 with a fixing member, not shown in drawings, so as to keep a relative positional relationship between the second catheter 4, the wire 5 and the alienated thrombus capture device 1 generally constant. Then, the second catheter 4, the wire 5 and the alienated thrombus capture device 1 are drawn into the sheath 2 at once so as to retrieve the alienated thrombus capture device 1.

Figure 25:
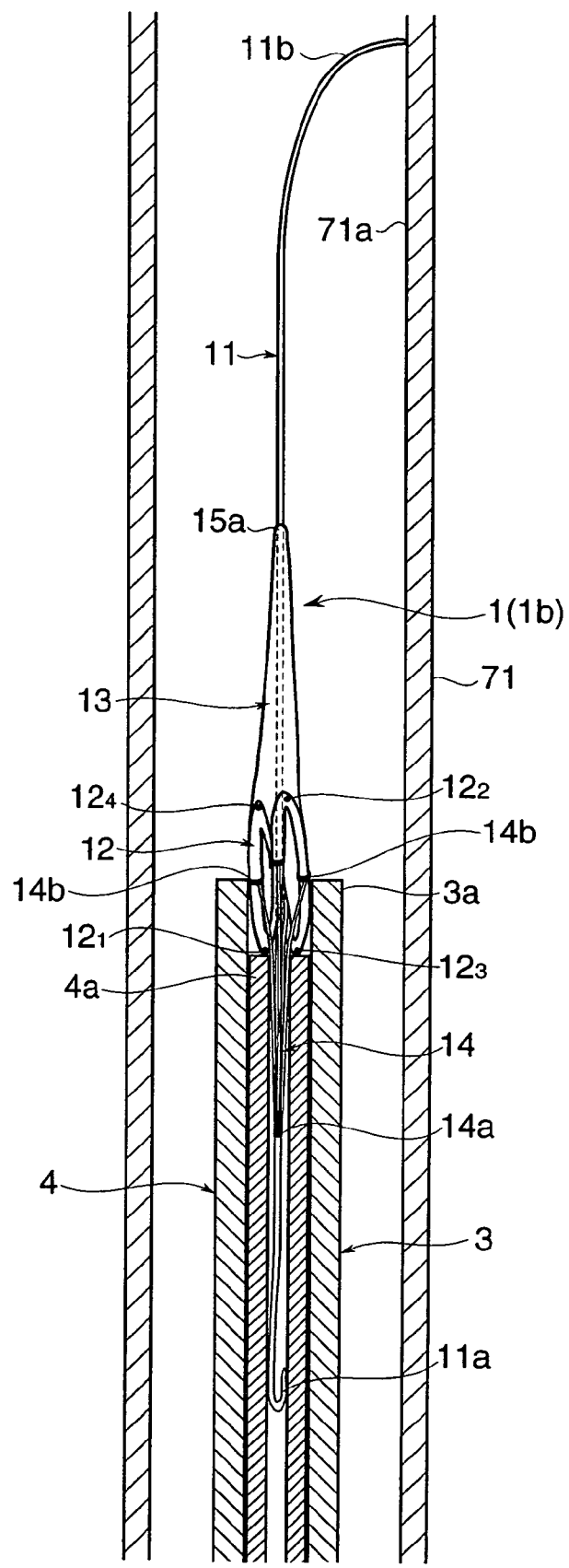
FIG. 25 is an explanatory view showing a transport process to arrange the alienated thrombus capture device at a predetermined portion in a blood vessel by the use of a transport device in accordance with a modified form of the embodiment.

Further, it is possible to pay out the alienated thrombus capture device 1 into the blood vessel 71 without using the wire 5. In this case, the alienated thrombus capture device 1 is inserted into the proximal end portion 3b of the first catheter 3 through the connector 31 with the ring portion 12 pushed to fold by a finger. Then, the dividing points $12_1$ and $12_3$ that form the bottoms of the valleys of the ring portion 12 that is folded into a wavy shape as shown in FIG. 25 are pushed from the proximal end side with the distal end of the second catheter 4. Thus, the alienated thrombus capture device 1 can be transported to a distal end side of the first catheter 3. In this case, it is preferable that the proximal end portion side of the stiffener portion 11 and the proximal end portion side of the support linear member portion 14 are inserted into the distal end portion 4b of the second catheter 4. When the pushed alienated thrombus capture device 1 reaches the distal end portion of the first catheter 3, the alienated thrombus capture device 1 is pushed by the second catheter 4 and is released from the first catheter 3 to the inside of the blood vessel 71 by pulling back the first catheter 3 alone. The alienated thrombus capture device 1 released from the first catheter 3 is restored to a spread state by elastic restoration force of the ring portion 12 at the released position. In this case, the second catheter 4 is not necessarily used as a member to transport the alienated thrombus capture device 1, and any solid flexible rod or linear shaped appropriate member, not shown in drawings, may be used.

Figure 26:
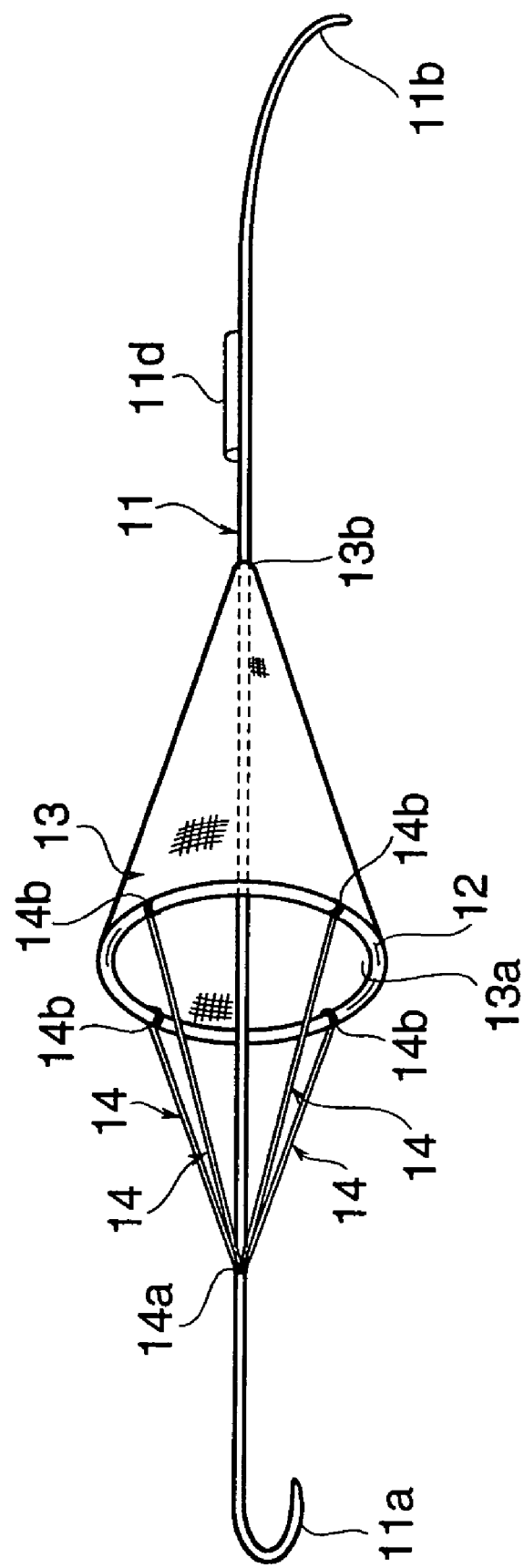
FIG. 26 is a perspective view showing the alienated thrombus capture device on which a guide tube is mounted.
Figure 27:
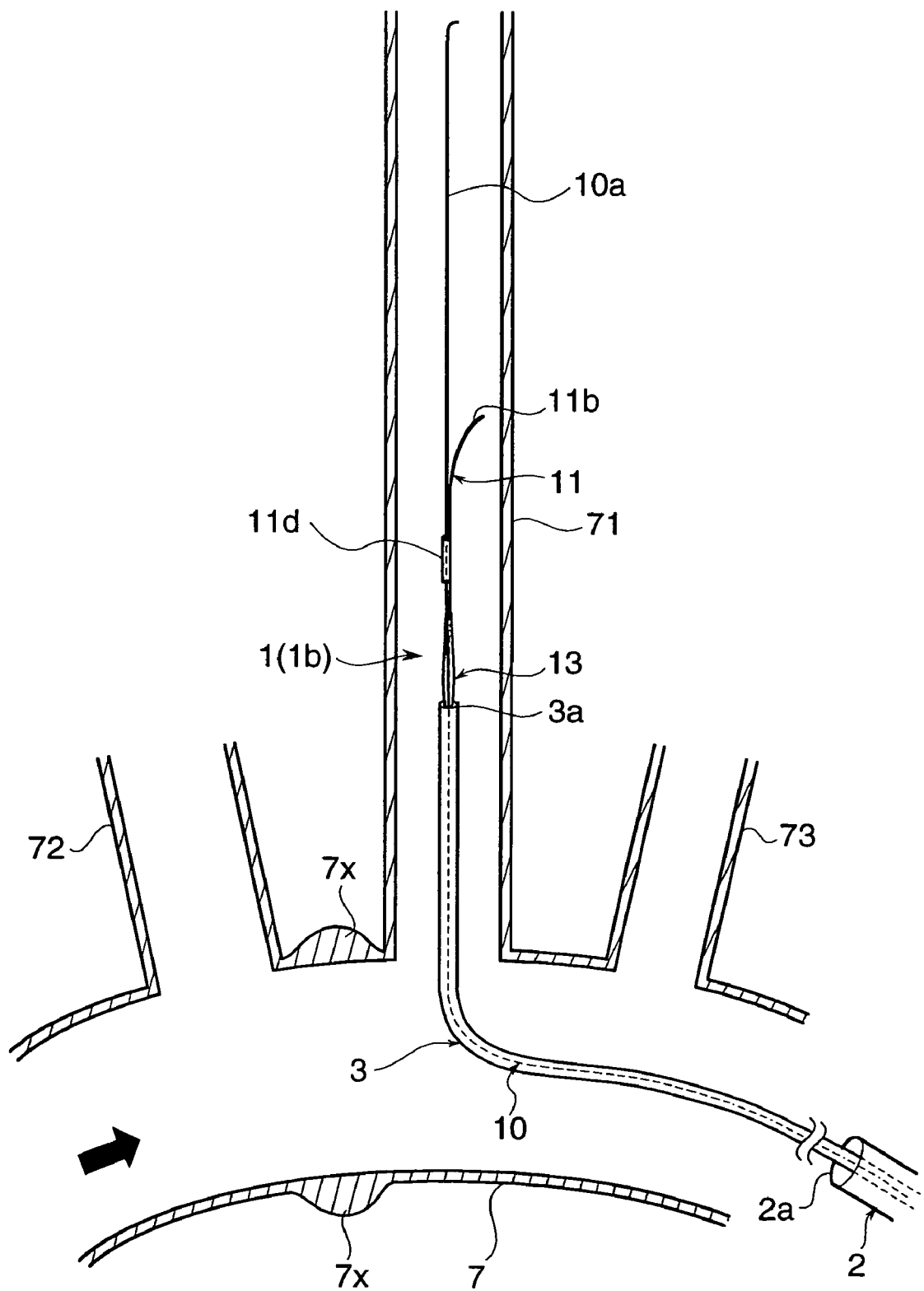
FIG. 27 is an explanatory view showing a process to transport the alienated thrombus capture device by the use of the guide tube and a guide wire.

Further, as shown in FIG. 26, an alienated thrombus capture device 1 having an arrangement wherein a small guide tube lid is mounted on a portion at the distal end portion side of the stiffener portion 11 may be used. In this case, a long guide wire 10 as shown in FIG. 27 is used in addition to the above-mentioned transport device A. The guide wire 10 is inserted into the second catheter 4 (omitted in FIG. 27) together with the wire 5 with its distal end portion 10a side inserted into the guide tube 11d along the stiffener portion 11. A proximal end portion, not shown in drawings, of the guide wire 10 is exposed to outside the body so as to be operated from outside the body through the sheath 2. The distal end portion 10a of the guide wire 10 is paid out to a portion where the alienated thrombus capture device 1 is to be arranged in a blood vessel or to upstream of the portion by operating the proximal end portion of the guide wire 10 so that the first catheter 3 reaches the portion and releases the alienated thrombus capture device 1 from the first catheter 3 so as to spread it. The above-mentioned arrangement and the method to transport the alienated thrombus capture device 1 is especially preferable for a case of transporting the alienated thrombus capture device 1 to a peripheral blood vessel away from an aorta.

An alienated thrombus capture device having other arrangement may be used in addition to the above. The same reference numerals will be given to the same components as that of the above-mentioned embodiments and a detailed explanation will be omitted.

Figure 28:
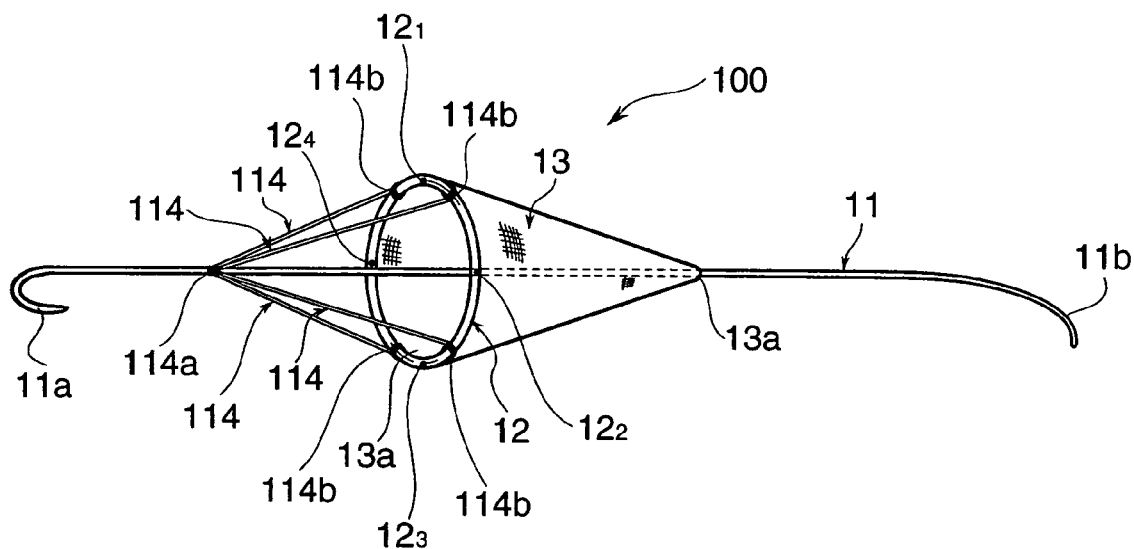
FIG. 28 is a perspective view showing a second embodiment of the alienated thrombus capture device.
Figure 29:
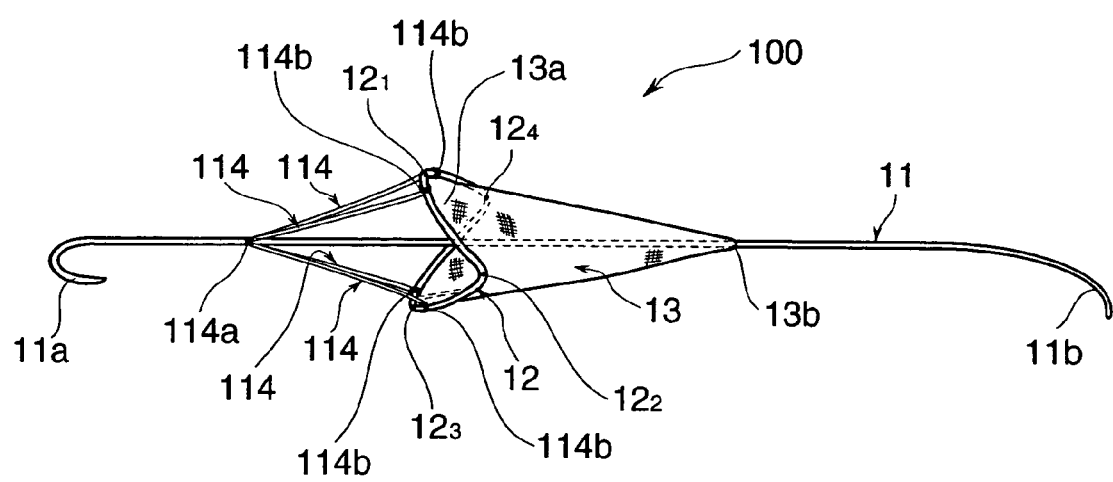
FIG. 29 is a perspective view showing a process to fold the alienated thrombus capture device in accordance with the second embodiment.

For example, an alienated thrombus capture device 100 shown in FIG. 28 has a similar fundamental arrangement to that of the above-mentioned embodiment, except that position of the support portions 114b of the support linear member portions 14 set on the ring portion 12 differs. More specifically, the dividing points $12_1$, $12_2$, $12_3$, $12_4$ of the ring portion 12 are set to generally quadrisect the circumference of the ring portion 12 like the above-mentioned embodiment and the support portions 114b arranged at positions to hold the dividing points $12_1$ and $12_3$ that form the bottoms of the valleys when the ring portion 12 is folded into a wavy shape are arranged not at middle points between each adjacent dividing points, but at positions close to the dividing points $12_1$, $12_3$ from middle points between each of the adjacent dividing points as shown in FIG. 29. In accordance with this arrangement, when the ring portion 12 is folded, an angle of the ring portion 12 that tightly holds the dividing points $12_1$ and $12_3$ that form the bottoms of the valleys facing to a proximal end side of the stiffener portion 11 can be made more acute, so as to narrow down an opening width of the bursiform portion 13 when folded, thereby improving reliability of preventing the captured thrombus from spilling out.

Figure 30:
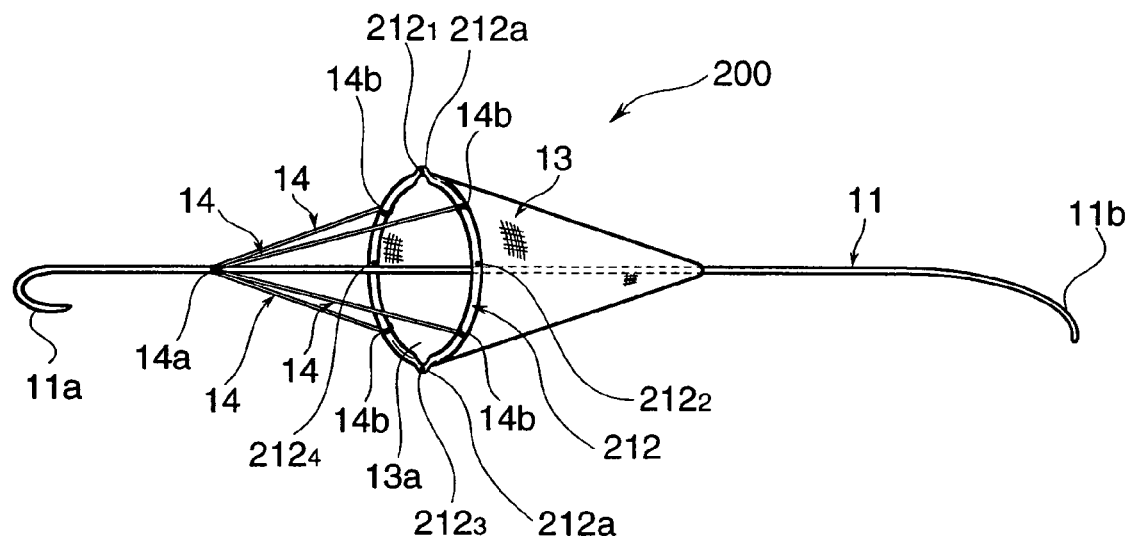
FIG. 30 is a perspective view showing a third embodiment of the alienated thrombus capture device.
Figure 31:
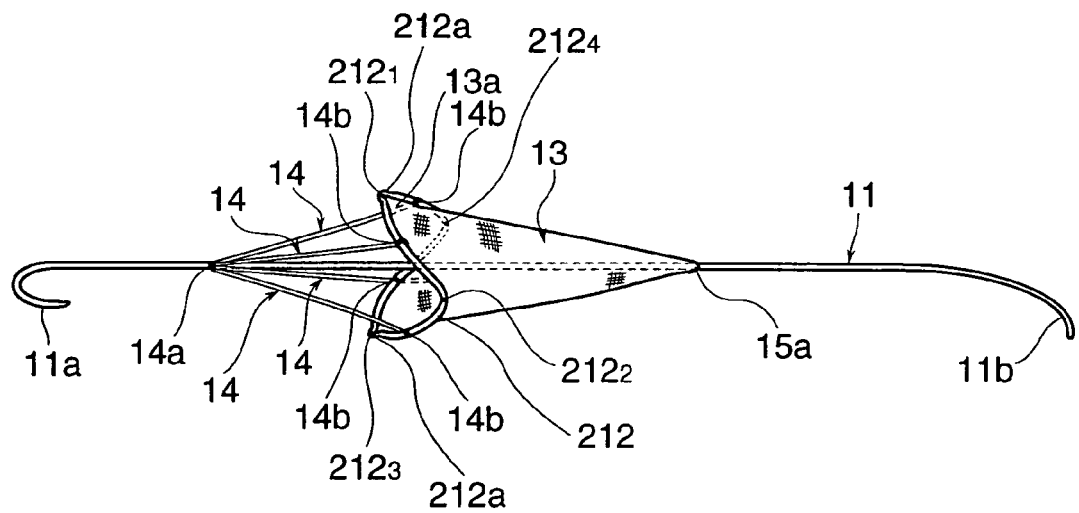
FIG. 31 is a perspective view showing a process to fold the alienated thrombus capture device in accordance with the third embodiment.

In addition, to the same purpose as that of the alienated thrombus capture device shown in FIG. 28 and FIG. 29, an alienated thrombus capture device 200 shown in FIG. 30 can be represented as an arrangement to narrow an opening width of the opening edge portion of the bursiform portion 13 effectively when the ring portion 212 is folded, in order to effectively prevent a captured thrombus from spilling out. The alienated thrombus capture device 200 has four dividing points $212_1$, $212_2$, $212_3$, $212_4$ on the ring portion 212 like the above embodiment, and is further provided with a pair of projecting portions 212a projecting toward a proximal end side of the stiffener portion 11 by curving or bending the ring portion 212 partially at the dividing points $212_1$ and $212_3$ that form the bottoms of the valleys facing the proximal end side of the stiffener portion 11 when the ring portion 212 is folded into a wavy shape as shown in FIG. 31. With this arrangement, it is possible to make a pair of the projecting portions 212a and 212a approach each other, namely the dividing points $212_1$ and $212_3$ approach each other when the ring portion 212 is generally completely folded, thereby an opening width of the opening edge portion 13a of the bursiform portion 13 is narrowed.

In addition, it is possible to fold the ring portion in an extremely compact size especially when the alienated thrombus capture device is retrieved from the blood vessel and to effectively prevent the captured thrombus from spilling out of the bursiform portion by devising an arrangement of the support linear member portion and a mode to support the support linear member portion by the ring portion.

Figure 32:
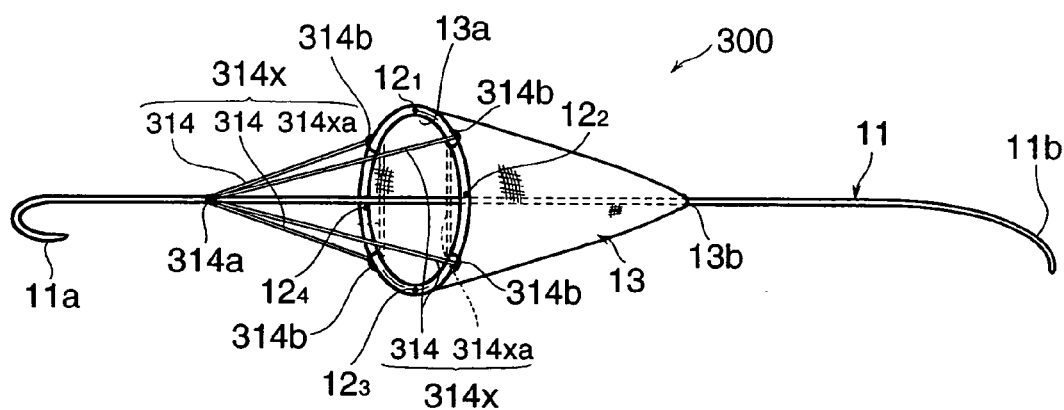
FIG. 32 is a perspective view showing a fourth embodiment of the alienated thrombus capture device.

For example, an alienated thrombus capture device 300 shown in FIG. 32 has four support linear member portions 314 like the above embodiment, and the adjacent support linear member portions 314 are made of two linear members (hereinafter called "the support linear member 314x") each of which is made of a single thread or the like. More concretely, both ends of the two support linear members 314x are fixed to the support portion 314a arranged on the stiffener portion 11 respectively and each intermediate portion of the support linear members 314x is supported in a slidably movable manner by the support portion 314b between the dividing points $12_2$, $12_4$ that form the peaks of the chevrons facing a distal end side when the ring portion 12 is folded. It is preferable that each support portion 314b is made so that the support linear member 314x can be inserted thereinto by an appropriate means such that a thread is wound around the ring portion 12 in an annular shape and fixed thereto or that the ring portion 12 is partially transformed to form a loop at each support portion 314b. In other words, each support linear member 314x forms an isosceles triangle with two support linear members 314 forming equilateral sides and an intermediate portion 314xa of the support linear member 314x forming a bottom.

Figure 33:
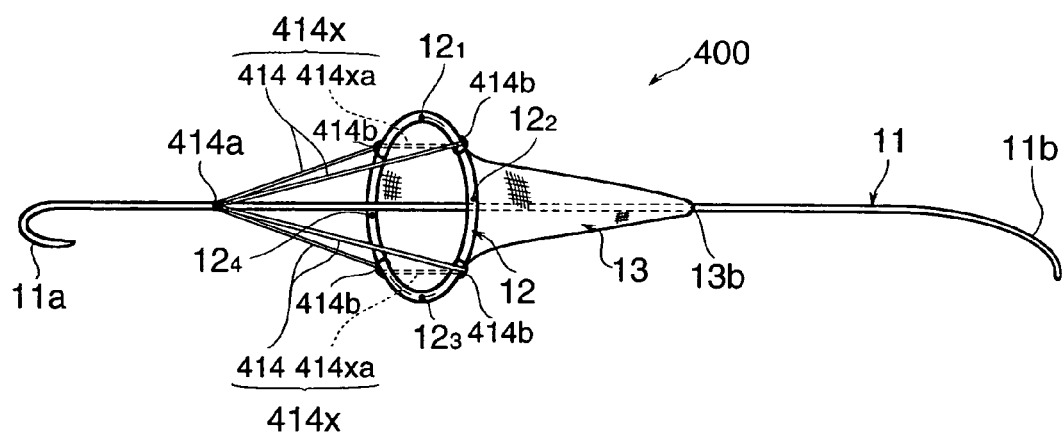
FIG. 33 is a perspective view showing a fifth embodiment of the alienated thrombus capture device.

In addition, an alienated thrombus capture device 400 shown in FIG. 33 has the same arrangement wherein support wire portions 414 comprises support linear members 414x, each of which is made of a thread, and both ends of the two support linear members 414x are fixed to the support portion 414a set on the stiffener portion 11 like the above-mentioned alienated thrombus capture device 300. However, unlike the alienated thrombus capture device 300, each intermediate portion of the support linear members 414x is supported in a slidably movable manner by the support portion 414b between the dividing points $12_1$, $12_3$ that form the bottoms of the valleys facing a proximal end side when the ring portion 12 is folded.

The alienated thrombus capture device 300, 400 is folded as follows when a captured thrombus is captured and retrieved from the blood vessel by the use of the alienated thrombus capture device 300, 400. The blood vessel 71 and the first catheter 3 are omitted to show in the following explanation and drawings. The engaging portion 5c of the wire 5 is in an engaged state with the hook portion 11a of the stiffener portion 11.

Figure 34:
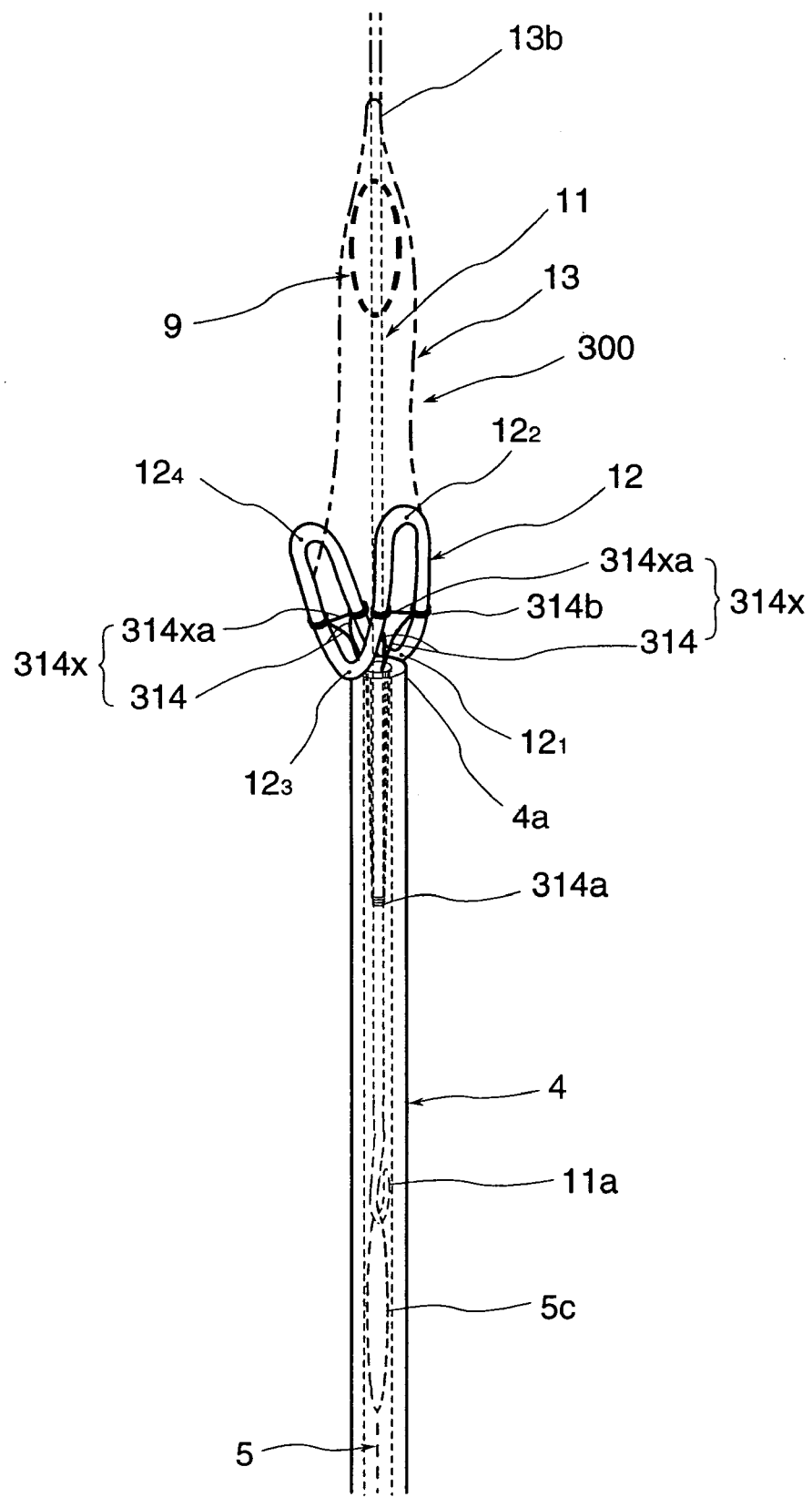
FIG. 34 is an explanatory view showing a process to retrieve the fourth embodiment.
Figure 35:
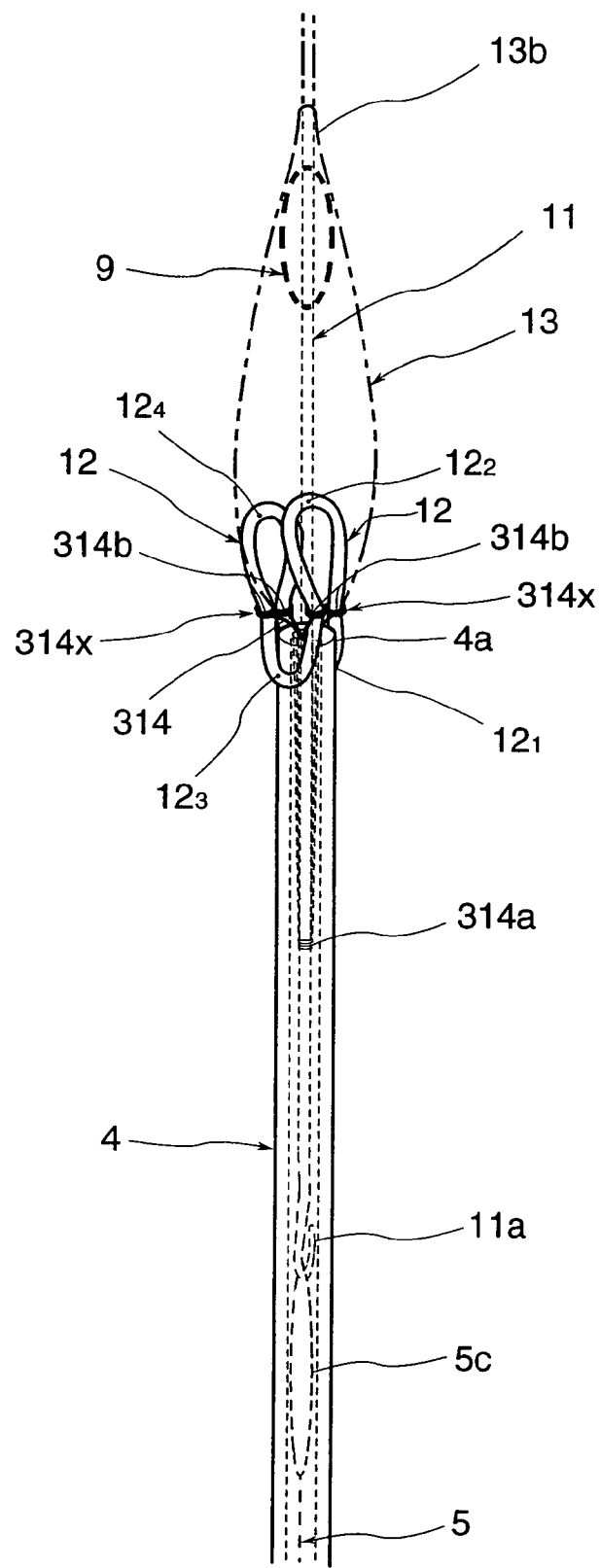
FIG. 35 is an explanatory view showing the retrieval process.

First, the alienated thrombus capture device 300 will be explained. As shown in FIG. 34, the second catheter 4 is paid out toward a distal end, and then the two support linear members 314x are enclosed in the distal end portion 4a of the second catheter 4 from a support portion 314a side. At this time, two support linear member portions 314 are gathered together and bound along the stiffener portion 11. Accordingly, each support linear member 314x makes a sliding movement toward a proximal end side at the support portion 314b and a length of the intermediate portion 314xa of the support linear member 314x between the support portions 314b and 314b is gradually shortened. As a result of this, each support portion 314b between the dividing points $12_2$, $12_4$ that form the peaks of the chevrons of the ring portion 12 are drawn by the intermediate portion 314xa of the support linear member 314x. Finally, as shown in FIG. 35, the alienated thrombus capture device 300 is completely folded in a state that the ring portion 12 makes contact at the support portions 314b between the dividing points $12_2$, $12_4$ and the ring portion 12 tightly holds the distal end portion 4a of the second catheter 4 at the dividing points $12_1$, $12_3$ that form the bottoms of the valleys.

Figure 36:
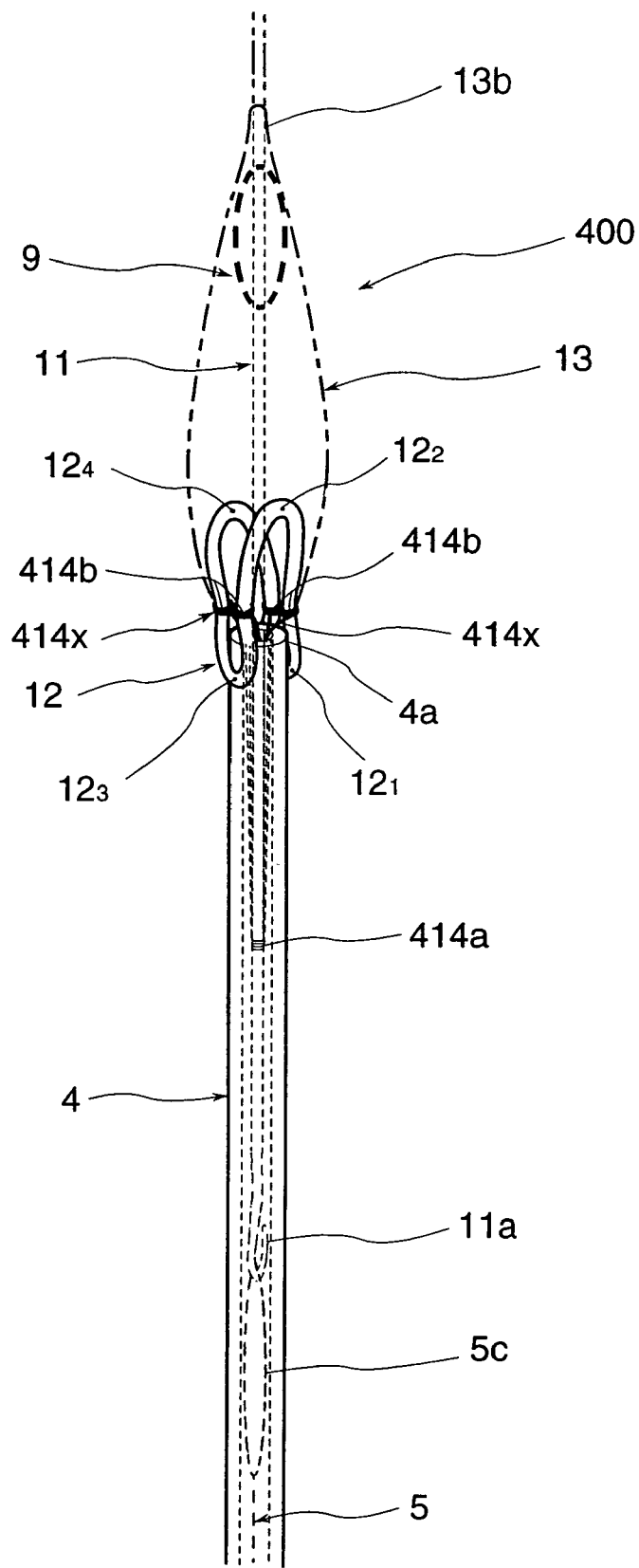
FIG. 36 is an explanatory view showing a process to retrieve the fifth embodiment.

The alienated thrombus capture device 400 will be shown only in a completely folded state in FIG. 36. In this case, a length of an intermediate portion 414xa is shortened between the support portions 414b between the dividing points $12_1$, $12_3$ that form the bottoms of the valleys. As a result, the alienated thrombus capture device 400 is completely folded in a state that the ring portion 12 makes contact at the support portions 414b and the ring portion 12 tightly holds the distal end portion 4a of the second catheter 4 at the dividing points $12_1$, $12_3$ that form the bottoms of the valleys.

In other words, since either of the alienated thrombus capture devices 300 and 400 can be folded into an extremely compact size, there is no danger of the thrombus 9 captured in the bursiform portion 13 spilling out and it is possible to retrieve the alienated thrombus capture devices 300 and 400 together with the second catheter 4. The arrangement of the alienated thrombus capture device 300 and that of the alienated thrombus capture device 400 may be combined to use four support linear members, although not shown in drawings, so that the four support linear members are supported by the adjacent two support portions out of the four support portions of the ring portion in a movable manner. In other words, two support linear members are supported by one support portion and each of the two support linear members is supported by a support portion located at an opposite adjacent portion of the support portion respectively. In accordance with this arrangement, since two pairs of the support portions located at four positions, each of which is located between the adjacent dividing points are drawn each other by the strained support linear members inserted into the second, the ring portion can be folded into a compact size.

Figure 37:
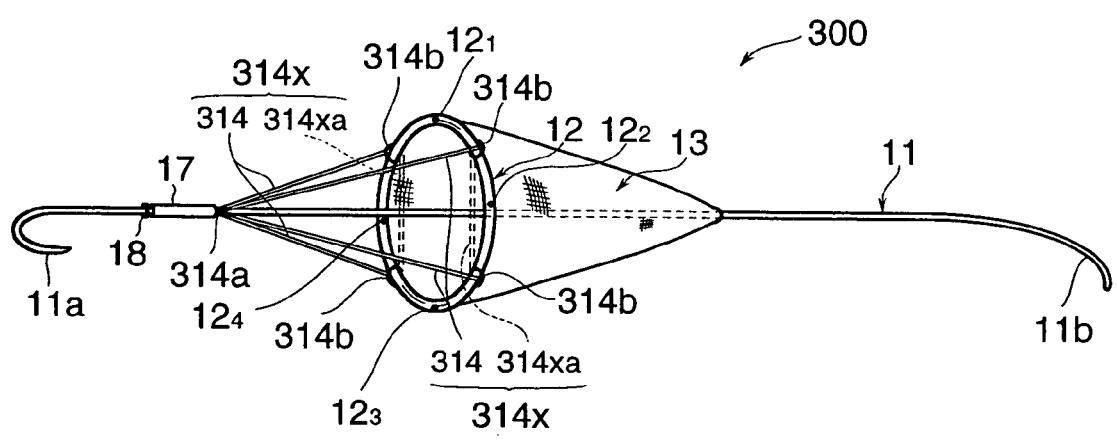
FIG. 37 is a perspective view showing a sixth embodiment of the alienated thrombus capture device to which a slider portion is applied.

In addition, a slider portion to bind the support linear member portions may be arranged on the stiffener portion 11 in order to narrow down the opening edge portion 13a of the bursiform portion 13 by folding the ring portion 12 into a further compact size. A slider portion 17 is applied to the alienated thrombus capture device 300 as shown in FIG. 37 in the following explanation However, the slider portion 17 may be applied to the alienated thrombus capture device 1 in accordance with the above-mentioned embodiments and other modified forms.

The slider portion 17 is a pipe-shaped member made of resin with a bore diameter a little larger than a diameter of the stiffener portion 11 and an external diameter not to be immerged into a lumen of the second catheter 4, and is arranged on the stiffener portion 11 between near the support portion 314a and inside the bursiform portion 13 in a slidably movable manner along the stiffener portion 11 with the stiffener portion 11 inserted thereinto. In order to restrain a movable range of the slider portion 17, a torose stopper portion 18 is arranged at a proximal end side of the stiffener portion 11 so that the slider portion 17 does not travel to a proximal end side by climbing over the stopper portion 18. The stopper portion 18 may be provided if necessary, and is not an essential component.

Figure 38:
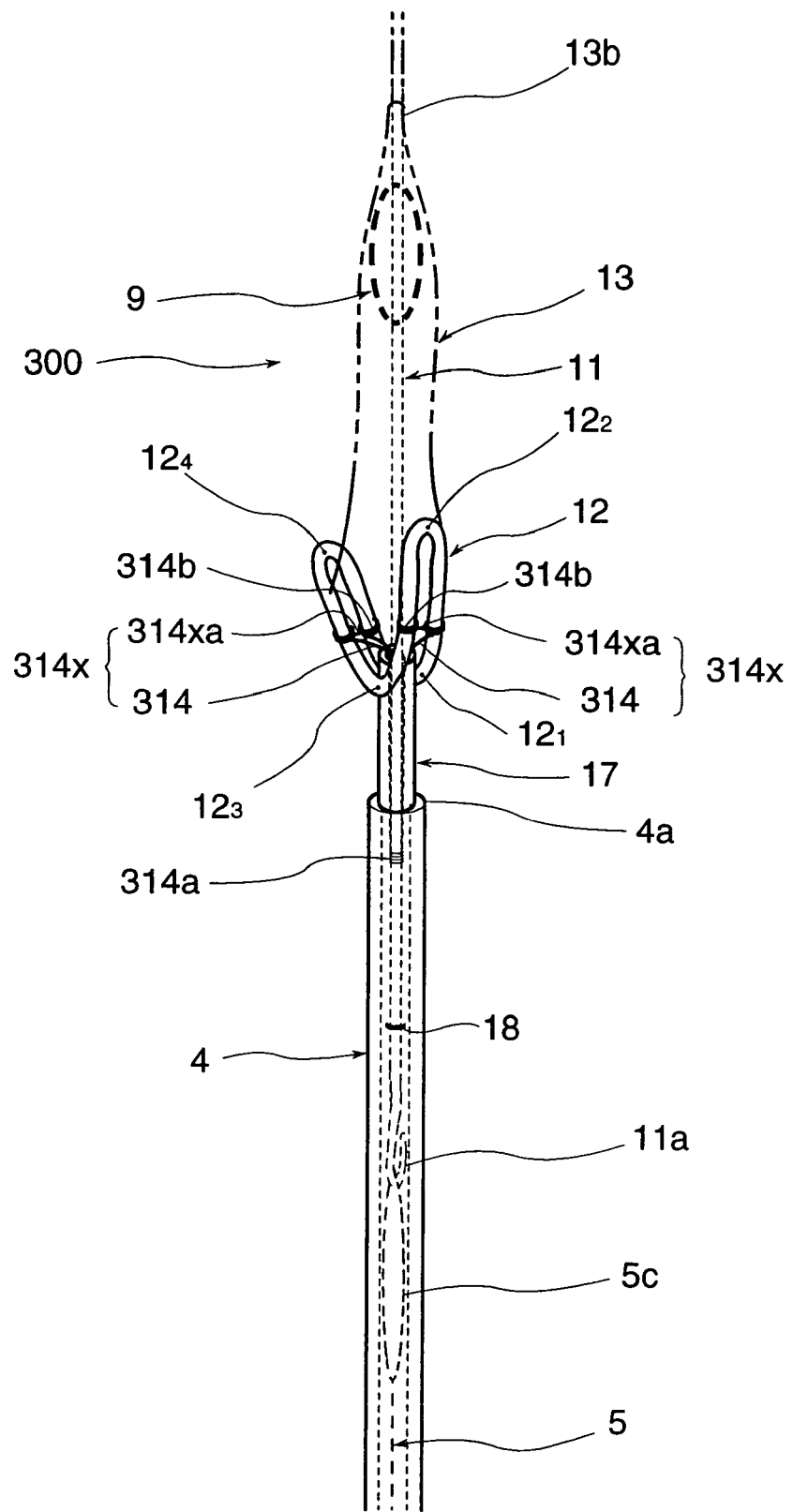
FIG. 38 is a perspective view showing a process of the alienated thrombus capture device in accordance with the sixth embodiment.
Figure 39:
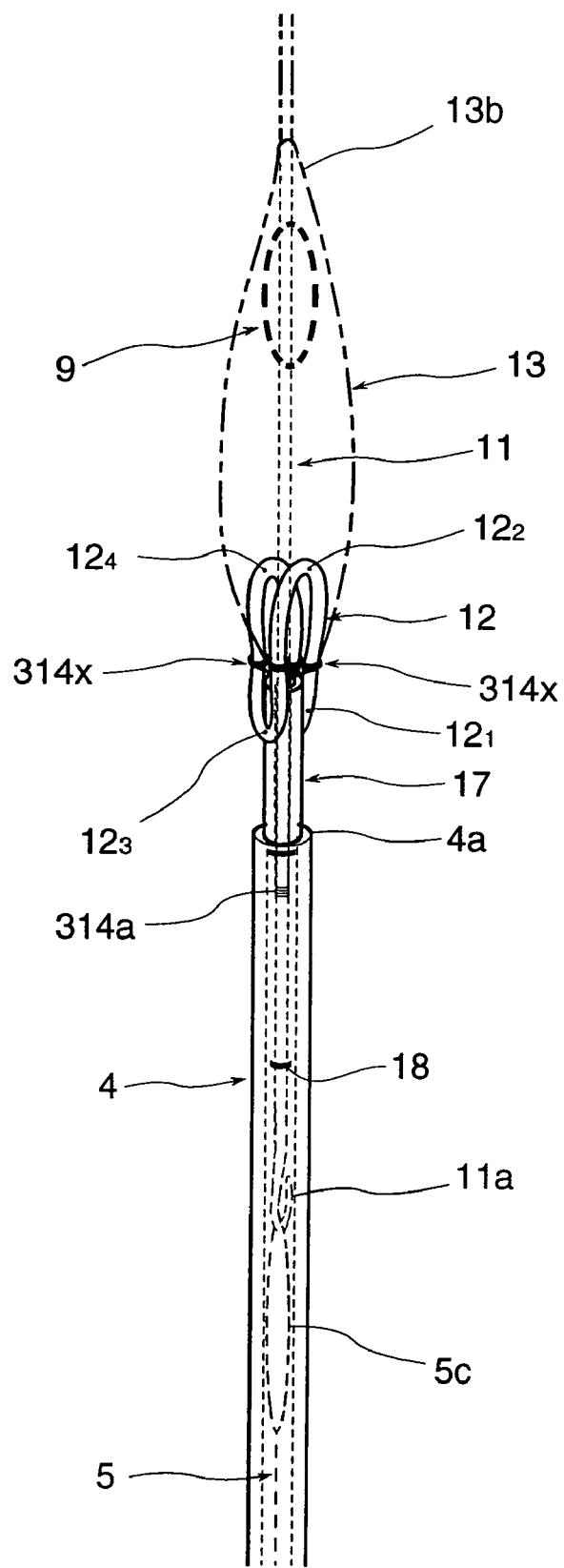
FIG. 39 is a perspective view showing a process of the alienated thrombus capture device in accordance with the sixth embodiment.

In order to retrieve the alienated thrombus capture device 300 having the slider portion 17 from the blood vessel 71, as shown in FIG. 38, the engaging portion 5c of the wire 5 is engaged with the hook portion 11a beforehand and the second catheter 4 is paid out so as to push the slider portion 17 toward a distal end side with a distal end of the second catheter 4. Then each support linear member portion 314 is gathered inside the slider portion 17 along the stiffener portion 11 and accordingly, a length of the support linear member 314xa between the support portions 314b of the ring portion 12 is shortened. As a result, the ring portion 12 is folded into a wavy shape. Further, the second catheter 4 is paid out to a distal end side, then the slider portion 17 climbs over a portion where the ring portion 12 is arranged so as to go inside the bursiform portion 13, and the support linear member portions 314 are gathered into the slider portion 17. As a result, as shown in FIG. 39, the ring portion 12 is folded to a degree that the support portions 314b, each located at a position between the dividing points $12_2$, $12_4$ that form the peaks of the chevrons facing a distal end side when folded contact and the dividing points $12_1$, $12_3$ that form the bottoms of the valleys, tightly hold the second catheter 4. Accordingly, it is possible to fold the ring portion 12 into a further compact size by applying the slider portion 17, thereby effectively preventing the thrombus 9 from spilling out.

Figure 40:
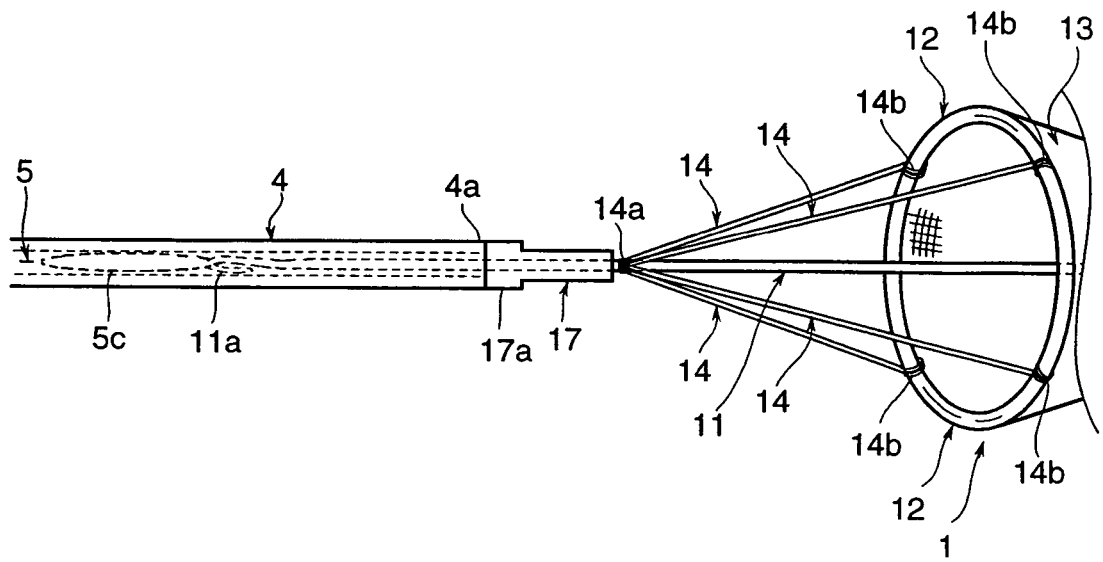
FIG. 40 is a magnified perspective view showing a modified form of the slider portion.
Figure 41:
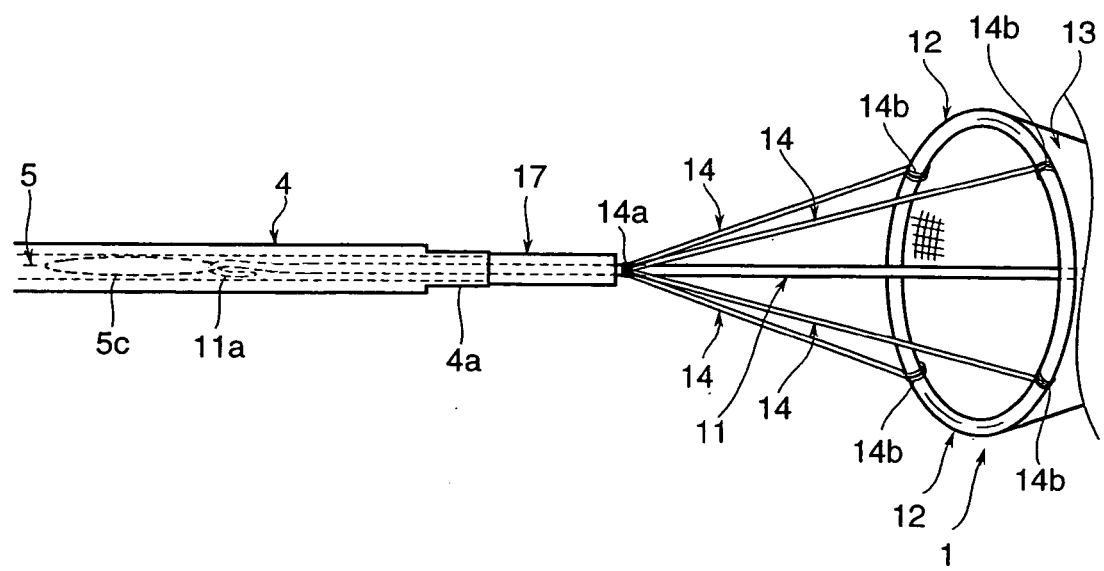
FIG. 41 is a magnified perspective view showing another method to retrieve the alienated thrombus capture device to which the slider portion is applied.

The following measure may be adopted in order to press the slider portion 17 with the second catheter 4 preferably. In FIG. 40 and FIG. 41, the alienated thrombus capture device 1 in accordance with the above-mentioned embodiments is applied. For example, as shown in FIG. 40 in a magnified manner, a big diameter portion 17a whose diameter is larger than a diameter of the distal end portion side of the slider portion 17 and is larger than an external diameter of the second catheter 4 is formed at a proximal end portion of the slider portion 17. If the distal end of the second catheter 4 makes abutting contact with the big diameter portion 17a, it is possible for the slider portion 17 not to immerge into the second catheter 4. It is preferable that the big diameter portion 17a is formed beforehand by a process. For example, a thread may be wound around the proximal end portion of the slider portion 17, a bump may be formed with a resin such as an adhesive or a slider portion may be made so that its outer diameter differs in the distal end side and the proximal end side and a step is formed at a boundary portion therebetween. In addition, if an external diameter of the distal end portion 4a of the second catheter 4 is thinned down to the extent of an external diameter of the slider portion 17, as shown in FIG. 41, it is possible for the distal end of the second catheter 4 to make abutting contact with a proximal end of the slider portion 17 steadily, thereby pushing the slider portion 17 preferably.

Figure 42:
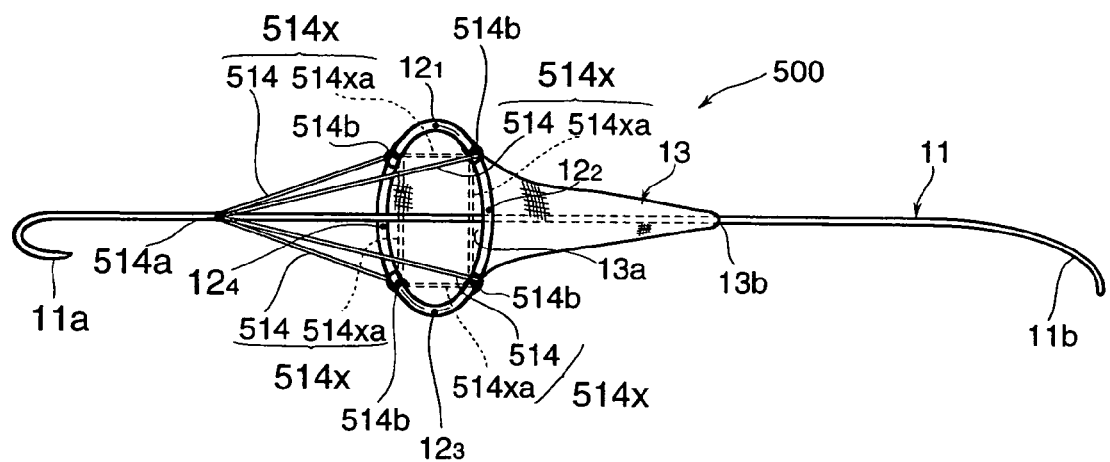
FIG. 42 is a perspective view showing a seventh embodiment of the alienated thrombus capture device.

An alienated thrombus capture device 500 shown in FIG. 42 may be represented as a preferable form. The alienated thrombus capture device 500 is so made that each of four support linear member portions 514 is made of a single support linear member 514x respectively and each support linear member 514x is supported by two adjacent support portions 514b on the ring portion 12. More specifically, an arrangement of the alienated thrombus capture device 500 is the same as that of the above-mentioned embodiment in that one end of each support linear member portion 514x is supported by a support portion 514a on the stiffener portion 11, and differs in that other end of each support linear member portion 514x is fixed to a single support portion 514b and an intermediate portion 514x is supported in a slidably movable by a support portion 514b next to the support portion 514b where the other end of the support linear member portion 514x is fixed.

Figure 43:
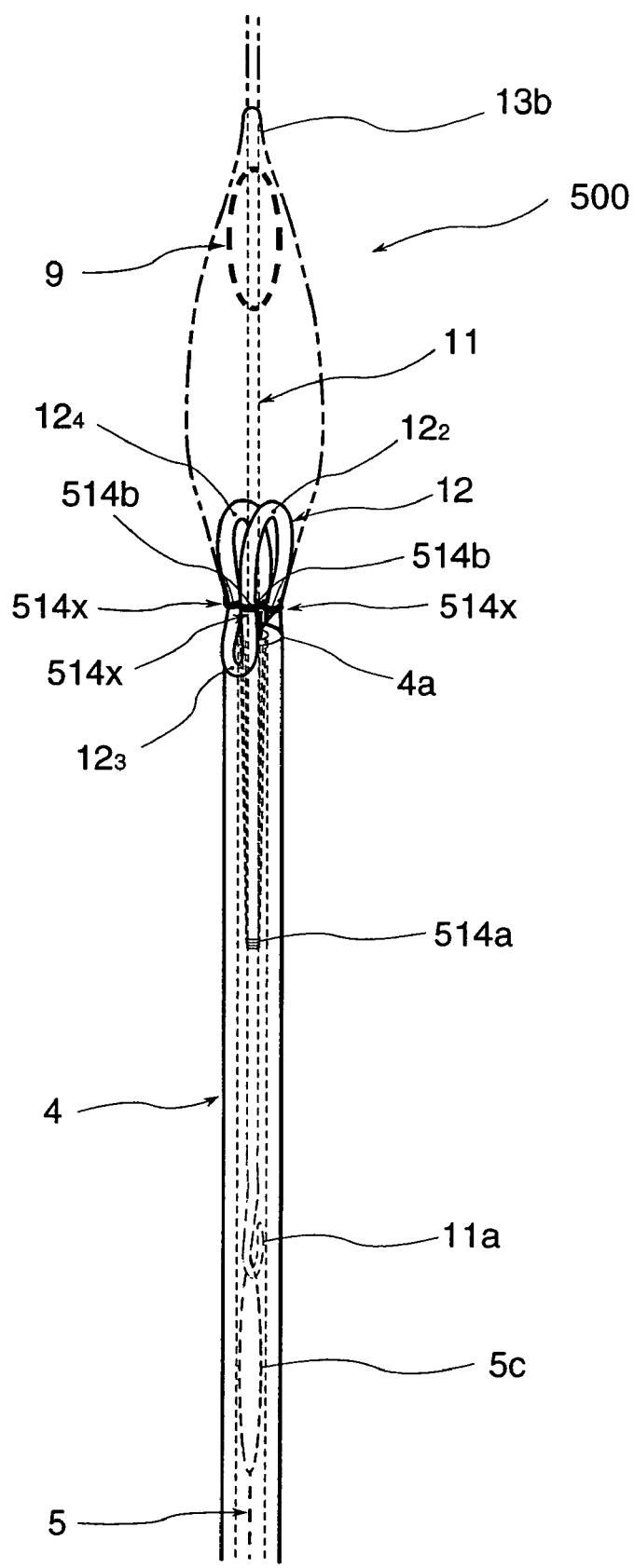
FIG. 43 is a perspective view showing a process to fold the alienated thrombus capture device in retrieving the alienated thrombus capture device in accordance with the seventh embodiment.

When the alienated thrombus capture device 500 is retrieved from the blood vessel, as shown in FIG. 43 like the above-mentioned alienated thrombus capture device 300, 400, the second catheter 4 is paid out to the distal end side, then each support linear member portion 514 is gathered inside the second catheter 4 in accordance with a movement of the second catheter 4. The intermediate portion 514xa makes a sliding movement to the ring portion 12 at the support portion 514b and the intermediate portion 514xa of the support linear member 514x shrinks between the adjacent support portions 514b. As a result, since the support portions 514b between the dividing points $12_2$, $12_4$, which form the peaks of the chevrons, and the dividing points $12_1$, $12_3$, which that form the bottoms of the valleys, approach each other, the ring portion 12 can be folded to be small. In this case also, it is a matter of course that the slider potion 17 can be applied.

Figure 44:
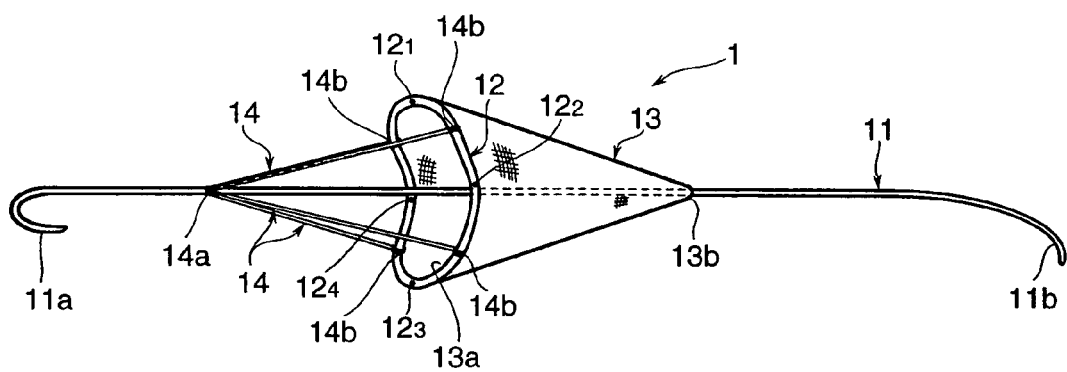
FIG. 44 is a perspective view showing an eighth embodiment of the alienated thrombus capture device wherein a ring portion is transformed in a wavy shape beforehand.
Figure 45:
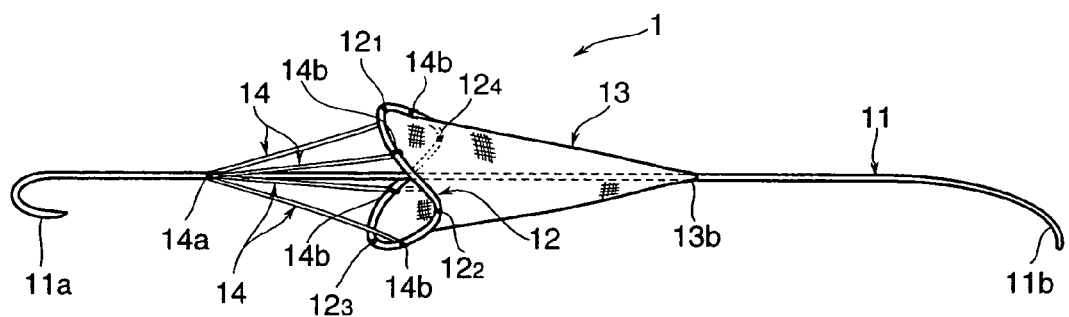
FIG. 45 is a perspective view showing a process to fold the alienated thrombus capture device in accordance with the eighth embodiment.

For each of the above-mentioned alienated thrombus capture devices the ring portion 12 is generally in a shape of a circle in a spread state. However, the ring portion 12 may be formed in a slightly wavy shape in a spread state (1a) corresponding to a folded habit given to the ring portion 12 as shown in FIG. 44. In other words, the alienated thrombus capture device 1 shown in FIG. 44 is the same as that of the embodiment explained previously, except that the ring portion has a slightly inflected shape due to a habit formed strongly at four dividing points $12_1$, $12_2$, $12_3$, $12_4$, which are the peaks of the chevrons or the bottoms of the valleys when folded. As a result, when the ring portion 12 is pushed from the outside or the support linear member portions 14 are gathered along the stiffener portion 11 with a tension applied, the ring portion 12 is folded by the external force into a similar shape as that of the above-mentioned embodiment as shown in FIG. 45. Since the ring portion 12 has a wavy shape when in the spread state, it is possible to easily fold the ring portion 12 into a desired shape extremely.

Figure 46:
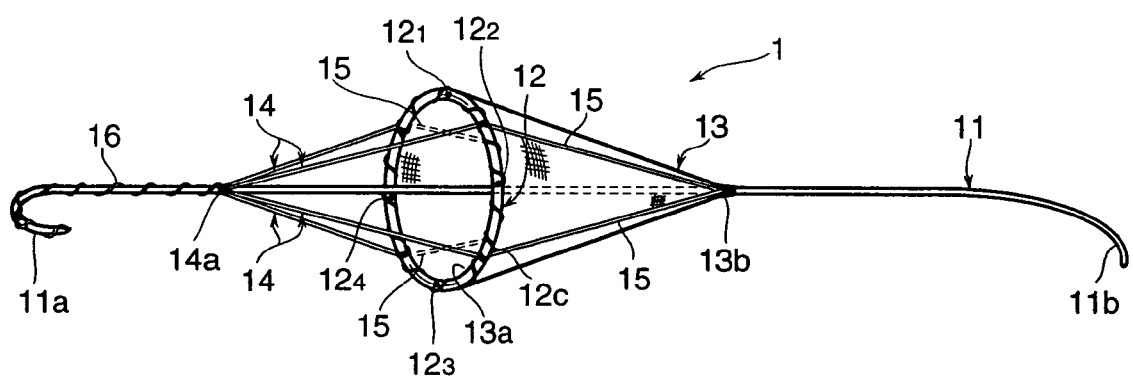
FIG. 46 is a perspective view showing a ninth embodiment in which each part is reinforced.

In addition, reinforcement may be provided as shown in FIG. 46 in order to improve the strength of each component. More specifically, a reinforcement thread 12c may be spirally wound around the ring portion 12, which makes it possible to reinforce the ring portion 12, thereby improving the shape retaining characteristics of the ring portion 12. In addition, the opening edge portion 13a of the bursiform portion 13 may be sewed up to the ring portion 12 with this reinforcement thread 12c. Further, if an auxiliary linear member 15 made of a similar material as that of the support linear member portion 14 is bridged in a strained state between the support portion 14b on the ring portion 12 and a position on the stiffener portion 11 to which a closed edge portion 13b of the bursiform portion 13 is mounted, the shape retaining characteristics of the bursiform portion 13 are improved, thereby stabilizing the posture of the ring portion 12. In addition, the support linear member portion 14 and the auxiliary linear member 15 supported by the same support portion 14b may be made of a single linear member and an intermediate portion of the linear member may be wound to fix to the support portion 14b on the ring portion 12. If a reinforcement thread 16 is spirally wound around the proximal end portion of the stiffener portion 11, it is possible to reinforce the stiffener portion 11 pulled by the wire 5 with strong force. The reinforcement thread 12c, the reinforcement linear member 15 and the reinforcement thread 16 are auxiliary components to be used if required, and all of them are not necessarily applied at once and either one or two or more may be applied if necessary.

Figure 47:
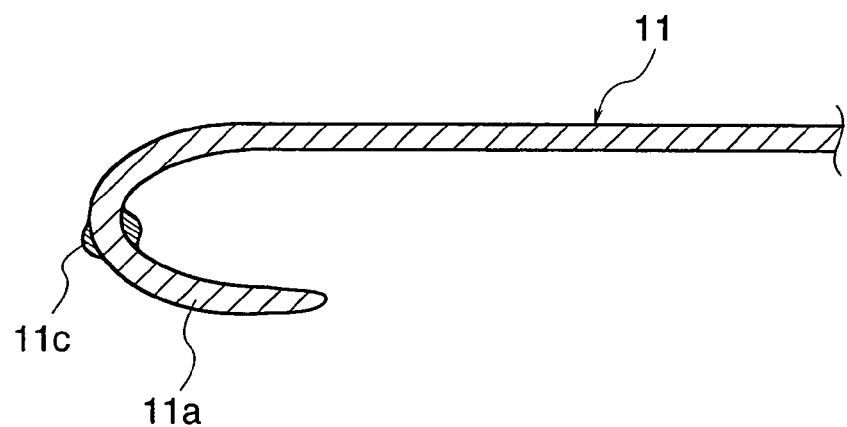
FIG. 47 is a magnified cross-sectional view showing a modified form of a project portion of the stiffener portion of the ninth embodiment.
Figure 48:
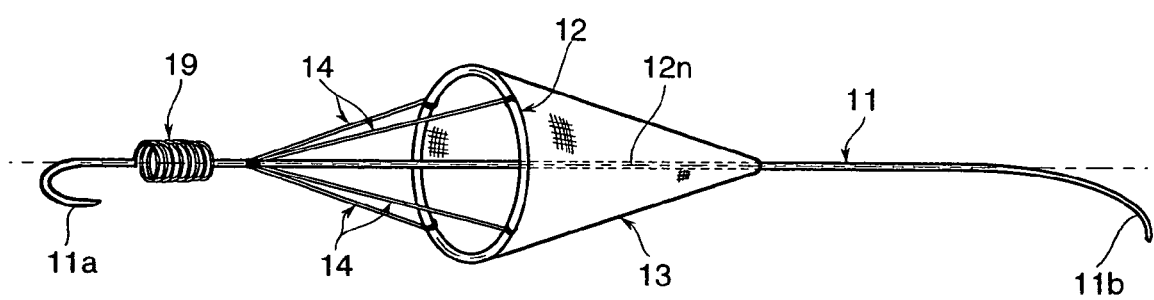
FIG. 48 is a view showing a tenth embodiment wherein a helical posture stabilizer is formed at a proximal end portion of the stiffener portion.

In order to achieve a good engagement state of the hook portion 12a on the stiffener portion 11 and the engaging portion 5c of the wire 5, it is preferable that a slip stopper portion 11c having bumpy shape is formed on the hook portion 11a as shown in FIG. 47. The slip stopper portion 11c is formed by mounting a bump made of, for example, nickel titanium alloy with its center portion made thick and its peripheral portion made thin on the stiffener portion 11 by an appropriate means such as an adhesive, thereby improving the state of engagement or release of the projecting portion 5c1 at the engaging portion 5c of the wire 5. The slip stopper portion 11c may have another arrangement and may be a bump formed with a thread wound around the stiffener portion 11.

In addition, if the proximal end portion of the stiffener portion 11, especially the hook portion 11a, makes contact with the inner wall 71a of the blood vessel 71, it becomes difficult to retrieve the alienated thrombus capture device 1 by hooking the engagement portion 5c of the wire 5 with the hook portion 11a. As a result, it is preferable that the proximal end portion side of the stiffener portion 11 is enclosed within a range of a diameter of the ring portion 12 that makes a contact with the inner wall 71a of the blood vessel 71. Then it is preferable that a shank of the stiffener portion 11 extending in a generally straight line generally coincides with the center axis 12n of the ring portion 12. Then, if a posture stabilizing portion 19 in a spirally wound shape is formed on a part of the proximal end portion of the stiffener portion 11, the posture of the stiffener portion 11 at the proximal end side is stabilized. It is a matter of course that the spiral posture stabilizing portion 19 and the hook portion 11a are required to be a size smaller than a radius of the ring portion 12 from the center axis of the ring portion 12 and are not to be separated from the shank of the stiffener portion 11 at an arbitrary portion.

Figure 49:
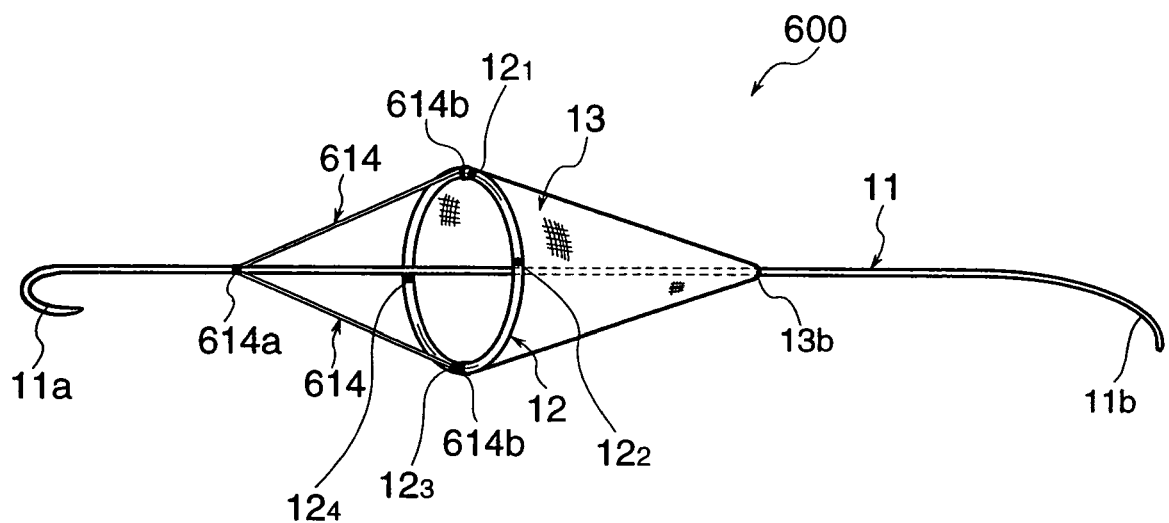
FIG. 49 is a perspective view showing an eleventh embodiment of the alienated thrombus capture device.
Figure 50:
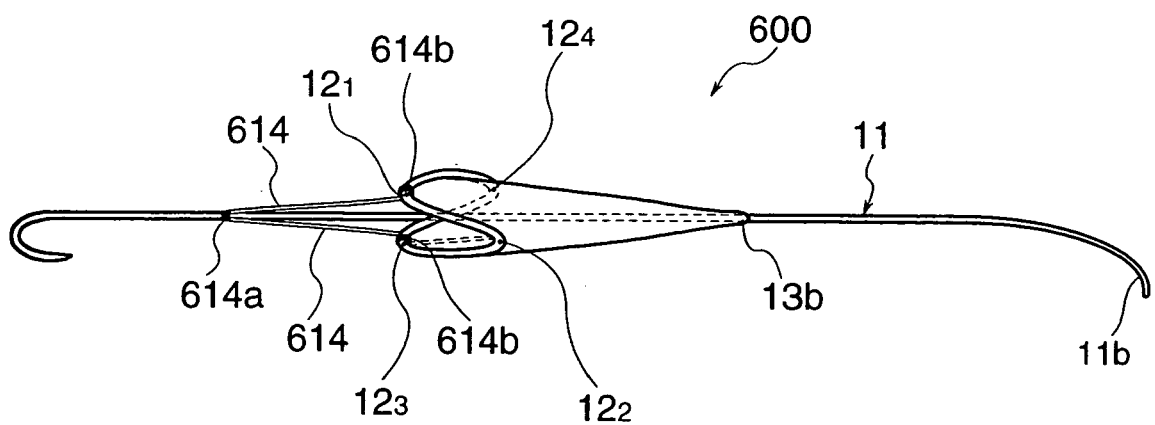
FIG. 50 is a perspective view showing a process to fold the alienated thrombus capture device in accordance with the eleventh embodiment.

In addition to the above, a number of the support linear member portions 14 may be set arbitrary. For example, an alienated thrombus capture device 600 shown in FIG. 49 has two support linear member portions 614. The alienated thrombus capture device 600 has four dividing points $12_1$, $12_2$, $12_3$, $12_4$ that generally quadrisect the circumference of the ring portion 12 like the above embodiment. When the ring portion 12 is folded into a wavy shape with a pair of the facing dividing points $12_1$, $12_3$, forming the bottoms of the valleys facing the proximal end side of the stiffener portion 11, and a pair of other dividing points $12_2$, $12_4$, forming the peaks of the chevrons facing the distal end side of the stiffener portion 11, as shown in FIG. 50, support portions 614b of support linear member portions 614 are set on the dividing points $12_1$, $12_3$ as the bottoms of the valleys respectively. A position of a support portion 614a of the support linear member portion 614 is the same as that of the above-mentioned embodiment.

Figure 51:
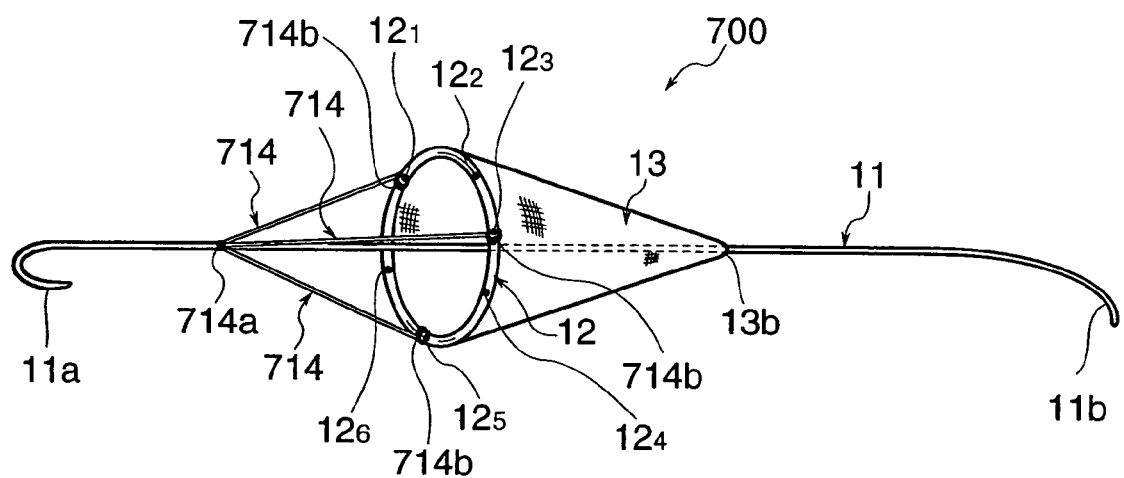
FIG. 51 is a perspective view showing a twelfth embodiment of the alienated thrombus capture device.
Figure 52:
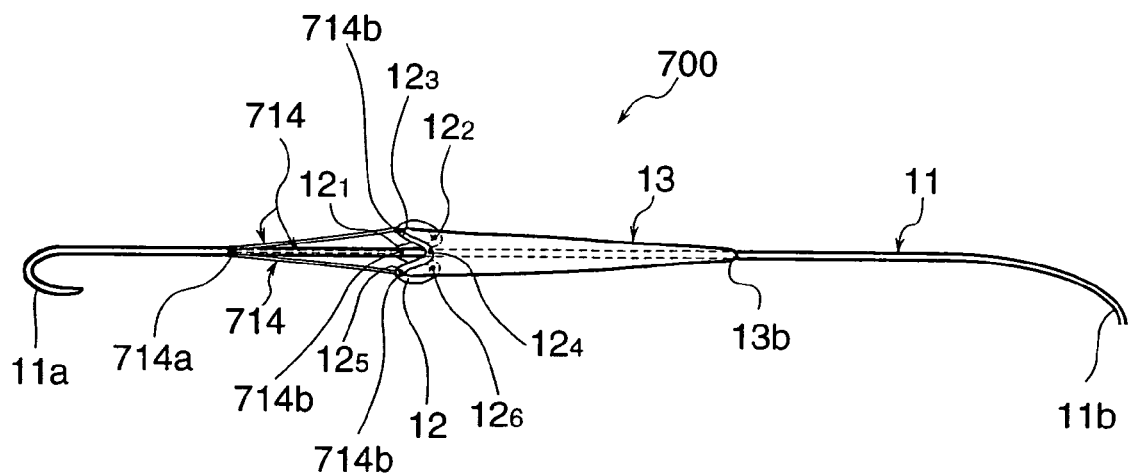
FIG. 52 is a perspective view showing a process to fold the alienated thrombus capture device in accordance with the twelfth embodiment.

In addition, an alienated thrombus capture device 700 shown in FIG. 51 has three support linear member portions 614. The alienated thrombus capture device 700 has six dividing points $12_1$, $12_2$, $12_3$, $12_4$, $12_5$, $12_6$, each of which divides the circumference of the ring portion 12 into six generally equal sections. When the ring portion 12 is folded into a wavy shape with every other dividing points $12_1$, $12_3$, $12_5$ forming the bottoms of the valleys facing the proximal end side of the stiffener portion 11 and the other dividing points $12_2$, $12_4$, $12_6$ forming the peaks of the chevrons facing the distal end side of the stiffener portion 11 as shown in FIG. 52, support portions 714b of support linear member portions 714 are set on the dividing points $12_1$, $12_3$, $12_5$ respectively. A position of a support portion 714a of the support linear member portion 714 is the same as that of the above-mentioned embodiment.

The above-mentioned alienated thrombus capture device is separated from the transport device, however, the alienated thrombus capture device may be integrated into the transport device as will be explained next.

Figure 53:
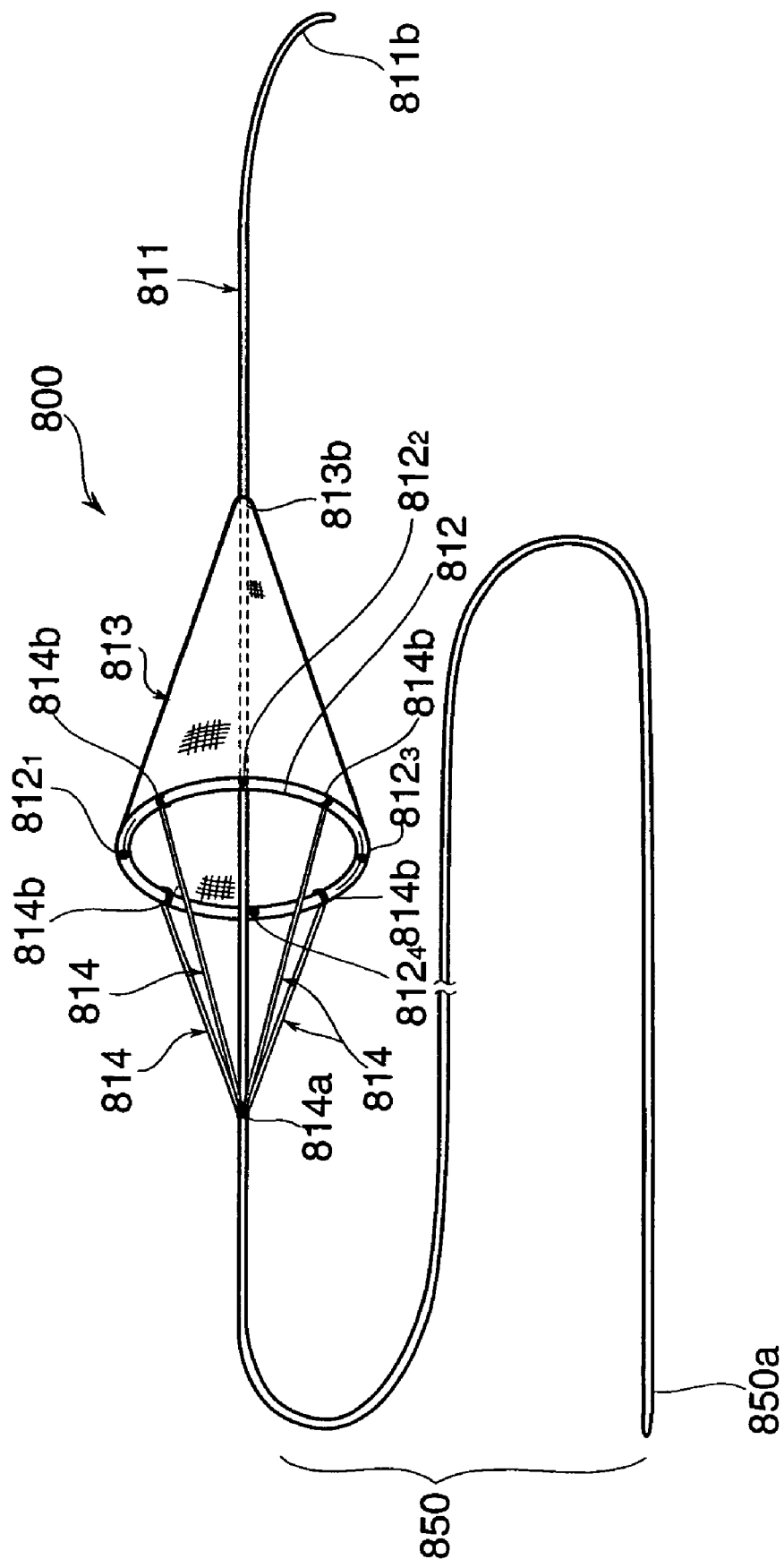
FIG. 53 is a perspective view showing an alienated thrombus capture device integrated into a transport device.
Figure 54:
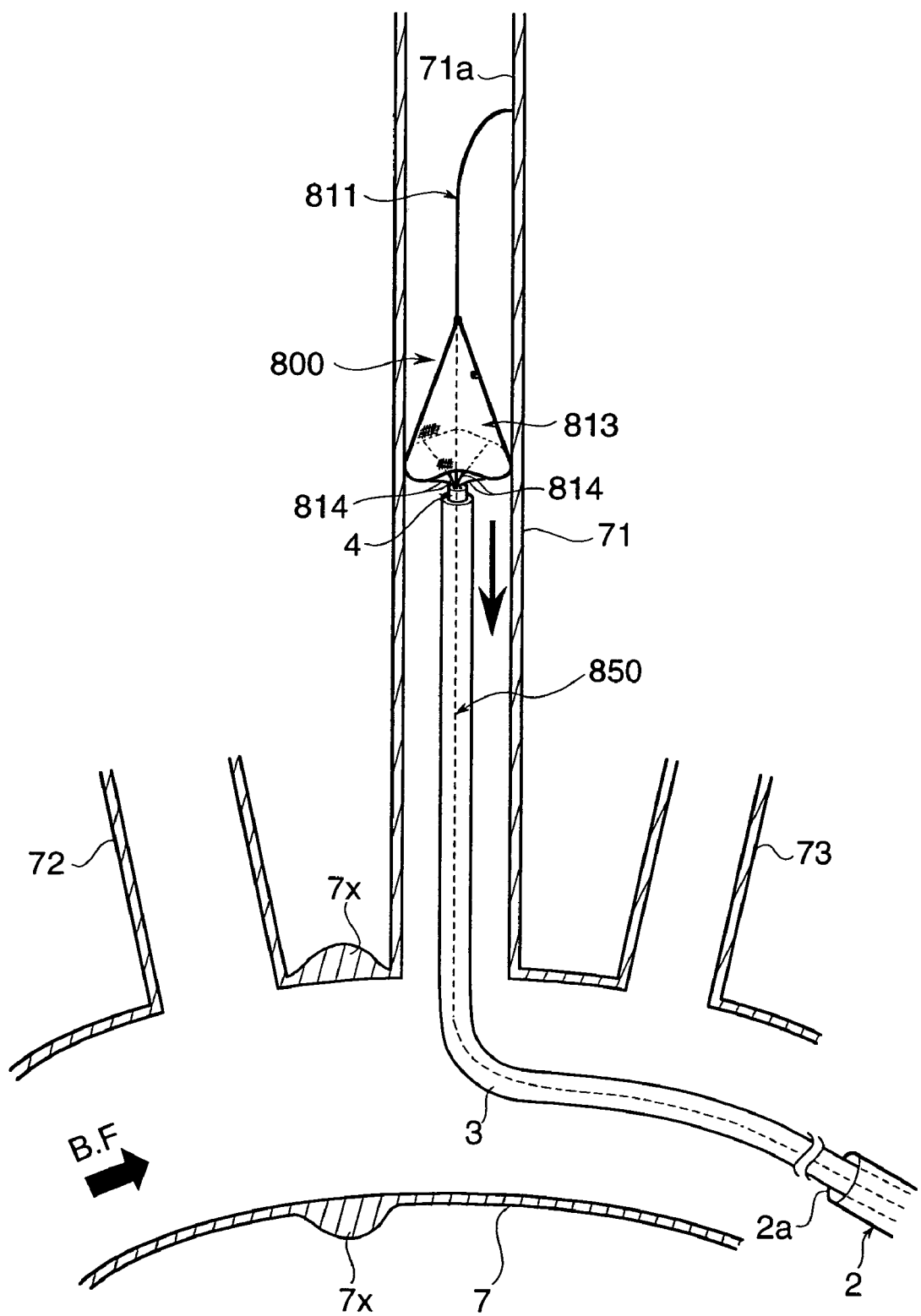
FIG. 54 is en explanatory view showing a process to transport the alienated thrombus capture device integrated into the transport device.

An alienated thrombus capture device 800 shown in FIG. 53 comprises a ring portion 812 having the same arrangement as that of the above-mentioned embodiment, a bursiform portion 813, a support linear member portion 814 and an auxiliary linear member portion 815 and four dividing points $812_1$, $812_2$, $812_3$, $812_4$ of the ring portion 812 and a support portion 814b of the support linear member portion 814 are similar to those of the above-mentioned embodiment. Meanwhile, a stiffener portion is integrally formed with a lengthwise wire as an operating member. A portion from a distal end of the wire to a little beyond a support portion 814a of the support linear member portion 814 is set as the stiffener portion 811 and a portion from a little beyond the support portion 814a to a proximal end of the wire is set as an operating portion 850. For the alienated thrombus capture device 800 of this arrangement, the operating portion 850 plays the same role as that of the wire 5. In other words, a proximal end portion 850a of the operating portion 850 can be operated from outside the body. As shown in FIG. 54, for example, the whole of the alienated thrombus capture device 800 can be transported by paying out or pulling the proximal end portion 850a into the second catheter 4. The alienated thrombus capture device 800 differs from the above embodiment in that it is impossible to separate the operating portion 850 from the stiffener portion 811 during treatment of detaining an artificial blood vessel and the operating portion 850 always resides in a blood vessel. With this arrangement, stability in a blood vessel, reliability of capturing a thrombus and convenience of transportation can be secured sufficiently.

As mentioned above, the present claimed invention is embodied by the above-described embodiments, however, it is not limited to the above-described embodiments and various modifications may be made without departing from the spirit of the invention.

POSSIBLE APPLICATIONS IN INDUSTRY

As mentioned above, the alienated thrombus capture device in accordance with the present claimed invention is useful as a filter device that is high in security, easy to handle and of a simple arrangement, and a folding method of this invention secures a stable state that the ring portion is folded and also improves security in transporting the alienated thrombus capture device.

The invention claimed is:
1. An alienated thrombus capture device comprising:
   a ring portion having an approximately ring shape and comprising a wire member having foldable elasticity,
   a flexibly transformable linear stiffener portion that penetrates the ring portion,
   a porous bursiform portion comprising an open edge portion mounted on the ring portion and a closed edge portion mounted on a part of a distal end side of the stiffener portion, and
   a plurality of flexibly transformable support linear member portions attached to a support portion on the stiffener portion at a proximal end side of said stiffener portion relative, to the closed edge portion of the bursiform portion, and a support portion on the ring portion in a strained state, wherein when an outside force is exerted on said flexibly transformable support linear member portions, said flexibly transformable support linear member portions are drawn toward said stiffener portion, and then when said ring portion is subjected to tensions of said support linear member portions exerted by said outside force, said ring portion folds from an expanded state into a transport state wherein a plurality of peaks facing the distal end side of the stiffener portion and a plurality of valleys facing the proximal end side of the stiffener portion are alternately formed in accordance with a wavy shape, wherein the plurality of flexibly transformable support linear member portions and support portions on said ring portion are disposed radially at equal points, each of which generally equally divides the circumference of the ring portion, wherein said alienated thrombus capture device further comprises dividing points that generally equally divide the circumference of the ring portion into an even number of four or greater parts, wherein the support portions on the ring portion are formed at middle points between adjacent dividing points, and wherein at least every other dividing point divides the ring portion such that the ring portion can be folded, so that every other dividing point forms a peak facing a distal end side of the stiffener portion and the other dividing points form valleys facing the proximal end side of the stiffener portion.

2. The alienated thrombus capture device described in claim 1, wherein four dividing points are formed on the ring portions and the support portions on the ring portion are formed at middle points between adjacent dividing points.

3. The alienated thrombus capture device described in claim 1, wherein a first end portion of the flexibly transformable support linear member portions is fixed to the support portion on the stiffener portion, and a second end portion of the flexibly transformable support linear member portions is fixed to the support portion on the ring portion.

4. The alienated thrombus capture device described in claim 1, wherein both ends of the flexibly transformable support linear member portions are fixed to the support portion on the stiffener portion and an intermediate portion of the flexibly transformable support linear member portions is supported in a slidably movable manner by a pair of adjacent support portions on the ring portion.

5. The alienated thrombus capture device described in claim 1, wherein a first end portion of the flexibly transformable support linear member portions is fixed to the support portion on the stiffener portion, a second end portion of the flexibly transformable support linear member portions is fixed to one of the support portions on the ring portion, and an intermediate portion of the flexibly transformable support linear member portions is supported in a slidably movable manner by the support portion adjacent to the support portion that fixes the second end portion.

6. The alienated thrombus capture device described in claim 1, further comprising a tubular slider portion into which the stiffener portion is inserted, said tubular slider portion being slidably movable along the stiffener portion and arranged on the stiffener portion, wherein the flexibly transformable support linear member portions are enclosable into the inside of the tubular slider portion, and are gathered along the stiffener portion by moving the tubular slider portion in a distal end direction of the stiffener portion.

7. The alienated thrombus capture device described in claim 6, wherein a large diameter portion, whose diameter is greater than that of a distal end portion of the tubular slider portion, is formed at a proximal end portion of an outer circumferential wall of the tubular slider portion.

8. The alienated thrombus capture device described in claim 6, further comprising a stopper portion formed proximal to the support portion on the stiffener portion and proximal to the proximal end portion of the tubular slider portion, said stopper portion restraining the tubular slider portion from moving in the proximal end side direction.

9. The alienated thrombus capture device described in claim 1,
wherein said alienated thrombus capture device is detachably mountable onto a transport device to transport the alienated thrombus capture device by directly or indirectly pushing or pulling the proximal end side of the stiffener portion.

10. The alienated thrombus capture device described in claim 9, further comprising a held portion formed at the proximal end portion of the stiffener portion, said held portion to be held by the transport device.

11. The alienated thrombus capture device described in claim 10,
wherein the held portion of said alienated thrombus capture device is formed by partially curving or bending the proximal end portion of the stiffener portion, and
wherein the held portion is holdable by a loop shaped engaging portion of said transport device, which is selectively expandable and shrinkable and which is formed in a holding portion comprised on the distal end portion of said transport device, after the held portion is hooked with the engaging portion by passing the held portion through the expanded engaging portion of the holding member.

12. The alienated thrombus capture device described in claim 11, further comprising a slip stopper portion formed on the held portion that prevents separation from the engaging portion by making an engagement with a part of the shrunken engaging portion of the holding member.

13. The alienated thrombus capture device described in claim 11, wherein a maximum distance between a center axis of the ring portion and the proximal end portion of the stiffener portion is less than or equal to a radius size of the ring portion.

14. The alienated thrombus capture device described in claim 13, further comprising a spiral portion whose axial center generally coincides with a center axis of the ring portion formed distal to the held portion of the stiffener portion.

15. The alienated thrombus capture device described in claim 1, wherein the stiffener portion is integrally formed with or mounted on a part of a transport device for transporting the alienated thrombus capture device.

16. The alienated thrombus capture device described in claim 1, wherein the alienated thrombus capture device can be moved by directly operating the proximal end side of the stiffener portion by a user.

17. The alienated thrombus capture device described in claim 1, further comprising a guide portion formed in said stiffener portion by elongating the distal end portion of the stiffener portion distally from the closed edge portion of the bursiform portion, and partially curving or bending the elongated distal end portion.

18. The alienated thrombus capture device described in claim 1, wherein the ring portion is folded prior to use in a wavy shape by approaching the ring portion to the stiffener portion so that every other dividing point forms a peak facing the distal end side of the stiffener portion, and the other dividing points form valleys facing the proximal end side of the stiffener portion.

19. The alienated thrombus capture device described in claim 18, wherein the ring portion is formed in the wavy shape in a spread state.

20. The alienated thrombus capture device described in claim 1, further comprising a projecting portion formed on said ring portion which projects to the proximal end side of the stiffener portion when the ring portion is folded.

21. The alienated thrombus capture device described in claim 1, wherein said ring portion returns from said transport state to said expanded state by elastic memory force.

22. The alienated thrombus capture device described in claim 1, wherein said dividing points generally equally divide the circumference of the ring portion into four parts,
   wherein only two flexibly transformable support linear member portions are provided, and
   wherein said two flexibly transformable support linear member portions are attached to the support portion on the ring portion at locations coinciding with alternate dividing points.

23. An alienated thrombus capture device comprising:
   a ring portion comprising a wire member having foldable elasticity,
   a flexibly transformable linear stiffener portion that penetrates the ring portion,
   a porous bursiform portion comprising an open edge portion mounted on the ring portion and a closed edge portion mounted on a part of a distal end side of the stiffener portion,
   plurality of flexibly transformable support linear member portion attached to a support portion on the stiffener portion at a proximal end side of said stiffener portion, relative to the closed edge portion of the bursiform portion, and a support portion on the ring portion in a strained state, and
   dividing points that generally equally divide the circumference of the ring portion into an even number of four or greater parts,
   wherein when an outside force is exerted on said ring portion, said ring portion elastically folds from an expanded state into a transport state wherein a plurality of peaks facing the distal end side of the stiffener portion and a plurality of valleys facing the proximal end side of the stiffener portion are alternately formed, or vice versa,
   wherein the support portions on the ring portion are formed at middle points between adjacent dividing points, and
   wherein at least every other dividing point divides the ring portion such that the ring portion can be folded, so that every other dividing point forms a peak facing a distal end side of the stiffener portion and the other dividing points form valleys facing the proximal end side of the stiffener portion.

24. An alienated thrombus capture combination, comprising:
   an alienated thrombus capture device, comprising:
      a ring portion having an approximately ring shape and comprising a wire member having foldable elasticity,
      a flexibly transformable linear stiffener portion that penetrates the ring portion,
      a porous bursiform portion comprising an open edge portion mounted on the ring portion and a closed edge portion mounted on a part of a distal end side of the stiffener portion,
      a plurality of flexibly transformable support linear member portions attached to a support portion on the stiffener portion at a proximal end side of said stiffener portion, relative to the closed edge portion of the bursiform portion, and a support portion on the ring portion in a strained state, and
   a transport device onto which the alienated thrombus capture device is detachably mounted to transport the alienated thrombus capture device,
   wherein the alienated thrombus capture device is transported by the transport device by directly or indirectly pushing or pulling the proximal end side of the stiffener portion,
   wherein an outside force is exerted on said flexibly transformable support linear member portions, said flexibly transformable support linear member portions are drawn toward said stiffener portion, and then when said ring portion is subjected to tensions of said support linear member portions exerted by said outside force, said ring portion folds from an expanded state into a transport state wherein a plurality of peaks facing the distal end side of the stiffener portion and a plurality of valleys facing the proximal end side of the stiffener portion are alternately formed in accordance with a wavy shape,
   wherein said alienated thrombus capture device further comprises dividing points that generally equally divide the circumference of the ring portion into an even number of four or greater parts,
   wherein the support portions on the ring portion are formed at middle points between adjacent dividing points, and
   wherein at least every other dividing point divides the ring portion such that the ring portion can be folded, so that every other dividing point forms a peak facing a distal end side of the stiffener portion and the other dividing points form valleys facing the proximal end side of the stiffener portion.

25. The alienated thrombus capture combination described in claim 24, further comprising a held portion formed at the proximal end portion of the stiffener portion, said held portion to be held by the transport device.

26. The alienated thrombus capture combination described in claim 25, wherein the transport device comprises a holding member having an engaging portion of a loop shape that is selectively expandable and shrinkable at its distal end portion, the held portion of said alienated thrombus capture device is formed by partially curving or bending the proximal end portion of the stiffener portion, and the held portion is held by the shrunken engaging portion after the held portion is hooked with the engaging portion by passing the held portion through the expanded engaging portion of the holding member.

27. The alienated thrombus capture combination described in claim 26, further comprising a slip stopper portion formed on the held portion that prevents separation from the engaging portion by making an engagement with a part of the shrunken engaging portion of the holding member.

28. The alienated thrombus capture combination described in claim 26, wherein a maximum distance between a center axis of the ring portion and the proximal end portion of the stiffener portion is less than or equal to a radius size of the ring portion.

29. The alienated thrombus capture combination described in claim 28, further comprising a spiral portion whose axial center generally coincides with a center axis of the ring portion formed distal to the held portion of the stiffener portion.

* * * * *